(12) United States Patent
Liu

(10) Patent No.: US 12,421,284 B2
(45) Date of Patent: Sep. 23, 2025

(54) CHIMERIC NEUROTOXINS

(71) Applicant: IPSEN BIOPHARM LIMITED, Wrexham (GB)

(72) Inventor: Sai Man Liu, Wrexham (GB)

(73) Assignee: IPSEN BIOPHARM LIMITED, Wrexham (GB)

( * ) Notice: Subject to any disclaimer, the term of this patent is extended or adjusted under 35 U.S.C. 154(b) by 694 days.

(21) Appl. No.: 17/811,958

(22) Filed: Jul. 12, 2022

(65) Prior Publication Data

US 2023/0025090 A1 Jan. 26, 2023

Related U.S. Application Data

(62) Division of application No. 16/094,254, filed as application No. PCT/EP2017/060821 on May 5, 2017, now Pat. No. 11,434,265.

(30) Foreign Application Priority Data

May 5, 2016 (GB) ..................................... 1607901

(51) Int. Cl.
| C07K 14/33 | (2006.01) |
| C12N 9/52 | (2006.01) |
| A61K 38/00 | (2006.01) |

(52) U.S. Cl.
CPC ................ C07K 14/33 (2013.01); C12N 9/52 (2013.01); C12Y 304/24069 (2013.01); A61K 38/00 (2013.01); C07K 2319/55 (2013.01)

(58) Field of Classification Search
CPC ....................................................... C07K 14/33
See application file for complete search history.

(56) References Cited

U.S. PATENT DOCUMENTS

| 6,545,126 B1 | 4/2003 | Johnson et al. |
| 7,172,764 B2 | 2/2007 | Li et al. |
| 7,465,457 B2 | 12/2008 | Johnson et al. |
| 7,514,088 B2 | 4/2009 | Steward et al. |
| 9,598,685 B2 | 3/2017 | Dong et al. |
| 9,849,163 B2 | 12/2017 | Chaddock et al. |
| 9,920,310 B2 | 3/2018 | Anderson et al. |
| 10,190,110 B2 | 1/2019 | Dong et al. |
| 10,266,816 B2 | 4/2019 | Rummel et al. |
| 10,307,468 B2 | 6/2019 | Palan et al. |
| 10,329,543 B2 | 6/2019 | Ostertag et al. |
| 10,451,621 B2 | 10/2019 | Wang et al. |
| 10,457,927 B2 | 10/2019 | Dolly et al. |
| 10,501,731 B2 | 12/2019 | Steward et al. |
| 10,647,750 B2 | 5/2020 | Anderson et al. |
| 10,704,035 B2 | 7/2020 | Collier et al. |
| 10,709,772 B2 | 7/2020 | Caikos et al. |
| 10,786,438 B2 | 9/2020 | Krishnan et al. |
| 10,808,236 B2 | 10/2020 | Rummel |
| 10,844,362 B2 | 11/2020 | Dong et al. |
| 10,883,096 B2 | 1/2021 | Rummel et al. |
| 11,104,891 B2 | 8/2021 | Dong et al. |
| 11,117,935 B2 | 9/2021 | Dong et al. |
| 2012/0128649 A1 | 5/2012 | Chaddock et al. |
| 2014/0147429 A1 | 5/2014 | Chaddock et al. |
| 2016/0279208 A1 | 9/2016 | Chaddock et al. |
| 2018/0080016 A1 | 3/2018 | Dong et al. |
| 2018/0117128 A1 | 5/2018 | Palan et al. |
| 2019/0127427 A1 | 5/2019 | Liu |
| 2019/0185524 A1 | 6/2019 | Dong et al. |
| 2019/0201505 A1 | 7/2019 | Palan et al. |
| 2019/0256834 A1 | 8/2019 | Dong et al. |
| 2019/0300869 A1 | 10/2019 | Dong et al. |
| 2020/0224185 A9 | 7/2020 | Dong et al. |
| 2021/0040467 A1 | 2/2021 | Dong et al. |
| 2022/0033447 A1 | 2/2022 | Dong et al. |

FOREIGN PATENT DOCUMENTS

| WO | 2013180799 A1 | 12/2013 |
| WO | 2015097087 A1 | 7/2015 |
| WO | 2017191315 A1 | 11/2017 |

OTHER PUBLICATIONS

Wang et al., The FASEB Journal, 26:5035-5048 (2012).
International Search Report issued Aug. 1, 2017, in PCT/EP2017/060821.
Wang et al., Biochem J., 444:59-67 (2012).
Foster et al., Neurotoxicity Research, 9:101-107 (2006).
Gil et al., PLoS ONE, 8/7:e69692 (2013).
Rummel et al., FEBS Journal (2011), 278:4506-4515.

*Primary Examiner* — Albert M Navarro
(74) *Attorney, Agent, or Firm* — Gene J. Yao; Barnes & Thornburg LLP

(57) ABSTRACT

The present invention relates to chimeric neurotoxins with enhanced properties and their use in therapy.

20 Claims, 33 Drawing Sheets
Specification includes a Sequence Listing.

FIG. 1A

| | | |
|---|---|---|
| D_P19321 | ---MTWPVKDFNYSDPVNDNDILYLRIPQNKLITTPVKAFMITQNIWVIPERFSSD-TNPS | 57 |
| DC_AB745660 | ---MTWPVKDFNYSDPVNDNDILYLRIPQNKLITTPVKAFMITQNIWVIPERFSSD-TNPS | 57 |
| C1_P18640 | ---MPITNNFNYSDPVDNKNILYLDTHLNTLANEPEKAFRITGNIWVIPDRFSRN-SNPN | 57 |
| CD_AB200360 | ---MPITNNFNYSDPVDNKNILYLDTHLNTLANEPEKAFRIIGNIWVIPDRFSRD-SNPN | 57 |
| G_Q60393 | ---MPVNIKXFNYNDPINNDDIIMMEPFNDPGPGTYYKAFRIIDRIWVIPERFTYG-FQPD | 57 |
| B4_EF051570 | ---MPVTINNFNYNDPIDNDNIIMMEPPFARGTGRYYKAFKITDRIWIIPERYTFG-YKPE | 57 |
| B8_JQ964806 | ---MPVTINNFNYNDPIDNDNIIMMEPPFARGTGRYYKAFKITDRIWIIPERYTFG-YKPE | 57 |
| B7_JQ354985 | ---MPVTINNFNYNDPIDNNNIIMMEPPFARGTGRYYKAFKITDRIWIIPERYTFG-YKPE | 57 |
| B6_AB302852 | ---MPVTINNFNYNDPIDNNNIIMMEPPFARGTGRYYKAFKITDRIWIIPERYTFG-YKPE | 57 |
| B2_AB084152 | ---MPVTINNFNYNDPIDNNNIIMMEPPFARGTGRYYKAFKITDRIWIIPERYTFG-YKPE | 57 |
| B3_EF028400 | ---MPVTINNFNYNDPIDNNNIIMMEPPFARGTGRYYKAFKITDRIWIIPERYTFG-YKPE | 57 |
| B1_B1INP5 | ---MPVTINNFNYNDPIDNDNIIMMEPPFARGMGRYYKAFKITDRIWIIPERYTFG-YKPE | 57 |
| B5_EF033130 | ---MPVTINNFNYNDPIDNDNIIMMEPPFARGMGRYYKAFKIHNKVWVIPERDIFTNPEEV | 57 |
| A4_EU341307 | ---MPLVNQQINYDPVNGVDIAYIKIPNAGK-MQPVKAFKIHNKVWVIPERDIFTNPEEG | 57 |
| A7_JQ954969 | ---MPFVNKQFNYKDPVNGVDIAYIKIPNAGQ---MQPVKAFKIHNKIWVIPERDIFTNPEEG | 57 |
| A6_FJ981696 | ---MPFVNKQFNYKDPVNGVDIAYIKIPNAGQ---MQPVKAFKIHNKIWVIPERDIFTNPEEG | 57 |
| A1_A5HZZ9 | ---MPFVNKQFNYKDPVNGVDIAYIKIPNAGQ---MQPVKAFKIHNKIWVIPERDIFTNPEEG | 57 |
| A5_EU679004 | ---MLFVNKQFNYKDPVNGVDIAYIKIPNAGQ---MQPVKAFKIHNKIWVIPERDIFTNPEEG | 57 |
| A3_DQ185900 | ---MPFVNKPFNYRDPGNGVDIAYIKIPNAGQ---MQPVKAFKIHEGVWVIPERDIFTNPEEG | 57 |
| A2_X73423 | ---MPFVNKQFNYKDPVNGVDIAYIKIPNAGQ---MQPVKAFKIHNKIWVIPERDIFTNPKEG | 57 |
| A8_KM233166 | ---MPVVINSFNYDDPVNDTIYIRPPYYETSNTYFKAFQIMDNVWIIPERNVWIIPERNIWIIPERNTILYIKPG----GCQQFYKSFNIMKNIWIIPERNVIG-TIPQ | 53 |
| H_KG015617 | MLYMPKINSFNYNDPVNDKTILYIKPG----GCQQFYKSFNIMKNIWIIPERNVIG-TIPQ | 56 |
| E9_JX424534 | ---MPKYMPKINSFNYNDPVNDKTILYIKPG----GCQQFYKSFNIMKNIWIIPERNVIG-TIPQ | 53 |
| E12_KM370319 | ---MPKINSFNYNDPVNDKTILYIKPG----GCQQFYKSFNIMKNIWIIPERNVIG-TIPQ | 53 |
| E11_KF861875 | ---MPKINSFNYNDPVNDKTILYIKPG----GCQQFYKSFNIMKNIWIIPERNVIG-TIPQ | 53 |
| E10_KF861917 | ---MPKINSFNYNDPVNDKTILYIKPG----GCQQFYKSFNIMKNIWIIPERNVIG-TIPQ | 53 |
| E7_JN695729 | ---MPKINSFNYNDPVNDRTILYIKPG----GCQEFYKSFNIMKNIWIIPERNVIG-TIPQ | 53 |
| E8_JN695730 | ---MPKINSFNYNDPVNDRTILYIKPG----GCQEFYKSFNIMKNIWIIPERNVIG-TIPQ | 53 |
| E5_AB037711 | ---MPKINSFNYNDPVNDRTILYIKPG----GCQEFYKSFNIMKNIWIIPERNVIG-TIPQ | 53 |
| E6_AM695759 | ---MPTINSFNYNDPVNNRTILYIKPG----GCQEFYKSFNIMKNIWIIPERNVIG-TTPQ | 53 |
| E4_AB088207 | ---MPKINSFNYNDPVNDRTILYIKPG----GCQEFYKSFNIMKNIWIIPERNVIG-TIPQ | 53 |
| E3_EF028403 | ---MPKINSFNYNDPVNDRTILYIKPG----GCQEFYKSFNIMKNIWIIPERNVIG-TTPQ | 53 |
| E1_Q00496 | ---MPKINSFNYNDPVNDRTILYIKPG----GCQEFYKSFNIMKNIWIIPERNVIG-TTPQ | 53 |
| E2_EF028404 | ---MPVNINNFNYNDPINNTTILYMKMPYYEDSNKYYKAFEIMDNVWIIPERNIIG-KKPS | 57 |
| F7_GU213233 | ---MPVEINSFNYNDDLVNDNTILYIRPPYYERSNTYFKAFNIMENVWIIPERYRLG-IEAS | 57 |
| F5_GU213211 | ---MPVVINSFNYNDPVNDDTILYMQIPYEEKSKKYYKAFEIMRNVWIMPERNTIG-TDPS | 57 |
| F1_Q57236 | ---MPVVINSFNYNDDPVNDDTILYMQIPYEEKSKKYYKAFEIMRNVWIMPERNTIG-TNPS | 57 |
| F4_GU213214 | ---MPVVINSFNYNDPVNDETILYMQKPYEERSRKYYKAFEIMPNVWIMPERDTIG-TKPD | 57 |
| F2_GU213209 | ---MPVVINSFNYNDPVNDETILYMQKPYEERSRKYYKAFEIMPNVWIMPERDTIG-TKPD | 57 |
| F3_GU213227 | ---MPVAINSFNYNDPVNDTILYMQIPYEEKSRKYYKAFEIMRNVWIIPERNTIG-TNPS | 57 |
| F6_M92906 | ---MPITINNFRYSDPVNNDTIIMMEPPYYCKGLDIYYKAFKITDRIWIVPERYEFG-TKPE | 57 |
| T_P04958 | | |

FIG. 1B

```
D_P19321        LSKPPR-PT-SKYQSYYDPSYLSTDEQKDTFLKGIIKLFKRINERDIGKKLINYLVVGSP  115
DC_AB745660     LSKPPR-PT-SKYQSYYDPSYLSTDEQKDTFLKGIIKLFKRINERDIGKKLINYLVVGSP  115
C1_P18640       LNKPPR-VT-SPKSGYYDPNYLSTDSDKDTFLKEIIKLFKRINSREIGEELIYRLSTDIP  115
CD_AB200360     LNKPPR-VT-SPKSGYYDPNYLSTDSEKDTFLKEIIKLFKRINSREIGEELIYRLATDIP  115
G_Q60393        QFNASTGVFSKDVYEYYDPTYLKTDAEKDFLKIMIKLFNRINSKPSGQRLLDMIVDAIP   117
B4_EF051570     DFNKSSGIFNRDVCEYYDPDYLNTNDKKNIFLQTMIKLFNRINRIKSKPLGEKLLEMIINGIP 117
B8_JQ964806     DFNKSSGIFNRDVCEYYDPDYLNTNDKKNIFLQTMIKLFNRINRIKSKPLGEKLLEMIINGIP 117
B7_JQ354985     DFNKSSGIFNRDVCEYYDPDYLNTNDKKNIFLQTMIKLFNRINRIKSKPLGEKLLEMIINGIP 117
B6_AB302852     DFNKSSGIFNRDVCEYYDPDYLNTNDKKNIFLQTMIKLFNRINRIKSKPLGEKLLEMIINGIP 117
B2_AB084152     DFNKSSGIFNRDVCEYYDPDYLNTNDKKNIFLQTMIKLFNRINRIKSKPLGEKLLEMIINGIP 117
B3_EF028400     DFNKSSGIFNRDVCEYYDPDYLNTNDKKNIFLQTMIKLFNRINRIKSKPLGEKLLEMIINGIP 117
B1_B1INP5       DFNKSSGIFNRDVCEYYDPDYLNTNDKKNIFLQTMIKLFNRINRIKSKPLGEKLLEMIINGIP 117
B5_EF033130     DFNKSSGIFNRDVCEYYDPDYLNTNDKKNIFLQTMIKLFNRINRIKSKPLGEKLLEMIINGIP 117
A4_EU341307     DLNPPPEAK-QVPISYDSAYLSTDNEKDNYLKGVIKLFERIYSTDLGRMLLISIVRGIP   116
A7_JQ954969     DLNPPPEAK-QVPVSYYDSTYLSTDNEKDNYLKGVTKLFERIYSTDLGRMLLTSIVRGIP  116
A6_FJ981696     DLNPPPEAK-QVPVSYYDSTYLSTDNEKDNYLKGVTKLFERIYSTDLGRMLLTSIVRGIP  116
A1_A5HZZ9       DLNPPPEAK-QVPVSYYDSTYLSTDNEKDNYLKGVTKLFERIYSTELGRMLLTSIVRGIP  116
A5_EU679004     DLNPPPEAK-QVPVSYYDSTYLSTDNEKDNYLKGVTKLFDRIYSTGLGRMLLSFIVKGIP  116
A3_DQ185900     DLNPPPEAK-QVPVSYYDSTYLSTDNEKDNYLKGVTKLFERIYSTDLGRMLLTSIVRGIP  116
A2_X73423       DLNPPPEAK-QVPVSYYDSTYLSTDNEKDNYLKGVTKLFERIYSTDLGRMLLTSIVRGIP  116
A8_KM233166     LFNPPVSLK-AGSDGYFDPNYLSTNTEKNKVLQIMLFKRINSKPAGQILLEEIKNAIP   116
H_KG015617      NFLPPTSLK-NGDSSYYDPNYLQNDQEEKDRFLKIVTKVFNRIDNLSGRILLEELSKANP 112
E9_JX424534     DFQPPTSLK-NGDSSYYDPNYLQSNEEKDRFLKIVTKIFNRIDNLSGGILLEELSKANP  115
E12_KM370319    DFLPPTSLK-NGDSSYYDPNYLQSNEEKDRFLKIVTKIFNRIDNLSGGILLEELSKANP  112
E11_KF861875    DFLPPTSLK-NGDSSYYDPNYLQSNEEKDRFLKIVTKIFNRIDNLSGGILLEELSKANP  112
E10_KF861917    DFLPPTSLK-NGDSSYYDPNYLQSNEEKDRFLKIVTKIFNRIDNLSGGILLEELSKANP  112
E7_JN695729     DFLPPTSLK-NGDSSYYDPNYLQSNEEKDRFLKIVTKIFNRIDNLSGRILLEELSKANP  112
E8_JN695730     DFHPPTSLK-NGDSSYYDPNYLQSDEEKDRFLKIVTKIFNRINNNLSGGILLEELSKANP 112
E5_AB037711     DFHPPTSLK-NGDSSYYDPNYLQSYEEKDRFLKIVTKIFNRINNNLSGGILLEELSKANP 112
E6_AM695759     DFHPPTSLK-NGDSSYYDPNYLQSDQEKDKFLKIVTKIFNRINSNPAGQVLLEEIKNGKP 112
E4_AB088207     DFHPPTSLK-NGDSSYYDPNYLQSDEEKDRFLKIVTKIFNRINSNEAGKILLNQIKDAIP 115
E3_EF028403     DFLPPTSLK-NGDSSYYDPNYLQSNEEKDRFLKIVTKIFNRINSNPAGEVLLQEISYAKP 116
E1_Q00496       DFDPPASLE-NGSSAYYDPNYLTTDAEKDRYLKTTIKLFKRINSNPAGEVLLQEISYAKP 116
E2_EF028404     DFDPPASLK-NGSSAYYDPNYLTTDAEKDRYLKTMIKLFNRINPTGKVLLEEVSNARP  116
F7_GU213233     DFYPPISLD-SGSSAYYDPNYLTTDAEKDRYLKTMIKLFNRINSNPAGQVLLEEIKNGKP 116
F5_GU213211     KFDPPDSLK-AGSDGYFDPNYLSTNTEKNRYLKTMIKLFKRINSNEAGKILLNQIKDAIP 116
F1_Q57236       DFDPPASLK-NGSSAYYDPNYLTTDAEKDRYLKTTIKLFKRINSNPAGEVLLQEISYAKP 116
F4_GU213214     DFDPPASLK-NGSSAYYDPNYLTTDAEKDRYLKTMIKLFNRINPTGKVLLEEVSNARP  116
F2_GU213209     EFQVPDSLK-NGSSAYYDPNYLTTDAEKDRYLKTMIKLFNRINPTGKVLLEEVSNARP  116
F3_GU213227     DFQVPDSLK-NGSSAYYDPNYLTTDAEKDRYLKTMIKLFNRINSNPTGKVLLEEVSNARP 116
F6_M92906       DFDPPASLK-NGSSAYYDPNYLTTDAEKDRYLKTMIKLFKRINSNPAGKVLLQEISYAKP 116
T_P04958        DFNPPSSLI-EGASEYYDPNYLRTDSDKDRFLQIMVKLFNRIKNNVAGEALLDKIINAIP 116
```

FIG. 1C

```
D_P19321        FMGDSSTPEDTIFDFTRHTTNIAVEKFENGSWKVTNIITPSVLIFGPLPNILDYTASLTLQ    175
DC_AB745660     FMGDSSTPEDTIFDFTRHTTNIAVEKFENGSWKVTNIITPSVLIFGPLPNILDYTASLTLQ    175
C1_P18640       FPGNNNTPINTFDFDVDFNSVDVKTRQGNNWWVKIGSINPSVIITGPRENIIDPETSTFKL    175
CD_AB200360     FPGNNNTPINTFDFDVDFNSVDVKTRQGNNWWVKTGSINPSVIITGPRENIIDPETSTFKL    175
G_Q60393        YLGNASTPPDKFAANVANVSINKKIIQPGAEDQIKGLMTNLIIFGPGPVLSDNFTDSMIM     177
B4_EF051570     YLGDRRVPLEEFNTNIASVTVNKLISNPGEVEQKGIFANLIIFGPGPVLNENETIDIGI      177
B8_JQ964806     YLGDRRVPLEEFNTNIASVTVNKLISNPGGEERKEGIFANLIIFGPGPVLNENETIDIGI     177
B7_JQ354985     YLGDRRVPLEEFNTNIASVTVNKLISNPGEVERKKGIFANLIIFGPGPVLNENETIDIGI     177
B6_AB302852     YLGDRRVPLEEFNTNIASVTVNKLISNPGEVERKKGIFANLIIFGPGPVLNENETIDIGI     177
B2_AB084152     YLGDRRVPLEEFNTNIASVTVNKLISNPGEVERKKGIFANLIIFGPGPVLNENETIDIGI     177
B3_EF028400     YLGDRRVPLEEFNTNIASVTVNKLISNPGEVERKKGIFANLIIFGPGPVLNENETIDIGI     177
B1_B1INP5       YLGDRRVPLEEFNTNIASVTVNKLISNPGEVERKKGIFANLIIFGPGPVLNENETIDIGI     177
B5_EF033130     YLGDRRVPLEEFNTNIASVTVNKLISNPGEVERKKGIFANLIIFGPGPVLNENETIDIGI     177
A4_EU341307     FWGGKIDTE--LKVIDTNCINIIQLDD------SYRSEELNLAIIGPSANIIESQCSSFR-    169
A7_JQ954969     FWGGSTIDTE--LKVIDTNCINVIQPDG-----SYRSEELNLVIIGPSADIINFECKSFG-    169
A6_FJ981696     FWGGSTIDTE--LKVIDTNCINVIQPDG-----SYRSEELNLVIIGPSADIIQFECKSFG-    169
A1_A5HZ29       FWGGSTIDTE--LKVIDTNCINVIQPDG-----SYRSEELNLVIIGPSADIIQFECKSFG-    169
A5_EU679004     FWGGSTIDTE--LKVIDTNCINVIQPDG-----SYRSEELNLVIIGPSADIIQFECKSFG-    169
A3_DQ185900     FWGGSTIDTE--LKVIDTNCINVIEPGG-----SYRSEELNLVIIGPSADIIQFECKSFG-    169
A2_X73423       FWGGSTIDTE--LKVIDTNCINVIQPDG-----SYRSEELNLVIIGPSADIIQFECKSFG-    169
A8_KM233166     YLGNSYTQEEQFTTNNRTVSFNVKLANG-----NIVQQMANLIIWGPGPDLTTNKTGGIIY    172
H_KG015617      YLGNDNTRDDDFIIN-DGSAVPIQFSNG-----SQSILLPTVIIMGAEPDLFETNSSNVSL    167
E9_JX424534     YLGNDNTPDGDFIIN-DASAVPIQFSNG-----SQSILLPNVIIMGAEPDLFETNSSNISL    170
E12_KM370319    YLGNDNTPNNQFHIG-DASAVEIKFSNG-----SQSILLPTVIIMGAEPDLFETNSSNISL    167
E11_KF861875    YLGNDNTPMNQFHIG-DASAVEIKFSNG-----SQSILLPTVIIMGAEPDLFETNSSNISL    167
E10_KF861917    YLGNDNTPDNQFHIG-DASAVEIKFSNG-----NQSILLPNVIIMGAEPDLFETNSSNISL    167
E7_JN695729     YLGNDNTPDNQFHIG-DASAVEIKFSNG-----NQSILLPNVIIMGAEPDLFETNSSNISL    167
E8_JN695730     YLGNDNTPDNQFHIG-DASAVEIKFSNG-----SQDILLPNVIIMGAEPDLFETNSSNISL    167
E5_AB037711     YLGNDNTPDNQFHIG-DASAVEIKFSNG-----SQDILLPNVIIMGAEPDLFETNSSNISL    167
E6_AM695759     YLGNDNTPDNQFHIG-DASAVEIKFSNG-----SQDILLPNVIIMGAEPDLFETNSSNISL    167
E4_AB088207     YLGNDNTPDGDFIIN-DASAVPIQFSNG-----SQHILLPNVIIMGAEPDLFETNSSNISL    167
E3_EF028403     YLGNDNTPDNQFHIG-DASAVEIKFSNG-----SQDILLPNVIIMGAEPDLFETNSSNISL    167
E1_Q00496       YLGNDNTPDNQFHIG-DASAVEIKFSNG-----IQDILLPNVIIMGAEPDLFETNSSNISL    167
E2_EF028404     YLGNDHTAVNEFCANNRSTSVEIKESNG-----TTDSMLLNLIVILGPNILECSTFPVRI    167
F7_GU213233     YLGNSYTAEDQFTTNNRTISFNVRLANG-----TIEQEMANLIIWGPGPDLTTNRTGGTTY    172
F5_GU213211     YLGNEHTPINEEHPVTRTTSVNIKSSTN------VKSSIINLLVLGAGPDIFENSSYPVRK    172
F1_Q57236       YLGNDHTPINEFHPVTRTTSVNIKSSTN------VESSIILNLLVLGAGPNIFENSSYPVRK   172
F4_GU213214     YLGDDTLINEFFPVNVTTSVNIKFSTD------VESSIISNLLVLGAGPDIFKAYCTPLVR    172
F2_GU213209     YLGDDDTLINEFFPVNVTTSVNIKFSTD-----VESSIISNLLVLGAGPDIFKAYCTPLVR    172
F3_GU213227     YLGDDTLINEFFPVNVTTSVNIKLSTN------VESSMLLNLLVLGAGPDIFESCCYPVRK    172
F6_M92906       YLGNSYSLLDKFDTNSNSVSFNLLEQDPSGATTIKSAMLTNLIIFGPGPVLNKNEVRGIVL   176
```

| | | |
|---|---|---|
| D_P19321 | KNNRLPYVADKDSISQE-IFENKIITDETNVQNYSDKF----SLDESILDGQVPINPEIVD | 509 |
| DC_AB745660 | KNNTLPYVADKDSISQE-IFESQIITDETNVENYSDNF----SLDESILDAKVPTNFEAVD | 509 |
| C1_P18640 | KNTDLPFIGDISDVKTD-IFLRKDINEETEVIYYPDNV---SVDQVILSKNTS-EHGQLD | 513 |
| CD_AB200360 | KNTDLPFIGDISDIKTD-IFLSKDINEETEVIDYPDNV---SVDQVILSKNTS-EHGQLD | 513 |
| G_Q60393 | NNEDLFFIANKDSFSKD-LAKAETIAYNTQNNTIENNF----SIDQLILDNDLSSGID-L- | 507 |
| B4_EF051570 | DNENLFFIADKNSFSDD-LSKNERVEYNIQNNYIGNDF----PINELILDTDLISKIE-L- | 503 |
| B8_JQ964806 | DNEDLFFIADKNSFSDD-LSKNERIEYNTQSNYIENDF----SINELILDTDLISKIE-L- | 503 |
| B7_JQ354985 | DNEDLFFIADKNSFSDD-LSKNERIEYNIKNIYIENYF----SINELILDTDLISGIE-L- | 503 |
| B6_AB302852 | DNEDLFFIADKNSFSDD-LSKNERIEYDTQSNYIENRS----SIDELILDTNLISKIE-L- | 503 |
| B2_AB084152 | DNEDLFFIADKNSFSDD-LSKNERIEYDTQSNYIENRS----SIDELILDTNLISKIE-L- | 503 |
| B3_EF028400 | DNEDLFFIADKNSFSDD-LSKNERIEYDTQSNYIENRS----SIDELILDTNLISKIE-L- | 503 |
| B1_B1INP5 | DNEDLFFIADKNSFSDD-LSKNERIEYNTQSNYIENDF----PINELILDTDLISKIE-L- | 503 |
| B5_EF033130 | DNEDLFFIADKNSFSDD-LSKNERIAYNIQNNYIENDF----SINELILDTDLISKIE-L- | 503 |
| A4_EU341307 | NNWDLFFSPSEDNFTND-LDKVEEITSDTNIEAAEENISLDLIQQYYLNFNDNEPENT- | 515 |
| A7_JQ954969 | NNWDLFFSPSEDNFTND-LNKGEEITSDTNIEAAEENISSDLIQQYYLITFNFDNEPENI- | 515 |
| A6_FJ981696 | NNWDLFFSPSEDNFTND-LNKGEEITSDTNIEAAEENISLDLIQQYYLITFNFDNEPENI- | 515 |
| A1_A5HZZ9 | NNWDLFFSPSEDNFTND-LNKGEEITSDTNIEAAEENISLDLIQQYYLITFNFDNEPENI- | 515 |
| A5_EU679004 | NNWDLFFSFSEDNFTND-LNKGEEITSDTNIEAAEENISLDLIQQYYLITFNFDNEPENI- | 515 |
| A3_DQ185900 | NNWDLFFSPSEDNFTND-LDKVEEITADTNIEAAEENISLDLIQQYYLTFDFDNEPENI- | 511 |
| A2_X73423 | NNWDLFFSPSEDNFTND-LDKVEEITADTNIEAAEENISLDLIQQYYLTFDFDNEPENI- | 515 |
| A8_KM233166 | NNWDLFFSPSEDNFTND-LDKVEEITSDTNIEAAEENISLDLIQQYYLTFDFDNEPENI- | 515 |
| H_KGO15617 | NNRDLFFIASQESYGENTINTYKEIDDTTTLDPSFEDILD----KVILNFNEQVIPQ-M- | 495 |
| E9_JX424534 | NNGELFFVASEKSYNNDSINIPKEINTPKEIDDTVTLNNNYENDLD----QVILNFNSESAPG-L- | 483 |
| E12_KM370319 | NNGELFFVASENSYNDDNINTPKEIDDTVTSNNNYENDLD----QVILNFNSESAPG-L- | 486 |
| E11_KF861875 | NNGELFFVASENSYNDDNINTSKEIDDTVTSNNNYENDLD----QVILNFNSESAPG-L- | 483 |
| E10_KF861917 | NNGELFFVASENSYNDDNINTPKEIDDTVTSNNNYENDLD----QVILNFNSESAPG-L- | 483 |
| E7_JN695729 | NNGELFFVASENSYNDDNINTPKEIDDTVTSNNNYENDLD----QVILNFNSESAPG-L- | 483 |
| E8_JN695730 | NNGELFFVASENSYNDDNINTPKEIDDTVTSNNNYENDLD----QVILNFNSESAPG-L- | 483 |
| E5_AB037711 | NNGELFFVASENSYNDDNINTPKEIDDTVTSNNNYENDLD----QVILNFNSESAPG-L- | 483 |
| E6_AM695759 | NNGELFFVASDNSYNDDNINTPKEIDDTVTSNNNYENDLD----QVILNFNSESAPG-L- | 483 |
| E4_AB088207 | NNGELFFVASENSYNDDNINTPKEIDDTVTSNNNYENDLD----QVILNFNSESAPG-L- | 483 |
| E3_EF028403 | NNGELFFVASENSYNDDNINTPKEIDDTVTSNNNYENDLD----QVILNFNSESAPG-L- | 483 |
| E1_Q00496 | NNGELFFVASENSYNDDNINTPKEIDDTVTSNNNYENDLD----QVILNFNSESAPG-L- | 483 |
| E2_EF028404 | NNRDLFFVASENSYNDDNINTPKEIDDTITNNNYKKNLD----QVILNFNSDAIPN-L- | 492 |
| F7_GU213233 | NNGDLFFIASEDSYGEDTINTPKEIDDTTLVPSFKNILD----KVILDFNKQVTPQ-I- | 499 |
| F5_GU213211 | NNRELFFVASESSYNENDINTPKEIDDTTNLNNNYRMNLD----EVILDYNSETIPQ-I- | 502 |
| F1_Q57236 | NNRELFFVASESSYNENDINTPKEIDDTTNLNNNYRNNLD----EVILDYNSETIPQ-I- | 502 |
| F4_GU213214 | NNRELFFVASESSYNESDINTPKEIDDTTNLNNNYRNNLD----EVILDYNSETIPQ-I- | 502 |
| F2_GU213209 | NNRELFFVASESSYNESDINTPKEIDDTTNLNNNYRNNLD----EVILDYNSETIPQ-I- | 502 |
| F3_GU213227 | NNSELFFVASESSYNENDINTPKEIDDTTNLNNNYRNNLD----EVILDYNSQTIPQ-I- | 502 |
| F6_M92906 | KNEDLTFIAEKNSFSEE-PFQDEIVSYNTKNKPLNFNY----SLDKIIVDYNLQSKIT-L- | 524 |
| T_P04958 | | |

FIG. 1J

```
D_P19321       PLLPNVNMEPL-------NLPGEEI-VFYDDITKYVD-YLNSYYYLESQKLSNNVENITLT           561
DC_AB745660    PLLPNVNMEPL-------NVPGEEE-VFYDDITKDVD-YLNSYYYLEAQKLSNNVENITLT           561
C1_P18640      LLYPSIDSESE-------ILPGENQ-VFYDNRTQNVD-YLNSYYYLESQKLSDNVEDFFT            565
CD_AB2003360   LLYPIIEGESQ-------VLPGENQ-VFYDNRTQNVD-YLNSYYYLESQKLSDNVEDFFT            565
G_Q60393       -PNENTEPFTNFDDIDIPVYIK--QSALKKIFVD-GDSLFEYLHAQTFPSNIENLQLT             561
B4_EF051570    -PSENTESLIDFN-VDVPVYEK--QPAIKKVFTD-ENTIFQYLYSQTFPLNIRDISLI              556
B8_JQ964806    -PSENTESLIDFN-VDVPVYEK--QPAIKKIFTD-ENTIFQYLYSQTFPLDIRDISLI              556
B7_JQ354985    -PSENTESLIDFN-VDVPVYEK--QPAIKKIFTD-ENTIFQYLYSQTFPLDIRDISLI              556
B6_AB302852    -PSENTESLIDFN-VDVPVYEK--QPAIKKFFTD-ENTIFQYLYSQTFPLDIRDISLI              556
B2_AB084152    -PSENTESLIDFN-VDVPVYEK--QPAIKKIFTD-ENTIFQYLYSQTFPLDIRDISLI              556
B3_EF028400    -PSENTESLIDFN-VDVPVYEK--QPAIKKIFTD-ENTIFQYLYSQTFPLDIRDISLI              556
B1_B1INP5      -PSENTESLIDFN-VDVPVYEK--QPAIKKIFTD-ENTIFQYLYSQTFPLDIRDISLI              556
B5_EF033130    -PSENTESLIDFN-VYVPVYKK--QPAIKKIFTD-ENTIFQYLYSQTFPLDIRDISLI              556
A4_EU341307    -SIENLSSD-IIG-QLEPMPNIERFPNGKKYELN-KYTMFHYLRAQEFKHSNSRIILI              569
A7_JQ954969    -SIENLSSD-IIG-QLELMPNIERFPNGKKYELD-KYTMFHYLRAQEFEYGNSRIVLI              569
A6_FJ981696    -SIENLSSD-IIG-QLELMPNIERFPNGKKYELD-KYTMFHYLSAQEFEHGKSRIDLI              569
A1_A5HZ29      -SIENLSSD-IIG-QLELMPNIERFPNGKKYELD-KYTMFHYLRAQEFEHGKSRIALI              569
A5_EU679004    -SIENLSSD-IIG-QLELMPNIERFPNGKKYELD-KYTMFHYLRAQEFEHGKSRIVLI              569
A3_DQ185900    -SIENLSSD-IIG-QLEPMPNIERFPNGKKYELD-KYTMFHYLRAQEFEHGDSRIILI              565
A2_X73423      -SIENLSSD-IIG-QLEPMPNIERFPNGKKYELD-KYTMFHYLRAQEFEHGDSRIILI              569
A8_KM233166    -SIENLSSD-IIG-QLEPMPNIERFPNGKKYELD-KYTMFHYLRAQEFEHSKSRIALI              569
H_KGO15617     -PNRNVSTD-IQKDNYIPKYDYNRTDIIDSYEVGRNYNTFFYLNAQKFSPNESNITLI              551
E9_JX424534    -SDKKLNIS-IQDDVYIPKYDYNRTDIIDSYEVGRNYNTFFYLNAQKFSPNESNITLI              538
E12_KM370319   -SDKLNLT-IQDDAYIPKYDYNRTDIIDSYEVGRNYNTFFYLDAQKVPEGENNVDFT                541
E11_KF861875   -SDKLNLT-IQDDAYIPKYDYNRTDIIDSYEVGRNYNTFFYLDAQKVPEGENNVDFT                538
E10_KF861917   -SDKLNLT-IQDDAYIPKYDYNRTDIIDSYEVGRNYNTFFYLDAQKVPEGENNVNLI                538
E7_JN695729    -SDKLNLT-IQNDAYIPKYDYNRTDIIDSYEVGRNYNTFFYLDAQKVPEGENNVNLI                538
E8_JN695730    -SDKLNLT-IQNDAYIPKYDYNRTDIIDSYEVGRNYNTFFYLDAQKVPEGENNVNLI                538
E5_AB037711    -SDKLNLT-IQNDAYIPKYDYNRTDIIDSYEVGRNYNTFFYLDAQKVPEGENNVNLI                538
E6_AM695759    -SDKLNLT-IQNDAYIPKYDYNRTDIIDSYEVGRNYNTFFYLDAQKVPEGENNVNLI                538
E4_AB088207    -SDKLNLT-IQNDAYIPKYDYNRTDIIDSYEVGRNYNTFFYLDAQKVPEGENNIDFT                538
E3_EF028403    -SDKLNLT-IQNDAYIPKYDYNRTDIIDSYEVGRNYNTFFYLDAQKVPEGENNVNLI                538
E1_Q00496      -SDKLNLT-IQNDAYIPKYDYNRTDIIDSYEVGRNYNTFFYLDAQKVPEGENNVNLI                538
E2_EF028404    -SDKLNLT-IQNDAYIPKYDYNRTDIIDSYEVGRNYNTFFYLDAQKVPEGENNVNLI                538
F7_GU213233    -SSRLNTT-AQNDSYVPKYDYNRTDIIDSYEIKEYTVD-KLNVFFYLYAQKAPEGESAISLI           547
F5_GU213211    -PNRRIRTD-IQEDNYIPEYDYNRTDIIDSYEIEEYNVV-DLNAFFYLHAQKVPEGETNISLI          554
F1_Q57236      -SNQTLNTL-VQDDSYVPRYDYNRTDIIDSYEIEEHNVV-DLNVFFYLHAQKVPEGETNISLI          557
F4_GU213214    -SSQTLNTL-VQDDSYVPRYDYNRTDIIDSYEIEEHNVV-DLNVFFYLHAQKVPEGETNISLI          557
F2_GU213209    -SNRTLNTL-VQDNSYVPRYDYNRTDIIDSYEIEEYDVV-DFNVFFYLHAQKVPEGETNISLI          557
F3_GU213227    -SNRTLNTL-VQDNSYVPRYDYNRTDIIDSYEIEEYDVV-DFNVFFYLHAQKVPEGETNISLI          557
F6_M92906      -PNDRTTPVTKGIP-YAPFEYKSNAASTIEIHNID-DNTIYQYLYAQKSPTTLQRITMT              579
T_P04958
```

FIG. 1K

| ID | Sequence | Pos |
|---|---|---|
| D_P19321 | TSVEEALGYSNKKIYTFLPSLA-EKVNKGVQAGLFLNWANEVVEDFTTNIMKKDTLDKISD | 620 |
| DC_AB745660 | TSVEEALGYSNKKIYTFLPSLA-EKVNKGVQAGLFLNWANEVVEDFTTNIMKKDTLDKISD | 620 |
| C1_P18640 | RSIEEALDNSAKVYTYFPTLA-NKVNAGVQGGLFLMWANDVVEDFTTNILRKDTLDKISD | 624 |
| CD_AB200360 | TSIEEALDNSGKVYTYFPKLA-DKVNTGVQGGLFLMWANDVVEDFTTNILRKDTLDKISD | 624 |
| G_Q60393 | NSLNDALRNNNKVYTFFSINLVEKANTVVGASLFVNWVKGVIDDFTSESTQKSTIDKVSD | 621 |
| B4_EF051570 | SSFDDALLVSSKVYSFFSMDYIKTANKVVEAGLFAGWVKQIVDDFVIEANKSSTMDKIAD | 616 |
| B8_JQ964806 | SSFDDALLFSNKVYSFFSMDYIKTANKVVEAGLFAGWVKQIVDDFVIEANKSNTMDKIAD | 616 |
| B7_JQ354985 | SSFDDALLFSNKVYSFFSMDYIKTANKVVEAGLFAGWVKQIIDDFVIEANKSNTMDKIAD | 616 |
| B6_AB302852 | SSFDDALLFSNKVYSFFSMDYIKTANKVVEAGLFAGWVKQIVDDFVIEANKSSTMDKLAD | 616 |
| B2_AB084152 | SSFDDALLFSNKVYSFFSMDYIKTANKVVEAGLFAGWVKQIVDDFVIEANKSSTMDKIAD | 616 |
| B3_EF028400 | SSFDDALLFSNKVYSFFSMDYIKTANKVVEAGLFAGWVKQIVDDFVIEANKSSTMDKIAD | 616 |
| B1_B1INP5 | SSFDDALLFSNKVYSFFSMDYIKTANKVVEAGLFAGWVKQIVDDFVIEANKSNTMDKIAD | 616 |
| B5_EF033130 | SSFDDALLFSNKVYSFFSMDYIKTANKVVEAGLFAGWVKQIVDDFVIEANKSSTMDKIAD | 616 |
| A4_EU341307 | NSAKEALLKPNIVYTFFSSKYIKAINKAVEAVTFVNWIENLVYDFTDETNEVSTMDKIAD | 629 |
| A7_JQ954969 | NSVNEALLNPEALLKPNIVYTFFSSDYVKKANEATEAAMFLGWVEQLIYDFTDETSEVSTMDKIAD | 629 |
| A6_FJ981696 | NSVNEALLNPSHVYTFFSSDYVKKVNKATEAAMFLGWVEQLIYDFTDETSEVSTTDKIAD | 629 |
| A1_A5HZZ9 | NSVNEALLNPSRVYTFFSSDYVKKVNKATEAAMFLGWVEQLIYDFTDETSEVSTTDKIAD | 629 |
| A5_EU679004 | NSAEEALLKPNVAYTFFSSKYVKKINKAVEAVIFLSWAEELIYDFTDETSEVTTMDKIAD | 625 |
| A3_DQ185900 | NSAEEALLKPNVAYTFFSSKYVKKINKAVEVTFVNWIENATDDFTDETNEVTTMDKIAD | 629 |
| A2_X73423 | NSAEEALLKPNVAYTFFSSKYVKKINKAVEAFMFLNWAEELIYDFTDETSEVSTTDKIAD | 629 |
| A8_KM233166 | NSVNEALLNPSRVYTFFSSDYVKKVNKATEAAMFLGWVEQLIYDFTDETSEVSTTDKIAD | 629 |
| H_KGO15617 | SSFDTGLLEGSKIYTFFSSDFINNINKPVQALLFIEWVKQVIRDFTTEATKTSTVDKLKD | 611 |
| E9_JX424534 | SSIDTALLEQPKIYTFFSSEFINNVNKPVQAALFVGWIQQVIQQVLVDFTTEATQKSTVDKIAD | 598 |
| E12_KM370319 | SSIDTALLEQPKIYTFFSSEFISNLNKTMQAALFVSWIQQVLVDFTTEATQKSTVDKIAD | 601 |
| E11_KF861875 | SSIDTALLEQPKIYTFFSSKFISNLNKTMQAALFVSWIQQVLVDFTTEATQKSTVDKIAD | 598 |
| E10_KF861917 | SSIDTALLEQPKIYTFFSSEFINNVNKPVQAALFVSWIQQVLVDFTTEATQKSTVDKIAD | 598 |
| E7_JN695729 | SSIDTALLEQPKIYTFFSSEFINNVNKPVQAALFVSWIQQVLVDFTTEANQKSTVDKIAD | 598 |
| E8_JN695730 | SSIDTALLEQPKIYTFFSSEFINNVNKTVQAALFVSWIQQVLVDFTTEANQKSTVDKIAD | 598 |
| E5_AB037711 | SSIDTALLEQPKIYTFFSSEFINNVNKPVQAALFVSWIQQVLVDFTTEANQKSTVDKIAD | 598 |
| E6_AM695759 | SSIDTALLEQPKIYTFFSSEFINNVNKPVQAALFISWIQQVINDFTTEATQKSTIDKIAD | 598 |
| E4_AB088207 | SSIDTALLEQPKIYTFFSSEFINNVNKPVQAALFISWIQQVINDFTTEATQKSTIDKIAD | 598 |
| E3_EF028403 | SSIDTALLEQPKIYTFFSSEFINNVNKPVQAALFVSWIQQVINDFTTEATQKSTIDKIAD | 598 |
| E1_Q00496 | SSIDTALLEQPKIYTFFSSEFINNVNKPVQAALFVSWIQQVINDFTTEATQKSTIDKIAD | 598 |
| E2_EF028404 | SSIDTALLEQPKIYTFFSSEFINTVNKPVQAALFVSWIQQVINDFTTEATQKSTIDKIAD | 598 |
| F7_GU213233 | SSVNTALLDASKVYTFFSSDFINTVNKPVQAALFVSWIQQVINDFTTEATQKSTIDKIAD | 607 |
| F5_GU213211 | SSIDTALSEESKVYTFFSSEFIDTINEPVNAALFIDWISKVIRDFTTEATQKSTFDKIAD | 614 |
| F1_Q57236 | SSIDTALSEESQVYTFFSSEFINTINKPVHAALFISWINQVIRDFTTEATQKSTFDKIAD | 617 |
| F4_GU213214 | SSIDTALSEESKVYTFFSSEFINNINKPVHAALFIGWIKQVIRDFTTEATQKSTFDKIAD | 617 |
| F2_GU213209 | SSIDTALLEESKVYTFFSSEFIDTINKPVNAALFIDWINKVIRDFTTEATQKSTVDKIAD | 617 |
| F3_GU213227 | SSIDTALLEKSKVYTFFSSEFIDTINESVNAALFIDWISKVIRDFTTEATQKSTVDKIAD | 617 |
| F6_M92906 | SSIDTALLEESKVYTFFSSEFIDTINKPVNAALFIDWISKVIRDFTTEATQKSTVDKIAD | 616 |
| T_P04958 | NSVDDALINSTKIYSYFPSVI-SKVNQGAQGILFLQWVRDIIDDFTNESSQKTTIDKISD | 638 |

FIG. 1L

| | | |
|---|---|---|
| D_P19321 | VSVIIPYIGPALNIGNSALRGNFNQAFATAGVVAFLLEGFPEFTIPALGVFTFYSSIQ---- | 677 |
| DC_AB745660 | VSAIIPYIGPALNIGNSALRGNFKQAFATAGVAFLLEGFPEFTIPALGVFTFYSSIQ---- | 677 |
| C1_P18640 | VSAIIPYIGPALNISNSVRRGNFTEAFAVTGVTILLEAFPEFTIPALGAFVIYSKVQ---- | 681 |
| CD_AB200360 | VSAIIPYIGPALNISNSVRRGNFTEAFAVTGVTILLEAFQEFTIPALGAFVIYSKVQ---- | 681 |
| G_Q60393 | VSIIIPYIGPALNVGNFTAKENFKNAFEIGGAAILMEFIPELIVPIVGFFTLLESYVG---- | 678 |
| B4_EF051570 | ISLIVPYIGLALNVGDETAKGNFESAFEIAGSSILLEFIPELLIPVVGVFLLESYID---- | 673 |
| B8_JQ964806 | ISLIVPYIGLALNVGNETAKGNFENAFEIAGSSILLEFIPELLIPVVGAFLLESYID---- | 673 |
| B7_JQ354985 | ISLIVPYIGLALNVGNETAKGNFENAFEIAGASILLEFIPELLIPVVGAFLLESYID---- | 673 |
| B6_AB302852 | ISLIVPYIGLALNVGNETAKGNFENAFEIAGASILLEFIPELLIPVVGAFLLESYID---- | 673 |
| B2_AB084152 | ISLIVPYIGLALNVGNETAKGNFENAFEIAGASILLEFIPELLIPVVGAFLLESYID---- | 673 |
| B3_EF028400 | ISLIVPYIGLALNVGNETAKGNFENAFEIAGASILLEFIPELLIPVVGAFLLESYID---- | 673 |
| B1_B1INP5 | ISLIVPYIGLALNVGNETAKGNFENAFEIAGASILLEFIPELLIPVVGAFLLESYID---- | 673 |
| B5_EF033130 | ISLIVPYIGLALNIGNMIYKGEFVEAIIFSGAVILLEIVPEIALPVLGTFALVSYVS---- | 673 |
| A4_EU341307 | ITIVPYIGPALNIGNMIYKGEFVEAIIFSGAVILLEIVPEIVLLEFVPEIVLPILGTFALVSYTS---- | 686 |
| A7_JQ954969 | ITIVPYIGPALNIGNMVYKKKFEEALIFSGALIFSGAVILLEFIPEIAIPVLGTFAIVSYIA---- | 686 |
| A6_FJ981696 | ITIIPYIGPALNIGNMLYKDDFVGALIFSGAVILLEFIPEIAIPVLGTFAIVSYIA---- | 686 |
| A1_A5HZZ9 | ITIIPYIGPALNIGNMLYKDDFVGALIFSGAVILLEFIPEIAIPVLGTFAIVSYIA---- | 686 |
| A5_EU679004 | ITIIPYIGPALNIGNMLYKDDFVGALIFSGAVILLEFIPEIAIPVLGTFAIVSYIA---- | 686 |
| A3_DQ185900 | ITIIVPYIGPALNIGNMVSKGEFVEAIIFTGVVALLEFIPEYSLPVFGTFAIVSYIA---- | 682 |
| A2_X73423 | ITIIVPYIGPALNIGNMLSKGEFVEAIIFTGVVAMLEFIPEIAIPVLGTFAIVSYIA---- | 686 |
| A8_KM233166 | ITIIVPYIGPALNIGDEIYKQHFAEAVELVGAGLLLEFSPEFLIPTLLIFTIKGYLTGSI | 686 |
| H_KG015617 | ISIVVPYIGLALNIGNESQKGNFKDALELLGAGILLEAGILLGAILEFVPELLIPTILVFTILVFTIKSFLG--SS | 671 |
| E9_JX424534 | ISIVVPYIGLALNIGNEAQKGNFKDALELLGAGILLGAGILLGAGILEFVPELLIPTILVFTILVFTIKSFLG--SS | 657 |
| E12_KM370319 | ISIVVPYIGLALNIGNEAQKGNFKDALELLGAGILLGAGILEFVPELLIPTILVFTILVFTIKSFLG--SS | 660 |
| E11_KF861875 | ISIVVPYIGLALNIGNEAQKGNFKDALELLGAGILLGAGILEFEPELLIPILIVLVFTILVFTIKSFLG--SS | 657 |
| E10_KF861917 | ISIVVPYIGLALNIGNEAQKGNFKDALELLGAGILLGAGILEFEPELLIPTILVFTILVFTIKSFLG--SS | 657 |
| E7_JN695729 | ISIVVPYIGLALNIGNEAQKGNFKDALELLGAGILLGAGILEFEPELLIPTILVFTILVFTIKSFLG--SS | 657 |
| E8_JN695730 | ISIVVPYIGLALNIGNEAQKGNFKDALELLGAGILLGAGILEFEPELLIPTILVFTILVFTIKSFLG--SS | 657 |
| E5_AB037711 | ISIVVPYIGLALNIGNEAQKGNFKDALELLGAGILLGAGILEFEPELLIPTILVFTILVFTIKSFLG--SS | 657 |
| E6_AM695759 | ISIVVPYIGLALNIGNEAQKGNFKDALELLGAGILLGAGILEFEPELLIPTILVFTILVFTIKSFLG--SS | 657 |
| E4_AB088207 | ISIVVPYIGLALNIGNEAQKGNFKDALELLGAGILLGAGILEFEPELLIPTILVFTILVFTIKSFLG--SS | 657 |
| E3_EF028403 | ISIVVPYIGLALNIGNEAQKGNFKDALELLGAGILLGAGILEFEPELLIPTILVFTILVFTIKSFLG--SS | 657 |
| E1_Q00496 | ISIVVPYIGLALNIGNEAQKGNFKDALELLGAGILLGAGILEFEPELLIPTILVFTILVFTIKSFLG--SS | 657 |
| E2_EF028404 | ISIVVPYIGLALNIGNEVQKGNFKEAIELLGAGILLGAGILEFEPELLIPTILVFTILVFTIKSFIN--SD | 666 |
| F7_GU213233 | ISLIVPYVGLALNIVNETEKGNFKEAFELLGAGILLGAGILEFVPELAIPVILVFTILVFTIKSFIG--SY | 673 |
| F5_GU213211 | ISLIVPYVGLALNIGNEVQKENFKEAFELLGAGILLGAAILEVVPELLIPVILVFTILVFTIKSFIG--SS | 676 |
| F1_Q57236 | ISLIVPYVGLALNIGNDARKGNFKEAFELLGAGILLGAAILEVVPELLIPVILVFTILVFTIKSFID--SS | 676 |
| F4_GU213214 | ISLIVPYVGLALNIVIEAEKGNFEEEAFELLGAGILLGVGILEFVPELTIPVILVFTILVFTIKSYID--SY | 676 |
| F2_GU213209 | ISLIVPYVGLALNIVIDAEKGNFQEAFELLGAGILLGVGILEFVPELTIPVILVFTILVFTIKSYID--SY | 676 |
| F3_GU213227 | ISLIVPYVGLALNIIIEAEKGNFEEAFELLGVGILLEYIPEITLPVIAALSIAESST---- | 675 |
| F6_M92906 | VSTIVPYIGPALNIVKQGYEGNFIGALETTGVLLEYIPEITLPVIAALSIAESST---- | 695 |
| T_P04958 | | |

FIG. 1M

```
D_P19321        -EREKIIKTIENCLEQRVKRWKDSYQWMVSNWLSRITTQFNHINYQMYDSLSYQADAIKA  736
DC_AB745660     -EREKIIKTIENCLEQRVKRWKDSYQWMVSNWLSRITTQFNHISYQMYDSLSYQADAIKA  736
C1_P18640       -ERNEIIKTIDNCLEQRIKRWKDSYEWMMGTWLSRIITQFNNISYQMYDSLNYQAGAIKA  740
CD_AB2003360    -ERNEIIKTIDNCLEQRIKRWKDSYEWMIGTWLSRIITQFNNISYQMYDSLNYQADAIKD  740
G_Q60393        -NKGHIMTISNALKKRDQKWTDMYGLIVSQWLSTVNTQFYTIKERMYNALNNQSQAIEK   737
B4_EF051570     -NKNKIIKTIDNALITKRVEKWIDMYGLIVAQWLSTVNTQFYTIKEGMYKALNYQAQALEE 732
B8_JQ964806     -NKNKIIKTIDNALITKRDEKWIDMYGLIVAQWLSTVNTQFYTIKEGMYKALNYQAQALEE 732
B7_JQ354985     -NKNKIIKTIDNALITKRVEKWIDMYGLIVAQWLSTVNTQFYTIKEGMYKALNYQAQALEE 732
B6_AB302852     -NKNKIIKTIDNALITKRDEKWRDMYGLIVAQWLSTVNTQFYTIKEGMYKALNYQAQALEE 732
B2_AB084152     -NKNKIIKTIDNALITKRDEKWIDMYGLIVAQWLSTVNTQFYTIKEGMYKALNYQAQALEE 732
B3_EF028400     -NKNKIIKTIDNALITKRDEKWIDMYGLIVAQWLSTVNTQFYTIKEGMYKALNYQAQALEE 732
B1_B1INP5       -NKNKIIKTIDNALITKRNEKWSDMYGLIVAQWLSTVNTQFYTIKEGMYKALNYQAQALEE 732
B5_EF033130     -NKNKIIKTIETINSALTKRDEKWIDMYGLIVAQWLSTVNTQFYTIQINLIREKMKKALENQAEATKA 732
A4_EU341307     -NKVLTVQTIDNALSKRNEKWDEVYKYIVTNWLAIVNTQINLIREKMKKALENQAEATKA 745
A7_JQ954969     -NKVLTVRTIDNALSKRNEKWEEVYKYIVTNWLAKVNTQINLIREKMKKALENQAEATKA 745
A6_FJ981696     -NKVLTVQTINNALSKRNEKWDEVYKYTVTNWLAKVNTQIDLIREKMKKALENQAEATKA 745
A1_A5HZZ9       -NKVLTVQTIDNALSKRNEKWDEVYKYIVTNWLAKVNTQIDLIREKMKKALENQAEATKA 745
A5_EU679004     -NKVLTVQTIDNALSKRNEKWGEVYKYIVTNWLAKVNTQIDLIRKKMKEALENQAEATKA 745
A3_DQ185900     -NKVLTVQTINNALSKRNEKWDEVYKYIVTNWLAKVNTQIDLIRKKMKEALENQAEATRA 741
A2_X73423       -NKVLTVQTINNALSKRNEKWDEVYKYTVTNWLAKVNTQIDLVRKKMKEALENQAEATKA 745
A8_KM233166     -NKVLTVQTINNALSKRNEKWDEVYKYIVTNWLAKVNTQIDLVRKKMKEQMYKALKNQATAIKK 745
H_KGO15617      RDKDKIIKTLDNALNVRDQKWKELYRWVVSKWLJTTINTQFNKRREQMYKALKNQATAIKK 731
E9_JX424534     DNKNKVIKAINNALKERDEKWKEVYSFIVSNWMTKINTQFNKRREQMYQALQNQVNALKT 717
E12_KM370319    DNKNKIIKAINNALREREKWKEVYSFIVSNWITKINTQFNKRREQMYQALQNQVNAIKT 720
E11_KF861875    DNKNKVIKAINNALKERDEKWKEVYSFIVSNWITKINTQFNKRREQMYQALQNQVNAIKT 717
E10_KF861917    DNKNKVIKAINNALKERDENWKEVYSFIVSNWMTKINTQFNKRREQMYQALQNQVNAIKT 717
E7_JN695729     DNKNKVIKAINNALKERDEKWKEVYSFIVSNWMTKINTQFNKRREQMYQALQNQVNAIKT 717
E8_JN695730     DNKNKVIKAINNALKERDEKWKEVYSFIVSNWMTKINTQFNKRREQMYQALQNQVNAIKT 717
E5_AB037711     DNKNKVIKAINNALKERDEKWKEVYSFIVSNWMTKINTQFNKRREQMYQALQNQVNAIKT 717
E6_AM695759     DNKNKVIKAINNALKERDEKWKEVYSFIVSNWMTKINTQFNKRREQMYQALQNQVNALKT 717
E4_AB088207     DNKNKVIKAINNALKERDEKWKEVYSFIVSNWMTKINTQFNKRREQMYQALQNQVNAIKT 717
E3_EF028403     DNKNKVIKAINNALKERDEKWKEVYSFIVSNWMTKINTQFNKRREQMYQALQNQVNALKA 717
E1_Q00496       DNKNKVIKAINNALKERDEKWKEVYSFIVSNWMTKINTQFNKRREQMYQALQNQVNAIKT 717
E2_EF028404     DSKNKIIKAINNALRERELERAKWKEIYSWIVSNWLTRINTQFNKRREQMYQALQNQVDGIKK 726
F7_GU213233     ENKNKIIKAINNSLIEREAKWKEIYSWIVSNWLTRINTQFNKRREQMYQALQNQVDAIKT 733
F5_GU213211     ENKNKIIKAINNSLIEREAKWKEIYSWIVSNWLTRINTQFNKRREQMYQALQNQVDAIKT 736
F1_Q57236       ENKNKIIKAINNSLMERETKWKEIYSWIVSNWLTRINTQFNKRREQMYQALQNQVDAIKT 736
F4_GU213214     KNEDKIIKAINNSLIEREAKWKEIYSWIVSNWLTRINTQFNKRREQMYQALQNQVDAIKT 736
F2_GU213209     ENKNKAIKAINNALIEREAKWKEIYSWIVSNWLTRINTQFNKRREQMYQALQNQVDAIKT 736
F3_GU213227     ENKNKAIKAINNALIEREAKWKEIYSWIVSNWLTRINTQFNKRREQMYQALQNQVDAIKT 735
F6_M92906       -QKEKIIKTIDNFLEKRYEKWIEVYKLVKAKWLGTVNTQFQKRSYQMYRSLEYQVDAIKK 754
```

FIG. 1N

| | | |
|---|---|---|
| D_P19321 | KIDLEYKKYSGSDKENI---KSQVENLKNSLDVKISEAMNNINKFIRECSVTYLFKNMLPK | 794 |
| DC_AB745660 | KIDLEYKKYSGSDKENI---KSQVENLKNSLDVKISEAMNNINKFIRECSVTYLFKNMLPK | 794 |
| C1_P18640 | KIDLEYKKYSGSDKENI---KSQVENLKNSLDVKISEAMNNINKFIRECSVTYLFKNMLPK | 798 |
| CD_AB200360 | KIDLEYKKYSGSDKENI---KSQVENLKNSLDIKISEAMNNINKFIRECSVTYLFKNMLPK | 798 |
| G_Q60393 | IIEDQYNRYSEEDKMNI---NIDFNDIDFKLNQSINLAINNIDDFINQCSISYLMNRMIPL | 795 |
| B4_EF051570 | IIKYKYNIIYSEEEKSNI---NINFNDINSKLNDGINQAMDNINDFINECSVSYLMKKMIPL | 790 |
| B8_JQ964806 | IIKYKYNIYSEKEKSNI---SIDFNDINSKLNEGINQAIDNINDFINECSVSYLMKKMIPL | 790 |
| B7_JQ354985 | IIKYKYNIYSEKEKLNI---NIDFNDINSKLNEGINQAIDNINNFINECSVSYLMKKMIPL | 790 |
| B6_AB302852 | IIKYKYNIYSEKEKSNI---NIDFNDINSKLNEGINQAVDNINNFINECSVSYLMKKMIPL | 790 |
| B2_AB084152 | IIKYKYNIYSEKEKSNI---NIDFNDINSKLNEGINQAIDNINNFINECSVSYLMKKMIPL | 790 |
| B3_EF028400 | IIKYKYNIYSEKEKSNI---NIDFNDINSKLNEGINQAIDNINNFINECSVSYLMKKMIPL | 790 |
| B1_B1INP5 | IIKYRYNIYSEKEKSNI---NIDFNDINSKLNEGINQAIDNINNFINGCSVSYLMKKMIPL | 790 |
| B5_EF033130 | IIKYKYNIYSEKERSNI---NIDFNDVNSKLNEGINQAIDNINNFINECSVSYLMKKMIPL | 790 |
| A4_EU341307 | IINYQYNQYTEEEKNI---NFNIDDLSSKLNESINSAMININKFLDQCSVSYLMNSMIPY | 803 |
| A7_JQ954969 | IINYQYNQYTEEEKNI---NFNIGDLSSKLNDSINKAMININKFLDQCSVSYLMNSMIPQ | 803 |
| A6_FJ981696 | IINYQYNQYTEEEKNI---NFNIDDLSSKLNESINSAMININKFLDQCSVSYLMNSMIPY | 803 |
| A1_A5HZ29 | IINYQYNQYTEEEKNI---NFNIDDLSSKLNESINKAMININKFLNQCSVSYLMNSMIPY | 803 |
| A5_EU679004 | IINYQYNQYTEEEKNI---NFNIGDLSSKLNDSINKAMININKFLNQCSVSYLMNSMIPY | 803 |
| A3_DQ185900 | IINYQYNQYTEEEKNI---NFNIDDLSSKLNRSINRAMININKFLDQCSVSYLMNSMIPY | 799 |
| A2_X73423 | IINYQYNQYTEEEKNI---NFNIDDLSSKLNESINSAMTNINKFLDQCSVSYLMNSMIPY | 803 |
| A8_KM233166 | IINYQYNQYTEEEKNI---NFNIDDLSSKLNEIERTLNEKINLAMKNIEQFITESSIAYLINIINNE | 803 |
| H_KG015617 | IIENKYNYTTDEKSKIDSSYNINEIERTLNEKINLAMKNIEQFITESSIAYLINIINNE | 791 |
| E9_JX424534 | IIESKYNSYTLEEKNELTNKYDIEQIENELNQKVSIAMNNIDRFLTESSISYLMKLINEV | 777 |
| E12_KM370319 | IIESKYNSYTLEEKNELTNKYDIEQIENELNQKVSIAMNNIDRFLTESSISYLMKLINEV | 780 |
| E11_KF861875 | IIESKYNSYTLEEKNELKNKYDIEQIENELNQKVSIAMNNIEIFLTESSISYLMKLINEV | 777 |
| E10_KF861917 | IIESKYNSYTLEEKNELTNKYNIEQIENELNQTVSIAMNNIEIFLTESSISYLMKLINEV | 777 |
| E7_JN695729 | IIESKYNSYTLEEKNELTNKYNIEQIENELNQKVSIAMNNIDRFLTESSISYLMKLINEV | 777 |
| E8_JN695730 | IIESKYNSYTLEEKNELTNKYDIKQIENELNQKVSIAMNNIEIFLTESSISYLMKLINEV | 777 |
| E5_AB037711 | IIEFKYNSYTLEEKKELKNNYDIEQIENELNQKVSIAMNNIEIFLTESSISYLMKLINEV | 777 |
| E6_AM695759 | IIESKYNSYTLEEKNELTNKYNIEQIENELNQKVSIAMNNIDRFLTESSISYLMKLINEV | 777 |
| E4_AB088207 | IIESKYNSYTLEEKNELTNKYNIEQIENELNQKVSIAMNNIEIFLTESSISYLMKLINEV | 777 |
| E3_EF028403 | IIESKYNSYTLEEKNELTNKYNIEQIENELNQKVSIAMNNIDRFLTESSISYLMKLINEV | 777 |
| E1_Q00496 | IIESKYNSYTLEEKNELTNKYNIEQIENELNQKVSIAMNNIDRFLTESSISYLMKLINEV | 777 |
| E2_EF028404 | IIEYKYNNYTLDEKNRLKAEYNIYSIKEELNKKVSLAMQNIDRFLTESSISYLMKLINEA | 777 |
| F7_GU213233 | AIEYKYNNYTSDEKNRLESEYNINNIEEELNKKVSLAMKNIERFITESSISYLMKLINEA | 786 |
| F5_GU213211 | AIEYKYNNYTSDEKNRLESEYNINNIEELNKKVSLAMENIERFITESSIFYLMKLINEA | 793 |
| F1_Q57236 | VIEYKYNNYTSDERNRLESEYNINNIREELNKKVSLAMKNIERFIAESSISYLMKLINEA | 796 |
| F4_GU213214 | VIEYKYNNYTSDEKNRLESEYNINNIEEELNKKVSLAMKNIERFLTESSISYLMKLINEA | 796 |
| F2_GU213209 | AIEYKYNNYTSDEKNRLESEYNINNIEEELNKKVSLAMKNIERFMTESSISYLMKLINEA | 796 |
| F3_GU213227 | AIEYKYNNYTSDEKNRLESEYNINNIEEELNKKVSLAMKNIERFMTESSISYLMKLINEA | 795 |
| F6_M92906 | IIDYEYKIYSGPDKEQI---ADEINNLKNKLEEKANKAMININIFMRESSRSFLVNQMINE | 812 |

FIG. 10

| | | |
|---|---|---|
| D_P19321 | VIDELNKFDLRTKTELINLIDSHNIILV-GEVDRLKAKVNESFENTMPFNIFSYTNNSLL | 853 |
| DC_AB7455660 | VIDELNKFDLRTKTELINLIDSHNIILV-GEVDRLKAKVNESFENTIPFNIFSYTNNSLL | 853 |
| C1_P18640 | VIDELNEFDRNIKAKLINLIDSHNIILV-GEVDKLKAKVNNSFQNTIPFNIFSYTNNSLL | 857 |
| CD_AB200360 | VIDELNKFDLRTKTELINLIDSHNIILV-GEVDRLKAKINESFENTIPFNIFSYTNNSLL | 857 |
| G_Q60393 | AVKKLKDFDDNLKRDLLEYIDTNELYL-LDEVNILKSKVNRHLKDSIPFFDLSLYTKDTIL | 854 |
| B4_EF051570 | AVEKLLDFDNTLKKNLLNYIDENKLYL-IGSVEDEKSKVDKYLKTIIPFDLSTYTNNEIL | 849 |
| B8_JQ964806 | AVEKLLDFDNTLKKNLLNYIDENKLYL-IGSAEYEKSKVDKHLKTIMTFDLSMYTNNTIL | 849 |
| B7_JQ354985 | AIEKLLDFDNALKKNLLNYIDENKLYL-IGSVEEEKSKVDKFFKTIIPFDLSMYTNNTIL | 849 |
| B6_AB302852 | AVEKLLDFDNTLKKNLLNYIDENKLYL-IGSAEYEKSKVDKHLKTIIPFDLSMYTNNTIL | 849 |
| B2_AB084152 | AVEKLLDFDNTLKKNLLNYIDENKLYL-IGSAEYEKSKVDKHLKTIIPFDLSMYTNNTIL | 849 |
| B3_EF028400 | AVEKLLDFDNTLKKNLLNYIDENKLYL-IGSAEYEKSKVDKHLKTIIPFDLSMYTNNTIL | 849 |
| B1_B1INP5 | AVEKLLDFDNTLKKNLLNYIDENKLYL-IGSAEYEKSKVDKYLKTIMPFDLSIYTNDTIL | 849 |
| B5_EF033130 | AVEKLLDFDNTLRKNLLNYIDENKLYL-IGSAEYEKSKVDKYLKTSIPFDLSTYTNNTIL | 849 |
| A4_EU341307 | AVKRLKDFDASVRDVLLKYIYDNRGTLIGQ-VNRLKDKVNNTLSADIPFQLSKYVDNKKL | 862 |
| A7_JQ954969 | AVKRLKDFDTSLRDSLLKYIYDNRGTLIGQ-VDRLKDKVNNTLSTDIPFQLSKYADNQRL | 862 |
| A6_FJ981696 | AVKRLKDFDASVRDVLLKYIYDNRGTLIGQ-VDRLKDKVNNTLSTDIPFQLSKYVDNQRL | 862 |
| A1_A5HZ29 | GVKRLEDFDASLKDALLKYIYDNRGTLIGQ-VDRLKDKVNNTLSTDIPFQLSKYVDNQRL | 862 |
| A5_EU679004 | GVKRLKDFDASLKDALLKYIYDNRGTLIGQ-VDRLKDKVNNTLSTDIPFQLSKYVDNQRL | 862 |
| A3_DQ185900 | AVKRLKDFDASVRDVLLKYIYDNRGTLILQ-VDRLKDEVNNTLSADIPFQLSKYVDNKKL | 858 |
| A2_X73423 | AVKRLKDFDASVREVLLKYIYDNRGTLILQ-VDRLKDKVNNTLSADIPFQLSKYVDNKKL | 862 |
| A8_KM233166 | TIQKLKSYDDLVRRYLLGYIRNHSSILGNS-VEELNSKVNNHLDNGIPFELSSYTNDSLL | 850 |
| H_KGO15617 | KINKLREYDENVKTYLLDYIILNYIIQHGSILGES-QQELNSMIIDTLNNSIPFKLSSYTDDKIL | 839 |
| E9_JX424534 | KINKLREYDENVKTYLLNYIILNYIIQHGSTLGES-QQELNSMVINTLNNSIPFKLSSYTDDKIL | 839 |
| E12_KM370319 | KINKLREYDENVKTYLLDYIIKHGSILGES-QQELNSMVIDTLNNSIPFKLSSYTDDKIL | 836 |
| E11_KF861875 | KINKLREYDENVKTYLLDYIIKHGSILGES-QQELNSMVIDTLNNSIPFKLSSYTDDKIL | 836 |
| E10_KF861917 | KINKLREYDENVKTYLLDYIIKHGSILGES-QQELNSMVIDTLNNSIPFKLSSYTDDKIL | 836 |
| E7_JN695729 | KINKLREYDENVKTYLNYIIQHGSILGES-QQELNSMVTDTLNNSIPFKLSSYTDDKIL | 836 |
| E8_JN695730 | KINKLREYDENVKTYLNYIIQHGSILGES-QQELNSMVTDTLNNSIPFKLSSYTDDKIL | 836 |
| E5_AB037711 | KINKLREYDENVKTYLLNYIIQHGSILGES-QQELNSMVIDTLNNSIPFKLSSYTDDKIL | 836 |
| E6_AM695759 | KINKLREYDENVKTYLLDYIIKHGSILGES-QQELNSMVIDTLNNSIPFKLSSYTDDKIL | 836 |
| E4_AB088207 | KINKLREYDENVKTYLLDYIIKHGSILGES-QQELNSMVIDTLNNSIPFKLSSYTDDKIL | 836 |
| E3_EF028403 | KINKLREYDENVKTYLLDYIIKHGSILGES-QQELNSMVIDTLNNSIPFKLSSYTDDKIL | 836 |
| E1_Q00496 | KINKLREYDENVKTYLLNYIIQHGSILGES-QQELNSMVTDTLNNSIPFKLSSYTDDKIL | 836 |
| E2_EF028404 | KINKLREYDENVKTYLLNYIIQHGSILGES-QQELNSMVTDTLNNSIPFKLSSYTDDKIL | 836 |
| F7_GU213233 | KINKLSEYDKRVNQYLLNYILENSSTLGTSSVQELNNLVSNTLNNSIPFELSEYTNDKIL | 846 |
| F5_GU213211 | EVGKLKEYDKRVKRHLLEYIFDYRLILGEQ-GGELIDLVTSTLNTSIPFELSSYTNDKIL | 852 |
| F1_Q57236 | KVSKLREYDEGVKEYLLDYISEHRSILGNS-VQELNDLVTSTLNNSIPFELSSYTNDKIL | 855 |
| F4_GU213214 | KVSELREYDEGVKEYLLDYILKNGSILGDH-VQELNDLVTSTLNSSIPFELSSYTNDKIL | 855 |
| F2_GU213209 | EVGKLKEYDKHVKSDLLDYILYHKLILGEQ-TKELIDLVTSTLNSSIPFELSSYTNDKIL | 855 |
| F3_GU213227 | EVGKLKEYDRHVKSDLLDYILYHKLILGDQ-TKELIDLVTSTLNSSIPFELSSYTNDKIL | 855 |
| F6_M92906 | KVGKLKKYDNHVKSDLLNYILDHRSILGEQ-TNELSDLVTSTLNSSIPFELSSYTNDKIL | 854 |
| T_P04958 | AKKQLLEFDTQSKNILMQYIKANSKFIGITELKKLESKINKVFSTPIPFSYSKNLDC--W | 870 |

FIG. 1P

```
D_P19321      KDIINEYFNSINDSKILSLQNKK---NALVDTSGYNAEVRVGDNVQL-NTIYTNDFKLSSS          910
DC_AB745660   KDMINEYFNSINDSKILSLQNKK---NTLMDTSGYNAEVRVEGNVQL-NPIFPFDFKLGSS          910
C1_P18640     KDIINEYFNNINDSKILSLQNRK---NTLVDTSGYNAEVSEEGDVQL-NPIFPFDFKLGSS          914
CD_AB200360   KDIINEYFNSINDSKILSLQNKK---NALVDTSGYNAEVRLEGDVQV-NTIYTNDFKLSSS          914
G_Q60393      IQVFNNYISNAILSLSYRG---GRLIDSSGYGATMNVGSDVIF-NDIGNGQFKLNNS              911
B4_EF051570   IKIFNKYNSEILNNIILNLRYDN--NNLIDLSGYGAKVEVYDGVKL-ND--KNQFKLTSS           904
B8_JQ964806   IKMVNKYNSEILNNIILNLRYRD--NNLIDLSGYGANVEVYDGVEL-ND--KNQFKLTSS           904
B7_JQ354985   IEMVNKYNSEILNNIILNLRYRD--NNLIDSSGYGAKVEVYNGVEL-ND--KNQFKLTSS           904
B6_AB302852   IEIFKKYNSEILNNIILNLRYRD--NNLIDLSGYGANVEVYDGVEL-ND--KNQFKLTSS           904
B2_AB084152   IEIFNKYNSEILNNIILNLRYRD--NNLIDLSGYGAKVEVYDGVEL-ND--KNQFKLTSS           904
B3_EF028400   IEIFNKYNSEILNNIILNLRYKD--NNLIDLSGYGAKVEVYDGVEL-ND--KNQFKLTSS           904
B1_B1INP5     IEMFNKYNSEILNNIILNLRYRD--NNKLIDLSGYGAKVEVYDGVKL-ND--KNQFKLTSS          904
B5_EF033130   IEIFNKYNSDILNNIILNLRYRD--NKLIDLSGYGAKVEVYDGVKL-ND--KNQFKLTSS           904
A4_EU341307   IEIFNKYNSDILNNITNASILSIVYKD--DDLIDLSRYGAEIYNGDKVYY-NSIDKNQIRLINL       919
A7_JQ954969   LSTFTEYIKNITNASILSIVYKD--NHLIDLSRYASKINIGSRVNF-DPIDKNQIQLFNL          919
A6_FJ981696   LSTFTEYIKNIINTSILSLRYEN--NHLIDLSRYASKINIGSRVNF-DPIDKNQIQLFNL          919
A1_A5HZ9      LSTFTEYIKNIINTSILSLRYES--NHLIDLSRYASEINIGSKVNF-DPIDKNQIQLFNL          919
A5_EU679004   LSTFTEYIKNIINTSILNLRYES--NHLIDLSRYASEINIGSKVNF-DPIDKNQIQLFNL          919
A3_DQ185900   LSTFTEYIKNIVNTSILSIVYKK--DDLIDLSRYGAKINIGDRVYY-DSIDKNQIKLINL          915
A2_X73423     LSTFTEYIKNIVNTSILSIVYKK--DDLIDLSRYGAKINIGDRVYY-DSIDKNQIKLINL          919
A8_KM233166   LSTFTEYIKNITNTSILSIVVDKD--GRLIDLSRYGAEIYNGDKVSY-NSIDKNQVQLSNL         920
H_KG015617    IRYFNKNYGELKYNCILNIKYEMDRDKLVDSSGYRSRINIGTGVKF-SEIDKNQVQLSNL          909
E9_JX424534   ISYFNKFFKTIKSSSVLSMRYKN--DKYIDTSGYDSNININGDVFI-YPTNKNQFGIYNS          893
E12_KM370319  ISYFNKFFKRIKSSSVLNMRYKN--DKYVDTSGYDSNININGEIFI-YPTNKNQFSIFNS          896
E11_KF861875  ISYFNKFFKRIKSSSVLNMRYKN--DKYIDTSGYDSNINIKGDVFI-YPTNKNQFGIYNN          893
E10_KF861917  ISYFNKFFKRIKSSSVLNMRYKN--DKYVDTSGYDSNININGDVYK-YPTNKNQFGIYND          893
E7_JN695729   ISYFNKFFKRIKSSSVLNMRYKN--DKYVDTSGYDSNININGDVYK-YPTNKNQFGIYND          893
E8_JN695730   ISYFNKFFKRIKSSSVLNMRYKN--DKYVDTSGYDSNININGDVYK-YPTNKNQFGIYND          893
E5_AB037711   ISYFNKFFKRIKSSSVLNMRYKN--DKYVDTSGYDSNININGEIFI-YPTNKNQFTIFNS          893
E6_AM695759   ISYFNKFFKRIKSSSVLNMRYKN--DKYVDTSGYDSNININGDVYK-YPTNKNQFGIYNN          893
E4_AB088207   ISYFNKFFKRIKSSSVLNMRYEN--DKYVDTSGYDSNININGDVYK-YPTNKNQFGIYND          893
E3_EF028403   ISYFNKFFKRIKSSSVLNMRYEN--DKYVDTSGYDSNININGDVYK-YPTNKNQFGIYND          893
E1_Q00496     ISYFNKFFKRIKSSSVLNMRYEN--DKYVDTSGYDSNININGDVYK-YPTNKNQFGIYND          893
E2_EF028404   ISYFNKFFKRIKSSSVLNMRYEN--DKYVDTSGYDSNININGDVYK-YPTNKNQFGIYND          893
F7_GU213233   ISYFNRFYKRIIDSSILNMKYEN--NRFIDSSGGSNISINGDIYI-YSTNRMQFGIYSS           903
F5_GU213211   IIYFNRLYKKIKDSSILDMRYEN--NKFIDIGYGSNISINGNVYI-YSTNRNQFGIYDD           909
F1_Q57236     IIYFNRLYKKIKDSSILDMRYEN--NKFIDISGYGSNISINGDVYI-YSTNRNQFGIYSS          912
F4_GU213214   IIYFNKLYKKIKDNCILDMRYEN--NKFIDISGYGSNISINGELYI-YTTNRMQFTIYSG          912
F2_GU213209   IIYFNRLYKKIKDSSILDMRYEN--NKFIDISGYGSNISINGNVYI-YSTNRNQFGIYSG          912
F3_GU213227   IIYFNRLYKKIKDSSILDMRYEN--NKFIDISGYGSNISINGNVYI-YSTNRNQFGIYSD          912
F6_M92906     IIYFNRLYKKIKDSSILDMRYEN--NKFIDISGYGSNISINGNVYI-YSTNRNQFGIYNS          911
T_P04958      VDNEEDIDVILKKSTILNLDINN---DIISDISGFNSSVITYPDAQLVPGINGKAIHLVNN         928
```

| ID | Sequence | # |
|---|---|---|
| D_P19321 | -NSGWKLCIRN------GNIEWILQDVNRKYKSLIFDYSESLSHTGYTNKWFFVTITNNIMG | 1013 |
| DC_AB745660 | -NSGWSIGIIS------NFLVFTLKQNENSEQDINFSYDISKNAAGY-NKWFFVTITTNMMG | 1014 |
| C1_P18640 | -NSGWSIGIIS------NFLVFTLKQNEDSEQSINFSYDISNNAPGY-NKWFFVTVINNNMG | 1018 |
| CD_AB2003060 | -NSGWKLCIRN------GNIEWILQDINRKYKSLIFDYSESLSHTGYTNKWFFVTITNNIMG | 1017 |
| G_Q60393 | -DSGWKVSIKG------NRIIWTLIDVNAKSKSIFFEYSIKDNISDYINKWFSITITNDRLG | 1020 |
| B4_EF051570 | -NSGWKISIRG------NRIIWTLIDINGKTKSVFFEYNIREDISEYINRWFFVTITN-NLD | 1012 |
| B8_JQ964806 | -NSGWKISIRG------NRIIWTLIDINGKTKSIKSVFFEYSIRKDVSEYINRWFFVTITN-NLD | 1012 |
| B7_JQ354985 | -NSGWKISIRG------NRIIWTLTDINGKTKSVFFEYSIREDISDYINRWFFVTITN-NLD | 1012 |
| B6_AB302852 | -NSGWKISIRG------NRIIWTLIDINGKTKSVFFEYSIREDISDYINRWFFVTITN-NSD | 1012 |
| B2_AB084152 | -NSGWKISIRG------NRIIWTLIDINGKTKSVFFEYSIREDISDYINRWFFVTITN-NSD | 1012 |
| B3_EF028400 | -NSGWKISIRG------NKIIWTLIDINGKTKSVFFEYSIRKDVSEYINRWFFVTITN-NSD | 1012 |
| B1_B1INP5 | -NSGWKISIRG------NRIIWTLIDINGKTKSVFFEYNIREDISEYINRWFFVTITN-NLN | 1012 |
| B5_EF033130 | -NSGWKISIRG------NMIIWTLIDINGKTKSIKSVFFEYSIKEDISEYINRWFFVTITN-NSD | 1012 |
| A4_EU341307 | -NSGWKVSLNY------GEIIWTFQDTQEIKQRVVFKYSQMINISDYINRWIFVTITNNRIT | 1025 |
| A7_JQ954969 | -NSGWKVSLNY------GEIIWTLQDNEQNIQRVVFKYSQMVNISDYINRWIFVTITNNRLT | 1025 |
| A6_FJ981696 | -NSGWKVSLNY------GEIIWTLQDNKQNIQRVVFKYSQMVAISDYINRWIFITITNNRLT | 1025 |
| A1_A5HZZ9 | -NSGWKVSLNY------GEIIWTLQDTQEIKQRVVFKYSQMINISDYINRWIFITITNNRLN | 1025 |
| A5_EU679004 | -NSGWKVSLNY------GEIIWTLQDNKQNIQRVVFKYSQMVAISDYINRWIFITITNNRLN | 1025 |
| A3_DQ185900 | -NSGWKVSLNY------GEIIWTLQDNKQNIQRVVFKYSQMVNISDYINRWMFVTITNNRLT | 1021 |
| A2_X73423 | -NSGWKVSLNY------GEIIWTLQDNKQNQQNIQRVVFKYSQMVNISDYINRWIFVTITNNRLT | 1025 |
| A8_KM233166 | -NSGWEVSLNF SNMNSKIIWTLQDTEGIKKTVVFQYTQNINISDYINRWIFVTITNNRLD | 1026 |
| H_KGO15617 | -NSGWKISLNH------NEIIWTLQDNAGINQKLVFKYGNANGISDYINKWIFVTITNNRLS | 1017 |
| E9_JX424534 | -NSGWKISLNH------NEIIWTLQDNAGINQKLVFKYGNSNGISDYINKWIFVTITNDRLG | 1001 |
| E12_KM370319 | -NSGWKISLNH------NEIIWTLQDNAGINQKLAFNYGNANGISDYINKWIFVTITNDRLG | 1004 |
| E11_KF861875 | -NSGWKISLNH------NEIIWTLQDNAGINQKLAFNYGNANGISDYINKWIFVTITNDRLG | 1001 |
| E10_KF861917 | -NSGWKVSLNH------NEIIWTLQDNAGINQKLAFNYGNANGISDYINKWIFVTITNDRLG | 1001 |
| E7_JN695729 | -NSGWKVSLNH------NEIIWTLQDNAGINQKLAFNYGNANGISDYINKWIFVTITNDRLG | 1001 |
| E8_JN695730 | -NSGWKVSLNH------NEIIWTLQDNARINQKLVFKYGNANGISDYINKWIFVTITNDRLG | 1001 |
| E5_AB037711 | -NSGWKVSLNH------NEIIWTLQDNSGINQKLVFKYGNANGISDYINKWIFVTITNDRLG | 1001 |
| E6_AM695759 | -NSGWKVSLNH------NEIIWTLQDNSGINQKLAFNYGNANGISDYINKWIFVTITNDRLG | 1001 |
| E4_AB088207 | -NSGWKVSLNH------NEIIWTLQDNAGINQKLVFNYGNANGISDYINKWIFVTITNDRLG | 1001 |
| E3_EF028403 | -NSGWKVSLNH------NEIIWTLQDNAGINQKLAFNYGNANGISDYINKWIFVTITNDRLG | 1001 |
| E1_Q00496 | -NSGWKVSLNH------NEIIWTLQDNAGINQKLAFNYGNANGISDYINKWIFVTITNDRLG | 1001 |
| E2_EF028404 | -NSGWKVSLNH------NEIIWTLQDNAGINQKLVFNYTQMIDISDYINKWTFVTITNDRLG | 1001 |
| F7_GU213233 | -NSGWKISLNY------NNIIWTLQDTTGNNQKLVFNYTQMIDISDYINKWTFVTITNNRLG | 1010 |
| F5_GU213211 | -NSGWKISLRTTG-DCEIIWTLQDTSGNKKKLIFRYSQLGGISDYINKWIFVTITNNRLG | 1019 |
| F1_Q57236 | -NSGWKISLNY------NKIIWTLQDTAGNNQKLVFNYTQMISISDYINKWIFVTITNNRLG | 1019 |
| F4_GU213214 | -NSGWKISLNY------NKIIWTLQDTAGNNEKLVFNYTQMISISDYINKWIFVTITNNRLG | 1019 |
| F2_GU213209 | -NSGWKISLRTIR-DCEIIWTLQDTSGNKEKLIFRYEELASISDYINKWIFVTITNNRLG | 1022 |
| F3_GU213227 | -NSGWKISLRNIR-DCEIIWTLQDTSGNKEKLIFRYEELANISDYINKWIFVTITNNRLG | 1022 |
| F6_M92906 | -NSGWKISLRTVR-DCEIIWTLQDTSGNKENLIFRYEELNRISNYINKWIFVTITNNRLG | 1021 |
| T_P04958 | IGSGWSVSLKG------NNLIWTLKDSAGEVRQITFRDLPDKFNAYLANKWVFITITNDRLS | 1042 |

| | | |
|---|---|---|
| D_P19321 | ------------LVQYPDRSKLYTGNPITIKSVS----DKNPYSRILNGDNII-LHMLYNS-RKY | 1166 |
| DC_AB745660 | ------------FNTRKNNNDFNEGYKIIIKRII----GNTNDTRVR-GENVLYFNTTIDN-KQY | 1175 |
| C1_P18640 | ------------FNTRRNNNDFNEGYKIIIKRIR----GNTNDTRVRGGDI-LYFDMTINN-KAY | 1179 |
| CD_AB200360 | ------------LVQYSDISKLYTKNPITIKSAA----NKNPYSRILNGDD-IMFHMLYDS-REY | 1170 |
| G_Q60393 | ---PRTNFN---NAAINYQNLYLGLRFIIKKASNSRNINNDNIVREGDY-IYLNIDNISDESY | 1186 |
| B4_EF051570 | --IRSKYNQNSNYINYRNLYIGEKFIIRRKSNSQSIN--DDIVRKEDY-IHLDFVNSN-EEW | 1178 |
| B8_JQ964806 | --TRSKYNQNSQYINYRDLYIGEKFIIRRKSNSQSIN--DDIVRKEDY-IYLDFFNLN-QEW | 1178 |
| B7_JQ354985 | --TRSKYNQNSNYINYRNLYIGEKFIIRRKSSSQSIS--DDIVRKEDY-IYLDFFNSN-REW | 1178 |
| B6_AB302852 | --TRSKYNQNSNYINYRNLYIGEKFIIRRKSNSQSIS--DDIVRKEDY-IYLDFFNSN-QEW | 1178 |
| B2_AB084152 | --TRSKYNQNSNYINYRNLYIGEKFIIRRKSNSQSIN--DDIVRKEDY-IYLDFFNLN-QEW | 1178 |
| B3_EF028400 | --TRSKYNQNSNYINYRNLYIGEKFIIRRKSNSQSIN--DDIVRKEDY-IYLDFFNLN-REW | 1178 |
| B1_B1INP5 | --TRSKYNQNSKYINYRDLYIGEKFIIRRKSNSQSIN--DDIVRKEDY-IYLDFFNLN-QEW | 1178 |
| B5_EF033130 | --TRSKYNQNSKYINYRDLYIGEKFIIRRKSNSQSIN--DDIVRKEDY-IYLDFFNLN-QEW | 1178 |
| A4_EU341307 | GPRDNVMTTNIYLN-SSLYMGTKFIIKKYA---SGNKDNIVRNNDR-VYINVVVKN-KEY | 1191 |
| A7_JQ954969 | GPRGSVTTTNIYLN-SMLYMGTKFIIKKHA---SGNKDNIVRNNDR-VYINVLVKN-KEY | 1191 |
| A6_FJ981696 | GSRSTLLITTNIYLN-SGLYMGTKFIIKKYA---SGNKDNIVRNNDR-VYINVVVNN-KEY | 1191 |
| A1_A5HZZ9 | GPRGSVMTTNIYLN-SSLYRGTKFIIKKYA---SGNKDNIVRNNDR-VYINVVVKN-KEY | 1191 |
| A5_EU679004 | GPRGSIVTTNIYLN-SSLYMGTKFIIKKYA---SGNKDNIVRNNDR-VYINVVVKN-KEY | 1191 |
| A3_DQ185900 | GPRGSVMTTNIYLN-STLYMGTKFIIKKYA---SGNEDNIVRNNDR-VYINVVVKN-KEY | 1187 |
| A2_X73423 | GPRGSVVTTNIYLN-STLYEGTKFIIKKYA---SGNKDNIVRNNDR-VYINVVVKN-KEY | 1191 |
| A8_KM233166 | GPRGRIVTTNIYLN-STLYMGTKFIIKKYA---SGNKDNIVRNNDR-VYINVVVKN-KEY | 1192 |
| H_KGO15617 | NNR-----NIVNGL-YRLYSGIKVKIQKIN--DSDTRDNIVRDNDQ-VYVNYINGN-VYY | 1183 |
| E9_JX424534 | NHR-----YIVNGL-YRLYSGIKVKIQRVN--DSSTNDQFVRKNDQ-VYINYIYNN-LSY | 1159 |
| E12_KM370319 | NIR-----STIVLA-NRLYSGIKVKIQRVN--NSSTNDNLVRKNDQ-VYINFVASKTHLF | 1162 |
| E11_KF861875 | NIR-----STIVLA-NKLYLGIKVKIQRVN--NSSTNDNLVRKNDQ-VYINFVP IKTHLF | 1160 |
| E10_KF861917 | NIR-----STILLA-NRLYSGIKVKIQRVN--NSSTNDNLVRKNDQ-VYINFVASKTHLF | 1160 |
| E7_JN695729 | NIR-----STILLA-NRLYSGIKVKIQRVN--NSSTNDNLVRKNDQ-VYINFVASKTHLF | 1160 |
| E8_JN695730 | NIR-----STILLA-NRLYSGIKVKIQRVN--DSSTNDRFVRKNDQ-VYINYISNS-SSY | 1159 |
| E5_AB037711 | NIR-----STILLA-NRLYSGIKVKIQRVN--NSSTNDNLVRKNDQ-VYINFVDSKTHLL | 1160 |
| E6_AM695759 | NIR-----STILLA-NRLYSGIKVKIQRVN--NSSTNDNLVRKNDQ-VYINFVASKTHLL | 1160 |
| E4_AB088207 | NIR-----STILLA-NRLYSGIKVKIQRVN--NSSTNDNLVRKNDQ-VYINFVASKTHLF | 1160 |
| E3_EF028403 | NIR-----STILLA-NRLYSGIKVKIQRVN--NSSTNDNLVRKNDQ-VYINFVASKTHLF | 1160 |
| E1_Q00496 | NIR-----STILLA-NRLYSGIKVKIQRVN--NSSTNDNLVRKNDQ-VYINFVASKTHLF | 1160 |
| E2_EF028404 | NIR-----STILLA-NRLYSGIKVKIQRVN--NSSTNDNLVRKNDQ-VYINFVASKTHLF | 1160 |
| F7_GU213233 | RQRGIYSKTNIFSN-ARLYTGVEVIIRKVGSTDTSNTDNFVRKNDT-VYINVVDGN-SEY | 1174 |
| F5_GU213211 | HQRGVTKDLFIFSN-YKLYEGVEVIIRKNGPIDISNTDNFVRKNDL-AYINVVDHG-VEY | 1183 |
| F1_Q57236 | QQRGVYQKPNIFSN-TRLYTGVEVIIRKNGSTDISNTDNFVRKNDL-AYINVVDRD-VEY | 1183 |
| F4_GU213214 | RARGVDRKANIFSN-KRLYKGVEVIIRKNEPIDISNTDNFVRKGDL-AYINVVDRD-VEY | 1183 |
| F2_GU213209 | QQRGVTGGISVFLN-YKLYEGVEVIIRKNGPIDISNTDNFVRKNDL-AYINVVDHG-VEY | 1186 |
| F3_GU213227 | QQRGVTEG-SVFLN-YKLYEGVEVIIRKNGPIDISNTDNFVRKNDL-AYINVVYHD-VEY | 1185 |
| F6_M92906 | QQRGVTEG-SVFLN-YKLYEGVEVIIRKNGPIDISNTDNFVRKNDL-AYINVVDRG-VEY | 1184 |
| T_P04958 | --NAPSYTNGKLNIYYRRLYNGLKFIIKRYTPNNEI--DSFVKSGDF-IKLYVSYNNNEHI | 1208 |

FIG. 1V

```
D_P19321         MI------IRDT--DTIYATQGGECSQNCVYALKLQSNLG-NYG-IGIFSIKNIVSKNKYC  1217
DC_AB745660      SLGMYKPSRNL-GTDLVPLGA-LDQ------PMDEIR-KY---GSFIIQPCNTFDYYA    1221
C1_P18640        NL------FMKN-ETMYADNHS---TEDIYAIGLREQTK-DINDNIIFQIQPMNNTYYA    1228
CD_AB200360      MI------IRDT--DTIYATQGGQCSKNCVYALKLQSNLG-NYG-IGIFSIKNIVSQNKYC  1221
G_Q60393         RVYLVNSKEI--QTQL------------FLAPINDDP-TFYDVLQIK-KYYEKTTYNC    1229
B4_EF051570      RVYAYKNFKEQ-EQKL------------FLSIIYDSN-EFYKTIQIK-EYDEQPTYSC    1221
B8_JQ964806      RVYAYKDFKGQK-EQKL-----------FLANIHDSN-EFYKTIQIK-EYDEQPTYSC    1222
B7_JQ354985      RVYAYKNFKGQE-EKL------------FLANIYDSN-EFYKTIQIK-EYDEQPTYSC    1221
B6_AB302852      RVYALKNFKKKE-EKL------------FLANIYDSN-EFYKTIQIK-EYDEQPTYSC    1221
B2_AB084152      RVYAYKDFKEEE-EKL------------FLANIYDSN-EFYKTIQIK-EYDEQPTYSC    1221
B3_EF028400      RVYAYKDFKKKE-EKL------------FLANIYDSN-EFYNTIQIK-EYDEQPTYSC    1221
B1_B1INP5        RVYTYKYFKKEE-EKL------------FLAPISDSD-EFYNTIQIK-EYDEQPTYSC    1221
B5_EF033130      RVYMYKYFKKEE-EKL------------FLAPISDSD-EFYNTIQIK-EYDEQPTYSC    1221
A4_EU341307      RLATNASQAGV-EKIL------------SALEIPDVG-NLSQVVVMKSKNDQGIRNKC    1235
A7_JQ954969      RLATNASQAGG-EKIL------------SAVEIPDVG-NLSQVVVMKSKNDQGIRNKC    1235
A6_FJ981696      RLATNASQAGV-EKIL------------SALEIPDIG-NLSQVVVMKSKNDQGIRNKC    1235
A1_A5HZZ9        RLATNASQAGV-EKIL------------SALEIPDVG-NLSQVVVMKSKNDQGITNKC    1235
A5_EU679004      RLATNASQAGV-EKIL------------SVLEIPDVG-NLSQVVVMKSKNDQGITNKC    1235
A3_DQ185900      RLATNASQAGV-EKIL------------SALEIPDVG-NLSQVVVMKSKDDQGIRNKC    1231
A2_X73423        RLATNASQAGV-EKIL------------SALEIPDVG-NLSQVVVMKSKDDQGIRNKC    1235
A8_KM233166      RLATNALQAGV-EKIL------------SAVEIPDVG-NLSQVVVMKSENDQGIRNKC    1236
H_KGO15617       SLYADTNATNK-EKTI------------K------SSTSGNRFNQVVVMN------SVRNNC  1227
E9_JX424534      SLYADTNIKDK-EKTI------------K------SSLSGNIFNQVVVMN------SVGNNC  1196
E12_KM370319     SLYADTNTTNK-EKTI------------K------SSSSGNRFNQVVVMN------SVGNNC  1199
E11_KF861875     PLYADTNTTNK-EKTI------------K------SSSSGNRFNQVVVMN------SVGNNC  1197
E10_KF861917     PLYADTATTNK-EKTI------------K------SSSSGNRFNQVVVMN------SVGNNC  1197
E7_JN695729      PLYADTNTTNK-EKTI------------K------ISSSGNRFNQVVVMN------SVGNNC  1197
E8_JN695730      PLYADTNTTNK-EKTI------------K------SSSSGNRFNQVVVMN------SVGNNC  1197
E5_AB037711      SLYADTNTTDK-EKTI------------K------SSSSGNRFNQVVVMN------SVGNNC  1196
E6_AM695759      PLYADTATTNK-EKTI------------K------ISSSGNRFNQVVVMN------SVGNNC  1197
E4_AB088207      PLYADTATTNK-EKTI------------K------ISSSGNRFNQVVVMN------SVGNNC  1197
E3_EF028403      PLYADTATTNK-EKTI------------K------ISSSGNRFNQVVVMN------SVGNNC  1197
E1_Q00496        PLYADTATTNK-EKTI------------K------ISSSGNRFNQVVVMN------SVGNNC  1197
E2_EF028404      PLYADTNTTNK-EKTI------------K------SSSSGNRFNQVVVMN------SVGNNC  1197
F7_GU213233      QLYADVSTSAV-EKTI------------KLRRISNSNYNSNQMIIMD-------SIGDNC    1214
F5_GU213211      RLYADISITKP-EKII------------KLIRRSNPDDSLGQIIVMD-------SIGNNC    1223
F1_Q57236        RLYADISIAKP-EKII------------KLIRTSNSNNSLGQIIVMD-------SIGNNC    1223
F4_GU213214      RLYANTSNAQP-EKTI------------KLIRTSNSNDSLDQIIVMD-------SIGNNC    1223
F2_GU213209      RLYADISITKS-EKII------------KLIRTSNPNDSLGQIIVMD-------SIGNNC    1226
F3_GU213227      RLYADISITKP-EKII------------KLIRTSNPNDSLGQIIVMD-------SIGNNC    1225
F6_M92906        RLYADTKSEK--E-------------KIIRTSNLNDSLGQIIVMD-------SIGNNC     1220
T_P04958         VGYPKDGNAFNNLDRIL-----------RVGYNAPGI-PLYKKMEAV-KLRDLKTYSV     1253
```

FIG. 1W

```
D_P19321       SQIFSSFRENTMLLA-------------------------DIYKPWRFSFKNAYTPVAVTNYET        1256
DC_AB745660    SQLFLSSNATTNRIGILSIGSYS------------------FKLGDDYWFNHEYLIPVIKIEHYAS        1269
C1_P18640      SQIFKSNFNGENISGICSIGTYR------------------ERLGGDW-YRHNYLVPTVKQGNYAS        1275
CD_AB200360    SQIFSSFMKNTMLL-ADIYKPWR------------------FSFEN---------AYTPVAVTNYET        1260
G_Q60393       QILCEKDTK----TFGLFGIGKFVKDYGYVWDTYDNYFCISQWYLRRISE------------NI        1277
B4_EF051570    QLLFKKDEESTDDIGLIGIHRFY-ESGVLRKKYKDYFCISKWYLKEVKR------------KP        1271
B8_JQ964806    QLLFKKDEESTDEIGLIGIHRFY-ESGFVFQEYKYYFCISKWYLKEVKK------------KP        1272
B7_JQ354985    QLLFKKDEESTDEIGLIGIHNFY-ESGILFKDYKDYFCISKWYLKEVKR------------KP        1271
B6_AB302852    QLLFKKDEESTDEIGLIGIHRFY-ESGIVFKDYKYYFCISKWYLKEVKR------------KP        1271
B2_AB084152    QLLFKKDEESTDEIGLIGIHRFY-ESGIVLKDYKNYFCISKWYLKEVKR------------KP        1271
B3_EF028400    QLLFKKDEESTDEIGLIGIHRFY-ESGIVFKDYKDYFCISKWYLKEVKR------------KP        1271
B1_B1INP5      QLLFKKDEESTDEIGLIGIHRFY-ESGIVFEEYKDYFCISKWYLKEVKR------------KP        1271
B5_EF033130    QLLFKKDEESTDEIGLIGIHRFY-ESGIVFKEYKDYFCISKWYLKEVKR------------KP        1271
A4_EU341307    KMNLQDNN---GNDIGFIGFHQFN-----------------NIAKLVASNWYNRQIER------SS        1275
A7_JQ954969    KMNLQDNN---GNDIGFIGFHQFN-----------------NIAKLVASNWYNRQIGK------TS        1275
A6_FJ981696    KMNLQDNN---GNDIGFIGFHKFN-----------------DIYKLVASNWYNRQIEI------SS        1275
A1_A5HZZ9      KMNLQDNN---GNDIGFIGFHQFN-----------------NIAKLVASNWYNRQIER------SS        1275
A5_EU679004    KMNLQDNN---GNDIGFIGFHQFN-----------------NIDKLVASNWYNRQIER------SS        1275
A3_DQ185900    KMNLQDNN---GNDIGFVGFHLYD-----------------NIAKLVASNWYMRQVGK------AS        1271
A2_X73423      KMNLQDNN---GNDIGFIGFHLYD-----------------NIAKLVASNWYNRQVGK------AS        1275
A8_KM233166    KMNLQDNN---GNDIGLIGFIGFN-----------------NIAKLVASNWYNRQIGK------AS        1276
H_KGO15617     KMNLQDNN---GHDIGLLGFKSN------------------ALVASTWYYTNMRD--------HT        1267
E9_JX424534    TMNFKNNN---GNNIGLLGFKDN------------------TLIVASTWYYTHMRD--------NT        1232
E12_KM370319   TMNFKNNN---GNNIGMLGFKDN------------------TLIVASTWYYTHMRD--------NT        1235
E11_KF861875   TMNFKNNN---GNNIGMLGFKDN------------------TVVASTWYYTHMRD--------NT        1233
E10_KF861917   TMNFKNNN---GNNIGLLGFKAD------------------TLIVASTWYYTHMRD--------HT        1233
E7_JN695729    TMNFKNNN---GNNIGLLGFKAD------------------TVVASTWYYTHMRD--------NT        1233
E8_JN695730    TMNFKNNN---GNNIGLLGFKAD------------------TVVASTWYYTHMRD--------NT        1233
E5_AB037711    TMNFKNNN---GNNIGLLGFKAD------------------TVVASTWYYTHMRD--------HT        1232
E6_AM695759    TMNFKNNN---GNNIGLLGFKAD------------------TVVASTWYYTHMRD--------NT        1233
E4_AB088207    TMNFKNNN---GNNIGLLGFKAD------------------TVVASTWYYTHMRD--------NT        1233
E3_EF028403    TMNFKNNN---GNNIGLLGFKAD------------------TVVASTWYYTHMRD--------HT        1233
E1_Q00496      TMNFKNNN---GNNIGLLGFKAD------------------TVVASTWYYTHMRD--------NT        1233
E2_EF028404    TMNFKNNN---GNNIGMLGFKDN------------------TLIVASTWYYTHMRD--------NT        1233
F7_GU213233    TMNFKTNN---GNDIGLLGFHLN------------------NLIVASSWYYKNIRN--------NT        1250
F5_GU213211    TMNFQNNN---GGNIGLLGFHSD------------------NLIVASSWYYNNIRR--------NT        1259
F1_Q57236      TMNFQNNN---GGNIGLLGFHSN------------------NLIVASSWYYNNIRK--------NT        1259
F4_GU213214    TMNFQNNN---GGNIGLLGFHSN------------------TLIVASSWYYNNIRR--------NT        1259
F2_GU213209    TMNFQNND---GSNIGLLGFHSD------------------DIVASSWYYNHIRR--------NT        1262
F3_GU213227    TMNFQNNN---GGNIGLLGFHSD------------------NLIVASSWYYNNIRR--------NT        1261
F6_M92906      TMNFQNNN---GSNIGLLGFHSN------------------NLIVASSWYYNNIRR--------NT        1256
T_P04958       QLKLYDDK---NASLGLVGTHNGQ------IGNDPNRDILIASNWYFNHLKD-------------K-        1297
```

FIG. 1X

| | | |
|---|---|---|
| D_P19321 | KLLSTSSFWKFISRDPGWVE------ | 1275 |
| DC_AB745660 | LLESTSTHWVFVPASE---------- | 1285 |
| C1_P18640 | LLESTSTHWGFVPVSE---------- | 1291 |
| CD_AB200360 | KLLSTSSFWKFISRDPGWVE------ | 1280 |
| G_Q60393 | NKLRLGCNWQFIPVDEGWTE------ | 1297 |
| B4_EF051570 | YKSNLGCNWQFIPKDEGWTE------ | 1291 |
| B8_JQ964806 | YNPDLGCNWQFIPKDEGWTE------ | 1292 |
| B7_JQ354985 | YSSNLGCNWQFIPKDEGWTE------ | 1291 |
| B6_AB302852 | YNPNLGCNWQFIPKDEGWIE------ | 1291 |
| B2_AB084152 | YNPNLGCNWQFIPKDEGWIE------ | 1291 |
| B3_EF028400 | YNPNLGCNWQFIPKDEGWIE------ | 1291 |
| B1_B1INP5 | YNLKLGCNWQFIPKDEGWTE------ | 1291 |
| B5_EF033130 | YNSKLGCNWQFIPKDEGWTE------ | 1291 |
| A4_EU341307 | ---RTLGCSWEFIPVDDGWRERPL | 1296 |
| A7_JQ954969 | ---VTLGCSWELIPVDYGWGESSL | 1296 |
| A6_FJ981696 | ---RTFGCSWEFIPVDDGWGEKPL | 1296 |
| A1_A5HZZ9 | ---RTLGCSWEFIPVDDGWGERPL | 1296 |
| A5_EU679004 | ---RTFGCSWEFIPVDDGWGESPL | 1296 |
| A3_DQ185900 | ---RTFGCSWEFIPVDDGWGESSL | 1292 |
| A2_X73423 | ---RTFGCSWEFIPVDDGWGESSL | 1296 |
| A8_KM233166 | ---RTFGCSWEFIPVDDGWGESSQ | 1297 |
| H_KGO15617 | ---RTFGCSWEFIPEENGWQEH-- | 1288 |
| E9_JX424534 | ---NSNGCFWSFIPEENGWQEK-- | 1251 |
| E12_KM370319 | ---NSNGCFWNFISEEHGWQEK-- | 1254 |
| E11_KF861875 | ---NSNGCFWNFISEEHGWQEK-- | 1252 |
| E10_KF861917 | ---NSNGCFWNFISEEHGWQEK-- | 1252 |
| E7_JN695729 | ---NSNGCFWNFISEEHGWQEK-- | 1252 |
| E8_JN695730 | ---NSNGCFWNFISEEHGWQEK-- | 1252 |
| E5_AB037711 | ---NSNGCFWNFISEEHGWQEK-- | 1251 |
| E6_AM695759 | ---NSNGFFWNFISEEHGWQEK-- | 1252 |
| E4_AB088207 | ---NSNGFFWNFISEEHGWQEK-- | 1252 |
| E3_EF028403 | ---NSNGCFWNFISEEHGWQEK-- | 1252 |
| E1_Q00496 | ---NSNGCFWNFISEEHGWQEK-- | 1252 |
| E2_EF028404 | ---NSNGCFWNFISEEHGWQEK-- | 1252 |
| F7_GU213233 | ---RNNGCFWSFISKEHGWQE--- | 1268 |
| F5_GU213211 | ---SSNGCFWSFISKEHGWQE--- | 1277 |
| F1_Q57236 | ---SSNGCFWSFISKEHGWQEN-- | 1278 |
| F4_GU213214 | ---SSNGCFWSFISKEHGWQE--- | 1277 |
| F2_GU213209 | ---SSNGCFWSFISKEHGWKE--- | 1280 |
| F3_GU213227 | ---SSNGCFWSFISKEHGWQE--- | 1279 |
| F6_M92906 | ---SSNGCFWSSISKENGWKE--- | 1274 |
| T_P04958 | ------ILGCDWYFVPTDEGWTND- | 1315 |

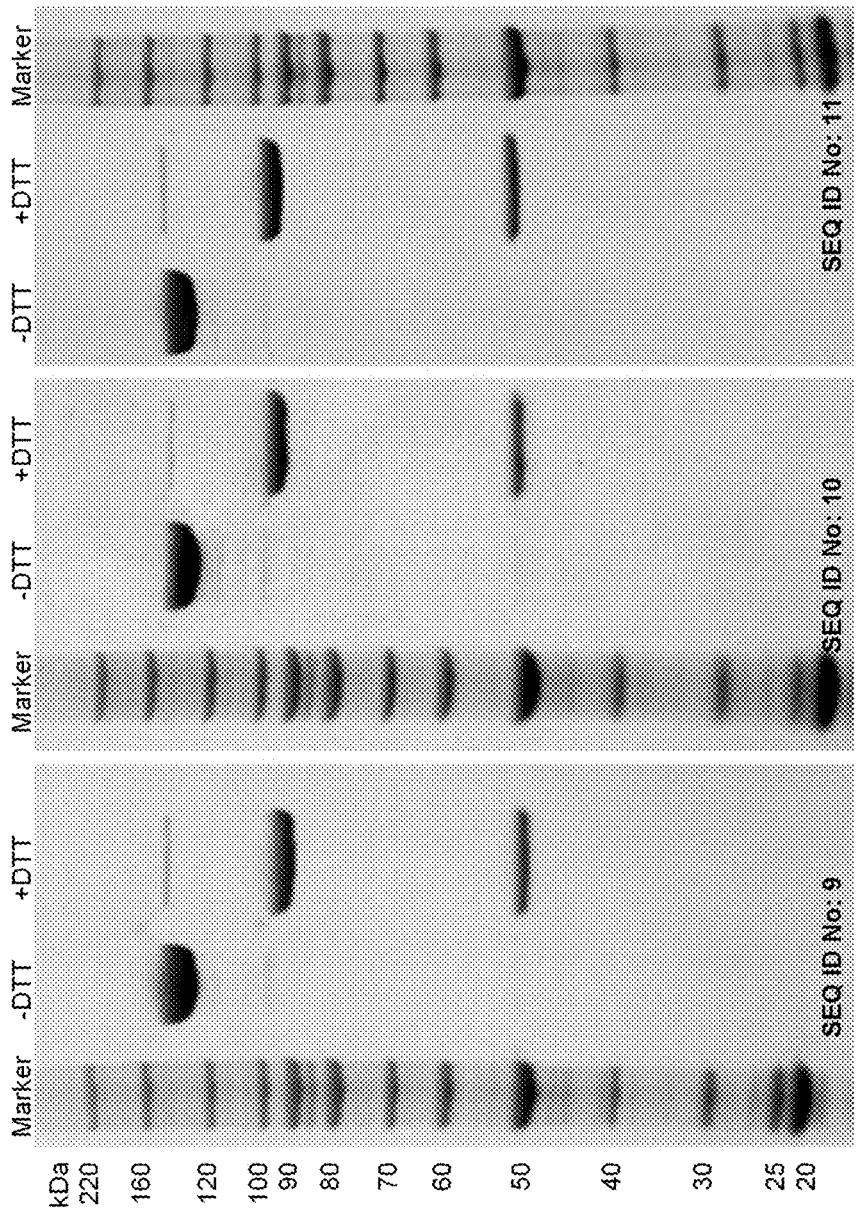

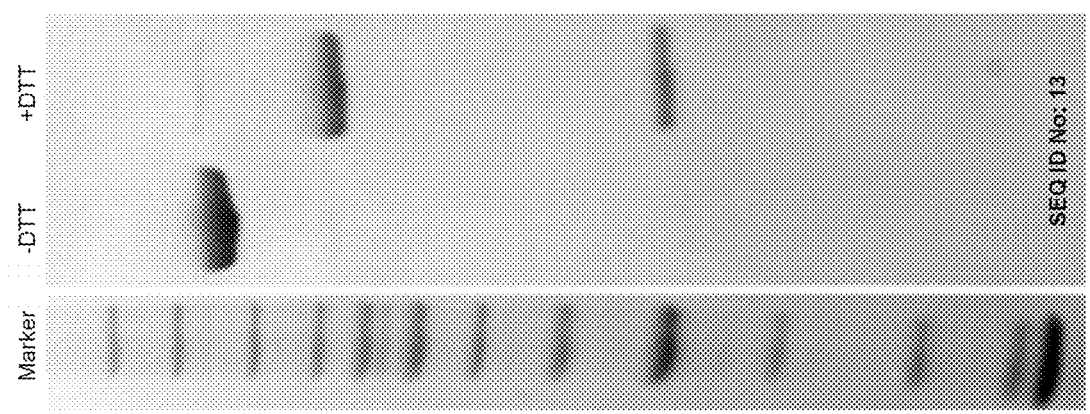
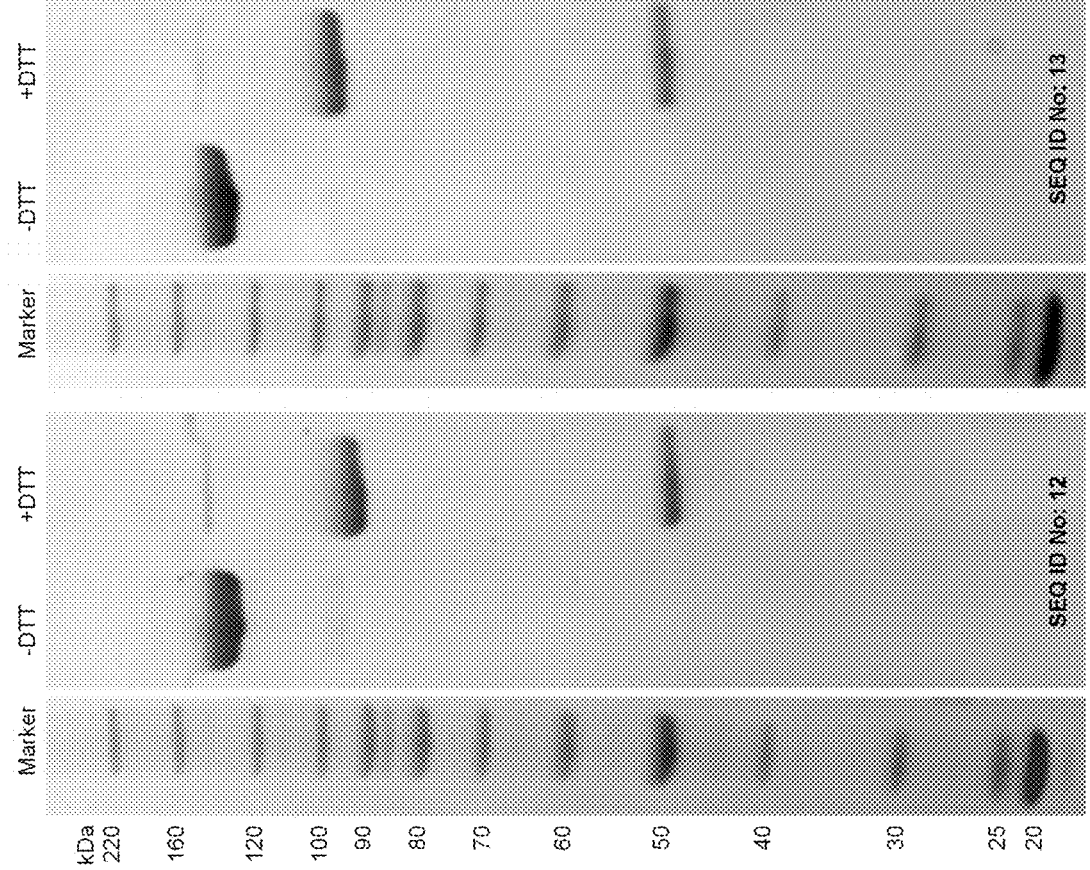

CHIMERIC NEUROTOXINS

CROSS-REFERENCE TO RELATED APPLICATIONS

This application is a division of U.S. application Ser. No. 16/094,254, which is a U.S. national stage filing of International Application No. PCT/EP2017/060821, filed May 5, 2017, which in turn claims priority benefit of United Kingdom Application No. 1607901.4, filed May 5, 2016. Each of these applications is hereby incorporated by reference in its entirety.

SEQUENCE LISTING

The instant application contains a Sequence Listing that has been submitted electronically in XML format and is hereby incorporated by reference in its entirety. The XML copy was created on Jul. 12, 2022, is named 356845SequenceListing.xml and is 160,350 bytes in size.

FIELD OF THE INVENTION

The present invention relates to chimeric neurotoxins with enhanced properties and their use in therapy.

BACKGROUND

Bacteria in the genus *Clostridia* produce highly potent and specific protein toxins, which can poison neurons and other cells to which they are delivered. Examples of such clostridial toxins include the neurotoxins produced by *C. tetani* (TeNT) and by *C. botulinum* (BoNT) serotypes A-G, as well as those produced by *C. baratii* and *C. butyricum*.

Among the clostridial neurotoxins are some of the most potent toxins known. By way of example, botulinum neurotoxins have median lethal dose (LD50) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site, that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the HC domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins.

Accordingly, once delivered to a desired target cell, the non-cytotoxic protease is capable of inhibiting cellular secretion from the target cell. The L-chain proteases of clostridial neurotoxins are non-cytotoxic proteases that cleave SNARE proteins.

In view of the ubiquitous nature of SNARE proteins, clostridial neurotoxins such as botulinum toxin have been successfully employed in a wide range of therapies.

By way of example, we refer to William J. Lipham, Cosmetic and Clinical Applications of Botulinum Toxin (Slack, Inc., 2004), which describes the use of clostridial neurotoxins, such as botulinum neurotoxins (BoNTs), BoNT/A, BoNT/B, BoNT/C1, BoNT/D, BoNT/E, BoNT/F and BoNT/G, and tetanus neurotoxin (TeNT), to inhibit neuronal transmission in a number of therapeutic and cosmetic or aesthetic applications—for example, marketed botulinum toxin products are currently approved as therapeutics for indications including focal spasticity, upper limb spasticity, lower limb spasticity, cervical dystonia, blepharospasm, hemifacial spasm, hyperhidrosis of the axillae, chronic migraine, neurogenic detrusor overactivity, glabellar lines, and severe lateral canthal lines. In addition, clostridial neurotoxin therapies are described for treating neuromuscular disorders (see U.S. Pat. No. 6,872,397); for treating uterine disorders (see US 2004/0175399); for treating ulcers and gastroesophageal reflux disease (see US 2004/0086531); for treating dystonia (see U.S. Pat. No. 6,319,505); for treating eye disorders (see US 2004/0234532); for treating blepharospasm (see US 2004/0151740); for treating strabismus (see US 2004/0126396); for treating pain (see U.S. Pat. Nos. 6,869,610, 6,641,820, 6,464,986, and 6,113,915); for treating fibromyalgia (see U.S. Pat. No. 6,623,742, US 2004/0062776); for treating lower back pain (see US 2004/0037852); for treating muscle injuries (see U.S. Pat. No. 6,423,319); for treating sinus headache (see U.S. Pat. No. 6,838,434); for treating tension headache (see U.S. Pat. No. 6,776,992); for treating headache (see U.S. Pat. No. 6,458,365); for reduction of migraine headache pain (see U.S. Pat. No. 5,714,469); for treating cardiovascular diseases (see U.S. Pat. No. 6,767,544); for treating neurological disorders such as Parkinson's disease (see U.S. Pat. Nos. 6,620,415, 6,306,403); for treating neuropsychiatric disorders (see US 2004/0180061, US 2003/0211121); for treating endocrine disorders (see U.S. Pat. No. 6,827,931); for treating thyroid disorders (see U.S. Pat. No. 6,740,321); for treating cholinergic influenced sweat gland disorders (see U.S. Pat. No. 6,683,049); for treating diabetes (see U.S. Pat. Nos. 6,337,075, 6,416,765); for treating a pancreatic disorder (see U.S. Pat. Nos. 6,261,572, 6,143,306); for treating cancers such as bone tumors (see U.S. Pat. Nos. 6,565,870, 6,368,605, 6,139,845, US 2005/0031648); for treating otic disorders (see U.S. Pat. Nos. 6,358,926, 6,265,379); for treating autonomic disorders such as gastrointestinal muscle disorders and other smooth muscle dysfunction (see U.S. Pat. No. 5,437,291); for treatment of skin lesions associated with cutaneous cell-proliferative disorders (see U.S. Pat. No. 5,670,484); for management of neurogenic inflammatory disorders (see U.S. Pat. No. 6,063,768); for reducing hair loss and stimulating hair growth (see U.S. Pat. No. 6,299, 893); for treating downturned mouth (see U.S. Pat. No. 6,358,917); for reducing appetite (see US 2004/40253274); for dental therapies and procedures (see US 2004/0115139); for treating neuromuscular disorders and conditions (see US 2002/0010138); for treating various disorders and conditions and associated pain (see US 2004/0013692); for treating conditions resulting from mucus hypersecretion such as asthma and COPD (see WO 00/10598); and for treating non-neuronal conditions such as inflammation, endocrine conditions, exocrine conditions, immunological conditions, cardiovascular conditions, bone conditions (see WO 01/21213). All of the above publications are hereby incorporated by reference in their entirety.

The use of non-cytotoxic proteases such as clostridial neurotoxins (e.g. BoNTs and TeNT) in therapeutic and cosmetic treatments of humans and other mammals is anticipated to expand to an ever-widening range of diseases and ailments that can benefit from the properties of these toxins.

Currently all approved drugs/cosmetic preparations comprising BoNTs contain naturally occurring neurotoxins purified from clostridial strains (BoNT/A in the case of DYSPORT®, BOTOX® or XEOMIN®, and BoNT/B in the case of MYOBLOC®).

Recombinant technology offers the possibility of changing or optimizing the properties of neurotoxins through the introduction of modifications to its sequence and/or structure. In particular, chimeric neurotoxins in which the $H_C$ domain or the $H_{CC}$ subdomain is replaced by a $H_C$ domain or $H_{CC}$ subdomain from a different neurotoxin have been produced.

Rummel et al, 2011 (Exchange of the $H_{CC}$ domain mediating double receptor recognition improves the pharmacodynamic properties of botulinum neurotoxin. FEBS Journal, 278(23), 4506-4515) generated various active full-length hybrid neurotoxins, including AABB, AACC and BBAA chimera (letters represent the serotype origin of each of the four domains: L, $H_N$, $H_{CN}$, $H_{CC}$). The AABB chimera was found to be more potent than BoNT/A in a mouse phrenic nerve hemidiaphragm assay, while the AACC only retained 10% of the potency of BoNT/A. The BBAA chimera retained 85% of the potency of BoNT/A and was equipotent to BoNT/B.

Wang et al, 2008 (Novel chimeras of botulinum neurotoxins A and E unveil contributions from the binding, translocation, and protease domains to their functional characteristics. Journal of Biological Chemistry, 283(25), 16993-17002) generated AE ($LH_N$ from BoNT/A and $H_C$ from BoNT/E) and EA ($LH_N$ from BoNT/E and $H_C$ from BoNT/A) chimeric neurotoxins, adding a linker in the case of the AE chimera between the $LH_N$ and $H_C$ domains to increase flexibility. Both were able to cause a paralysis in a mouse phrenic nerve hemidiaphragm assay as well as in vivo.

Wang et al., 2012a (Longer-acting and highly potent chimaeric inhibitors of excessive exocytosis created with domains from botulinum neurotoxin A and B. Biochemical Journal, 444(1), 59-67) generated AB ($LH_N$ from BoNT/A and $H_C$ from BoNT/B, with a linker to improve folding) and BA ($LH_N$ from BoNT/B and $H_C$ from BoNT/A) chimeric neurotoxins. The AB chimera induced a more prolonged neuromuscular paralysis than BoNT/A in mice. The BA chimera was able to reduce exocytosis from non-neuronal cells.

Wang et al, 2012b (Novel chimeras of botulinum and tetanus neurotoxins yield insights into their distinct sites of neuroparalysis. The FASEB Journal, 26(12), 5035-5048) generated ATx ($LH_N$ from BoNT/A and $H_C$ from TeNT), TxA ($LH_N$ from TeNT and $H_C$ from BoNT/A), ETx ($LH_N$ from BoNT/E and $H_C$ from TeNT) and TxE ($LH_N$ from TeNT and $H_C$ from BoNT/E) chimera. The information provided with respect to the protein sequence of these prior art chimeric neurotoxins is summarised in table 1 below:

TABLE 1

$LH_N$ and $H_C$ domains in prior art chimeric neurotoxins

| | Chimera | $LH_N$ | $H_C$ |
|---|---|---|---|
| Rummel, 2011 | AABB | A | B: 871-1304 |
| | AACC | A | C: 871-1296 |
| | BBAA | B | A: 858-1283 |
| Wang, 2008 | AE | A: 1-874 (+ELGGGGSEL linker) | E: 845-1252 |
| | EA | E: 1-844 (+DI linker) | A: 871-1296 |
| Wang, 2012(a) | AB | A: 1-874 (+ELGGGGSEL linker) | B: 858-1283 |
| | BA | B: 1-861 (+DI linker) | A: 871-1296 |
| Wang, 2012(b) | ATx | A: 1-877 | Tx: 879-1315 |
| | TxA | Tx: 1-882 (+DI linker) | A: 871-1296 |
| | ETx | E: 1-844 (+DI linker) | Tx: 879-1315 |
| | TxE | Tx: 1-882 (+EL linker) | E: 845-1252 |

However, there still exists a need for an optimized design of chimeric neurotoxins allowing for improved therapeutic properties.

The present invention solves the above problem by providing chimeric neurotoxins, as specified in the claims.

SUMMARY OF THE INVENTION

In one aspect, the invention provides a chimeric neurotoxin comprising a $LH_N$ domain from a first neurotoxin covalently linked to a $H_C$ domain from a second neurotoxin, wherein the first and second neurotoxins are different, wherein the C-terminal amino acid residue of the $LH_N$ domain corresponds to the first amino acid residue of the $3_{10}$ helix separating the $LH_N$ and $H_C$ domains in the first neurotoxin, and wherein the N-terminal amino acid residue of the $H_C$ domain corresponds to the second amino acid residue of the $3_{10}$ helix separating the $LH_N$ and $H_C$ domains in the second neurotoxin.

In a second aspect, the invention provides a nucleotide sequence encoding a chimeric neurotoxin according to the invention.

In a third aspect, the invention provides a vector comprising a nucleotide sequence according to the invention.

In a fourth aspect, the invention provides a cell comprising a nucleotide sequence or a vector according to the invention.

In a fifth aspect, the invention provides a pharmaceutical composition comprising a chimeric neurotoxin according to the invention.

In a sixth aspect, the invention provides a chimeric neurotoxin according to the invention for use in therapy.

In a seventh aspect, the invention provides a non-therapeutic use of a chimeric neurotoxin according to the invention for treating an aesthetic or cosmetic condition.

DETAILED DESCRIPTION

In one aspect, the invention provides a chimeric neurotoxin comprising a $LH_N$ domain from a first neurotoxin covalently linked to a $H_C$ domain from a second neurotoxin, wherein the first and second neurotoxins are different,
  wherein the C-terminal amino acid residue of the $LH_N$ domain corresponds to the first amino acid residue of the $3_{10}$ helix separating the $LH_N$ and $H_C$ domains in the first neurotoxin, and wherein the N-terminal amino acid residue of the $H_C$ domain corresponds to the second amino acid residue of the $3_{10}$ helix separating the $LH_N$ and $H_C$ domains in the second neurotoxin.

As used herein, the term "a", "an" and "the" can mean one or more.

The term "neurotoxin" as used herein means any polypeptide that enters a neuron and inhibits neurotransmitter release. This process encompasses the binding of the neurotoxin to a low or high affinity receptor, the internalisation of the neurotoxin, the translocation of the endopeptidase portion of the neurotoxin into the cytoplasm and the enzymatic modification of the neurotoxin substrate. More specifically, the term "neurotoxin" encompasses any polypeptide produced by *Clostridium* bacteria (clostridial neurotoxins) that enters a neuron and inhibits neurotransmitter release, and such polypeptides produced by recombinant technologies or chemical techniques. It is this dichain form that is the active form of the toxin. The two chains are termed the heavy chain (H-chain), which has a molecular mass of approximately 100 kDa, and the light chain (L-chain), which has a molecular mass of approximately 50 kDa. Preferably, the first and second neurotoxins are clostridial neurotoxins.

An example of a BoNT/A neurotoxin amino acid sequence is provided as SEQ ID NO: 1 (UNIPROT® accession number A5HZZ9). An example of a BoNT/B neurotoxin amino acid sequence is provided as SEQ ID NO: 2 (UNIPROT® accession number B1INP5). An example of a BoNT/C neurotoxin amino acid sequence is provided as SEQ ID NO: 3 (UNIPROT® accession number P18640). An example of a BoNT/D neurotoxin amino acid sequence is provided as SEQ ID NO: 4 (UNIPROT® accession number P19321). An example of a BoNT/E neurotoxin amino acid sequence is provided as SEQ ID NO: 5 (UNIPROT® accession number Q00496). An example of a BoNT/F neurotoxin amino acid sequence is provided as SEQ ID NO: 6 (UNIPROT® accession number Q57236). An example of a BoNT/G neurotoxin amino acid sequence is provided as SEQ ID NO: 7 (UNIPROT® accession number Q60393). An example of a TeNT neurotoxin amino acid sequence is provided as SEQ ID NO: 8 (UNIPROT® accession number P04958). The amino acid sequences of said neurotoxins are shown in the alignment of FIG. 1 below, along with the sequences of other neurotoxins (i.e. SEQ ID NOs: 58 to 91).

The term "chimeric neurotoxin" as used herein means a neurotoxin comprising or consisting of an $LH_N$ domain originating from a first neurotoxin and a $H_C$ domain originating from a second neurotoxin.

The term "$H_C$ domain" as used herein means a functionally distinct region of the neurotoxin heavy chain with a molecular weight of approximately 50 kDa that enables the binding of the neurotoxin to a receptor located on the surface of the target cell. The $H_C$ domain consists of two structurally distinct subdomains, the "$H_{CN}$ subdomain" (N-terminal part of the $H_C$ domain) and the "$H_{CC}$ subdomain" (C-terminal part of the $H_C$ domain), each of which has a molecular weight of approximately 25 kDa.

The term "$LH_N$ domain" as used herein means a neurotoxin that is devoid of the $H_C$ domain and consists of an endopeptidase domain ("L" or "light chain") and the domain responsible for translocation of the endopeptidase into the cytoplasm ($H_N$ domain of the heavy chain).

Reference herein to the "first amino acid residue of the $3_{10}$ helix separating the $LH_N$ and $H_C$ domains in the first neurotoxin" means the N-terminal residue of the $3_{10}$ helix separating the $LH_N$ and $H_C$ domains.

Reference herein to the "second amino acid residue of the $3_{10}$ helix separating the $LH_N$ and $H_C$ domains in the second neurotoxin" means the amino acid residue following the N-terminal residue of the $3_{10}$ helix separating the $LH_N$ and $H_C$ domains.

A "$3_{10}$ helix" is a type of secondary structure found in proteins and polypeptides, along with α-helices, β-sheets and reverse turns. The amino acids in a $3_{10}$ helix are arranged in a right-handed helical structure where each full turn is completed by three residues and ten atoms that separate the intramolecular hydrogen bond between them. Each amino acid corresponds to a 1200 turn in the helix (i.e., the helix has three residues per turn), and a translation of 2.0 Å (=0.2 nm) along the helical axis, and has 10 atoms in the ring formed by making the hydrogen bond. Most importantly, the N—H group of an amino acid forms a hydrogen bond with the C=O group of the amino acid three residues earlier; this repeated i+3→i hydrogen bonding defines a $3_{10}$ helix. A $3_{10}$ helix is a standard concept in structural biology with which the skilled person is familiar.

This $3_{10}$ helix corresponds to four residues which form the actual helix and two cap (or transitional) residues, one at each end of these four residues. The term "$3_{10}$ helix separating the $LH_N$ and $H_C$ domains" as used herein consists of those 6 residues.

Through carrying out structural analyses and sequence alignments, the inventor identified a $3_{10}$ helix separating the $LH_N$ and $H_C$ domains in tetanus and botulinum neurotoxins. This $3_{10}$ helix is surrounded by an α-helix at its N-terminus (i.e. at the C-terminal part of the $LH_N$ domain) and by a β-strand at its C-terminus (i.e. at the N-terminal part of the $H_C$ domain). The first (N-terminal) residue (cap or transitional residue) of the $3_{10}$ helix also corresponds to the C-terminal residue of this α-helix.

The $3_{10}$ helix separating the $LH_N$ and $H_C$ domains can be for example determined from publically available crystal structures of botulinum neurotoxins, for example 3BTA and 1EPW from RCSB Protein Data Bank for botulinum neurotoxins A1 and B1 respectively.

In silico modelling and alignment tools which are publically available can also be used to determine the location of the $3_{10}$ helix separating the $LH_N$ and $H_C$ domains in other neurotoxins, for example the homology modelling servers LOOPP (Learning, Observing and Outputting Protein Patterns), PHYRE (Protein Homology/analogY Recognition Engine) and Rosetta, the protein superposition server SuperPose, the alignment program Clustal Omega, and a number of other tools/services listed at the Internet Resources for Molecular and Cell Biologists. The inventor found in particular that the region around the "$H_N$/$H_{CN}$" junction is structurally highly conserved which renders it an ideal region to superimpose different serotypes.

For example, the following methodology was used by the inventor to determine the sequence of this $3_{10}$ helix in other neurotoxins:

1. The structural homology modelling tool LOOP was used to obtain a predicted structure of all BoNT serotypes and TeNT based on the BoNT/A1 crystal structure (3BTA.pdb);
2. The structural (pdb) files thus obtained were edited to include only the N-terminal end of the $H_{CN}$ domain and about 80 residues before it (which are part of the $H_N$ domain), thereby retaining the "$H_N$/$H_{CN}$" region which is structurally highly conserved;
3. The protein superposition server SuperPose was used to superpose each serotype onto the 3BTA.pdb structure;

4. The superposed pdb files were inspected to locate the $3_{10}$ helix at the start of the Hc domain of BoNT/A1, and corresponding residues in the other serotype were then identified.
5. All BoNT serotype sequences were aligned with Clustal Omega in order to check that corresponding residues were correct.

Examples of $LH_N$, $H_C$ and $3_{10}$ helix domains determined by this method are presented in table 2.

TABLE 2

$LH_N$, $H_C$ and $3_{10}$ helix domains

| Neurotoxin | Accession Number | $LH_N$ | $H_C$ | $3_{10}$ helix | SEQ ID NO ($3_{10}$ helix) |
|---|---|---|---|---|---|
| BoNT/A1 | A5HZZ9 | 1-872 | 873-1296 | $^{872}$NIINTS$^{877}$ | 14 |
| BoNT/A2 | X73423 | 1-872 | 873-1296 | $^{872}$NIVNTS$^{877}$ | 15 |
| BoNT/A3 | DQ185900 | 1-872 | 873-1292 | $^{872}$NIVNTS$^{877}$ | 16 |
| BoNT/A4 | EU341307 | 1-872 | 873-1296 | $^{872}$NITNAS$^{877}$ | 17 |
| BoNT/A5 | EU679004 | 1-872 | 873-1296 | $^{872}$NIINTS$^{877}$ | 18 |
| BoNT/A6 | FJ981696 | 1-872 | 873-1296 | $^{872}$NIINTS$^{877}$ | 19 |
| BoNT/A7 | JQ954969 | 1-872 | 873-1296 | $^{872}$NIINTS$^{877}$ | 20 |
| BoNT/A8 | KM233166 | 1-872 | 873-1297 | $^{872}$NITNTS$^{877}$ | 21 |
| BoNT/B1 | B1INP5 | 1-859 | 860-1291 | $^{859}$EILNNI$^{864}$ | 22 |
| BoNT/B2 | AB084152 | 1-859 | 860-1291 | $^{859}$EILNNI$^{864}$ | 23 |
| BoNT/B3 | EF028400 | 1-859 | 860-1291 | $^{859}$EILNNI$^{864}$ | 24 |
| BoNT/B4 | EF051570 | 1-859 | 860-1291 | $^{859}$EILNNI$^{864}$ | 25 |
| BoNT/B5 | EF033130 | 1-859 | 860-1291 | $^{859}$DILNNI$^{864}$ | 26 |
| BoNT/B6 | AB302852 | 1-859 | 860-1291 | $^{859}$EILNNI$^{864}$ | 27 |
| BoNT/B7 | JQ354985 | 1-859 | 860-1291 | $^{859}$EILNNI$^{864}$ | 28 |
| BoNT/B8 | JQ964806 | 1-859 | 860-1292 | $^{859}$EILNNI$^{864}$ | 29 |
| BoNT/C1 | P18640 | 1-867 | 868-1291 | $^{867}$NINDSK$^{872}$ | 30 |
| BoNT/CD | AB200360 | 1-867 | 868-1280 | $^{867}$SINDSK$^{872}$ | 31 |
| BoNT/DC | AB745660 | 1-863 | 864-1276 | $^{863}$SINDSK$^{868}$ | 32 |
| BoNT/D | P19321 | 1-863 | 864-1276 | $^{863}$SINDSK$^{868}$ | 33 |
| BoNT/E1 | Q00496 | 1-846 | 847-1252 | $^{846}$RIKSSS$^{851}$ | 34 |
| BoNT/E2 | EF028404 | 1-846 | 847-1252 | $^{846}$RIKSSS$^{851}$ | 35 |
| BoNT/E3 | EF028403 | 1-846 | 847-1252 | $^{846}$RIKSSS$^{851}$ | 36 |
| BoNT/E4 | AB088207 | 1-846 | 847-1252 | $^{846}$RIKSSS$^{851}$ | 37 |
| BoNT/E5 | AB037711 | 1-846 | 847-1251 | $^{846}$RIKSSS$^{851}$ | 38 |
| B0NT/E6 | AM695759 | 1-846 | 847-1252 | $^{846}$RIKSSS$^{851}$ | 39 |
| BoNT/E7 | JN695729 | 1-846 | 847-1252 | $^{846}$RIKSSS$^{851}$ | 40 |
| BoNT/E8 | JN695730 | 1-846 | 847-1252 | $^{846}$RIKSSS$^{851}$ | 41 |
| BoNT/E9 | JX424534 | 1-846 | 847-1251 | $^{846}$RIKSSS$^{851}$ | 42 |
| BoNT/E10 | KF861917 | 1-846 | 847-1252 | $^{846}$RIKSSS$^{851}$ | 43 |
| BoNT/E11 | KF861875 | 1-846 | 847-1252 | $^{846}$RIKSSS$^{851}$ | 44 |
| BoNT/E12 | KM370319 | 1-846 | 847-1254 | $^{846}$RIKSSS$^{851}$ | 45 |
| BoNT/F1 | Q57236 | 1-865 | 866-1278 | $^{865}$KIKDNS$^{870}$ | 46 |
| BoNT/F2 | GU213209 | 1-865 | 866-1280 | $^{865}$KIKDSS$^{870}$ | 47 |
| BoNT/F3 | GU213227 | 1-865 | 866-1279 | $^{865}$KIKDSS$^{870}$ | 48 |
| BoNT/F4 | GU213214 | 1-865 | 866-1277 | $^{865}$KIKDNC$^{870}$ | 49 |
| BoNT/F5 | GU213211 | 1-862 | 863-1277 | $^{862}$KIKDSS$^{867}$ | 50 |
| B0NT/F6 | M92906 | 1-864 | 865-1274 | $^{864}$KIKDSS$^{869}$ | 51 |
| BoNT/F7 | GU213233 | 1-856 | 857-1268 | $^{856}$KIKDSS$^{861}$ | 52 |
| BoNT/G | Q60393 | 1-864 | 865-1297 | $^{864}$NISSNA$^{869}$ | 53 |
| BoNT/H | KG015617 | 1-860 | 861-1288 | $^{860}$ELKYNC$^{865}$ | 54 |
| TeNT | P04958 | 1-880 | 881-1315 | $^{880}$ILKKST$^{885}$ | 55 |

Using structural analysis and sequence alignments, the inventor found that the β-strand following the $3_{10}$ helix separating the $LH_N$ and $H_C$ domains is a conserved structure in all botulinum and tetanus neurotoxins and starts at the 8$^{th}$ residue when starting from the first residue of the $3_{10}$ helix separating the $LH_N$ and $H_C$ domains (e.g., at residue 879 for BoNT/A1).

According to an alternative definition, the first aspect of the invention provides a chimeric neurotoxin comprising an $LH_N$ domain from a first neurotoxin covalently linked to a $H_C$ domain from a second neurotoxin, wherein the first and second neurotoxins are different, wherein the C-terminal amino acid residue of the $LH_N$ domain corresponds to the eighth amino acid residue N-terminally to the β-strand located at the beginning (N-term) of the $H_C$ domain in the first neurotoxin, and wherein the N-terminal amino acid residue of the $H_C$ domain corresponds to the seventh amino acid residue N-terminally to the β-strand located at the beginning (N-term) of the $H_C$ domain in the second neurotoxin.

According to yet another definition, the first aspect of the invention provides a chimeric neurotoxin comprising a $LH_N$ domain from a first neurotoxin covalently linked to a $H_C$ domain from a second neurotoxin, wherein the first and second neurotoxins are different, wherein the C-terminal amino acid residue of the $LH_N$ domain corresponds to the C-terminal amino acid residue of the α-helix located at the end (C-term) of $LH_N$ domain in the first neurotoxin, and wherein the N-terminal amino acid residue of the $H_C$ domain corresponds to the amino acid residue immediately C-terminal to the C-terminal amino acid residue of the α-helix located at the end (C-term) of $LH_N$ domain in the second neurotoxin.

The rationale of the design process of the chimeric neurotoxins according to the invention was to try to ensure that the secondary structure was not compromised and thereby minimise any changes to the tertiary structure and to the function of each domain.

In some of the prior art chimeric neurotoxins, a linker is required between the $LH_N$ and $H_C$ domains (see table 1), presumably to ensure acceptable expression and purification.

Without wishing to be bound by theory, it is hypothesized that structuring chimeric neurotoxins in the form of proteins which have a tertiary structure closely mimicking the tertiary structure of natural neurotoxins will facilitate their solubility.

Without wishing to be bound by theory, it is further hypothesized that the fact of not disrupting the four central amino acid residues of the $3_{10}$ helix in the chimeric neurotoxin ensures an optimal conformation for the chimeric neurotoxin, thereby allowing for the chimeric neurotoxin to exert its functions to their full capacity.

In fact, the inventor has surprisingly found that retaining solely the first amino acid residue of the $3_{10}$ helix of the first neurotoxin and the second amino acid residue of the $3_{10}$ helix onwards of second neurotoxin not only allows the production of soluble and functional chimeric neurotoxins, but further leads to improved properties over other chimeric neurotoxins, in particular an increased potency, an increased safety ratio and/or a longer duration of action.

Undesired effects of a neurotoxin (caused by diffusion of the neurotoxin away from the site of administration) can be assessed experimentally by measuring percentage bodyweight loss in a relevant animal model (e.g. a mouse, where loss of bodyweight is detected within seven days of administration). Conversely, desired on-target effects of a neurotoxin can be assessed experimentally by Digital Abduction Score (DAS) assay, a measurement of muscle paralysis. The DAS assay may be performed by injection of 20 μL of neurotoxin, formulated in Gelatin Phosphate Buffer, into the mouse gastrocnemius/soleus complex, followed by assessment of Digital Abduction Score using the method of Aoki (Aoki K R, Toxicon 39: 1815-1820; 2001).

In the DAS assay, mice are suspended briefly by the tail in order to elicit a characteristic startle response in which the mouse extends its hind limbs and abducts its hind digits. Following neurotoxin injection, the varying degrees of digit abduction are scored on a five-point scale (0=normal to 4=maximal reduction in digit abduction and leg extension).

The Safety Ratio of a neurotoxin may then be expressed as the ratio between the amount of neurotoxin required for a 10% drop in a bodyweight of a mouse (measured at peak effect within the first seven days after dosing in a mouse) and the amount of neurotoxin required for a DAS score of 2. High Safety Ratio scores are therefore desired, and indicate a neurotoxin that is able to effectively paralyse a target muscle with little undesired off-target effects.

A high safety ratio is particularly advantageous in therapy because it represents an increase in the therapeutic index. In other words, this means that reduced dosages can be used compared to known clostridial toxin therapeutics and/or that increased dosages can be used without any additional effects. The possibility to use higher doses of neurotoxin without additional effects is particularly advantageous as higher doses usually lead to a longer duration of action of the neurotoxin.

The Potency of a neurotoxin may be expressed as the minimal dose of neurotoxin which leads to a given DAS score when administered to a mouse gastrocnemius/soleus complex, for example a DAS score of 2 ($ED_{50}$ dose) or a DAS score of 4. The Potency of a neurotoxin may be also expressed as the $EC_{50}$ dose in a cellular assay measuring SNARE cleavage by the neurotoxin, for example the $EC_{50}$ dose in a cellular assay measuring SNAP-25 cleavage by a chimeric BoNT/AB neurotoxin.

The duration of action of a neurotoxin may be expressed as the time required for retrieving a DAS score of 0 after administration of a given dose of neurotoxin, for example the minimal dose of neurotoxin leading to a DAS score of 4, to a mouse gastrocnemius/soleus complex.

In one embodiment, the first neurotoxin is a Botulinum Neurotoxin (BoNT) serotype A, serotype B, serotype C, serotype D, serotype E, serotype F or serotype G or a Tetanus Neurotoxin (TeNT), and the second neurotoxin is a Botulinum Neurotoxin (BoNT) serotype A, serotype B, serotype C, serotype D, serotype E, serotype F or serotype G or a Tetanus Neurotoxin (TeNT). In a preferred embodiment, the first neurotoxin is a Botulinum Neurotoxin (BoNT) serotype A, serotype B or a serotype C, and the second neurotoxin is a Botulinum Neurotoxin (BoNT) serotype A, serotype B or a serotype C.

Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

Preferably, the first and second neurotoxins are Botulinum Neurotoxins from different serotypes. In another embodiment, either the first or second neurotoxin is a Botulinum Neurotoxin and the other neurotoxin is a Tetanus neurotoxin.

Using an "XY" representation according to which X is the $LH_N$ domain and Y is the $H_C$ domain, the following chimeric neurotoxins are embodiments of the present invention:
AB, AC, AD, AE, AF, AG, ATx,
BA, BC, BD, BE, BF, BG, BTx,
CA, CB, CD, CE, CF, CG, CTx,
DA, DB, DC, DE, DF, DG, DTx,
EA, EB, EC, ED, EF, EG, ETx,
FA, FB, FC, FD, FE, FG, FTx,
GA, GB, GC, GD, GE, GF, FTx,
TxA, TxB, TxC, TxD, TxE, TxF, TxG,
wherein A, B, C, D, E, F, G and Tx are respectively Botulinum Neurotoxin (BoNT) serotype A, serotype B, serotype C, serotype D, serotype E, serotype F, serotype G and Tetanus Neurotoxin (TeNT).

Yet, using the same "XY" representation as described above, the following chimeric neurotoxins are preferred embodiments of the present invention:
AB, AC,
BA, BC,
CA, CB,
wherein A, B, C, are respectively Botulinum Neurotoxin (BoNT) serotype A, serotype B, and serotype C.

In one embodiment, the $LH_N$ domain from the first neurotoxin corresponds to:
amino acid residues 1 to 872 of SEQ ID NO: 1, or a polypeptide sequence having at least 70% sequence identity thereto,
amino acid residues 1 to 859 of SEQ ID NO: 2, or a polypeptide sequence having at least 70% sequence identity thereto,
amino acid residues 1 to 867 of SEQ ID NO: 3, or a polypeptide sequence having at least 70% sequence identity thereto,
amino acid residues 1 to 863 of SEQ ID NO: 4, or a polypeptide sequence having at least 70% sequence identity thereto,
amino acid residues 1 to 846 of SEQ ID NO: 5, or a polypeptide sequence having at least 70% sequence identity thereto,
amino acid residues 1 to 865 of SEQ ID NO: 6, or a polypeptide sequence having at least 70% sequence identity thereto,
amino acid residues 1 to 864 of SEQ ID NO: 7, or a polypeptide sequence having at least 70% sequence identity thereto G, or
amino acid residues 1 to 880 of SEQ ID NO: 8, or a polypeptide sequence having at least 70% sequence identity thereto.
and the $H_C$ domain from the second neurotoxin corresponds to:
amino acid residues 873 to 1296 of SEQ ID NO: 1, or a polypeptide sequence having at least 70% sequence identity thereto,
amino acid residues 860 to 1291 of SEQ ID NO: 2, or a polypeptide sequence having at least 70% sequence identity thereto,
amino acid residues 868 to 1291 of SEQ ID NO: 3, or a polypeptide sequence having at least 70% sequence identity thereto,
amino acid residues 864 to 1276 of SEQ ID NO: 4, or a polypeptide sequence having at least 70% sequence identity thereto,
amino acid residues 847 to 1251 of SEQ ID NO: 5, or a polypeptide sequence having at least 70% sequence identity thereto,
amino acid residues 866 to 1275 of SEQ ID NO: 6, or a polypeptide sequence having at least 70% sequence identity thereto,
amino acid residues 865 to 1297 of SEQ ID NO: 7, or a polypeptide sequence having at least 70% sequence identity thereto, or
amino acid residues 881 to 1315 of SEQ ID NO: 8, or a polypeptide sequence having at least 70% sequence identity thereto.

The "percent sequence identity" between two or more nucleic acid or amino acid sequences is a function of the number of identical nucleotides/amino acids at identical positions shared by the aligned sequences. Thus, % identity may be calculated as the number of identical nucleotides/amino acids at each position in an alignment divided by the total number of nucleotides/amino acids in the aligned sequence, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, in particular a global alignment mathematical algorithm (Needleman and Wunsch, J. Mol. Biol. 48(3), 443-453, 1972) such as BLAST, which will be familiar to a skilled person.

The first or second neurotoxin can be a mosaic neurotoxin. The term "mosaic neurotoxin" as used in this context refers to a naturally occurring clostridial neurotoxin that comprises at least one functional domain from another type of clostridial neurotoxins (e.g. a clostridial neurotoxin of a different serotype), said clostridial neurotoxin not usually comprising said at least one functional domain. Examples of mosaic neurotoxins are naturally occurring BoNT/DC and BoNT/CD. BoNT/DC comprises the L chain and $H_N$ domain of serotype D and the $H_C$ domain of serotype C, whereas BoNT/CD consists of the L chain and $H_N$ domain of serotype C and the $H_C$ domain of serotype D.

The first and second neurotoxins can be modified neurotoxins and derivatives thereof, including but not limited to those described below. A modified neurotoxin or derivative may contain one or more amino acids that has been modified as compared to the native (unmodified) form of the neurotoxin, or may contain one or more inserted amino acids that are not present in the native (unmodified) form of the toxin. By way of example, a modified clostridial neurotoxin may have modified amino acid sequences in one or more domains relative to the native (unmodified) clostridial neurotoxin sequence. Such modifications may modify functional aspects of the neurotoxin, for example biological activity or persistence. Thus, in one embodiment, the first neurotoxin and/or the second neurotoxin is a modified neurotoxin, or modified neurotoxin derivative.

A modified neurotoxin retains at least one of the functions of a neurotoxin, selected from the ability to bind to a low or high affinity neurotoxin receptor on a target cell, to translocate the endopeptidase portion of the neurotoxin (light chain) into the cell cytoplasm and to cleave a SNARE protein. Preferably, a modified neurotoxin retains at least two of these functions. More preferably a modified neurotoxin retains these three functions.

A modified neurotoxin may have one or more modifications in the amino acid sequence of the heavy chain (such as a modified $H_C$ domain), wherein said modified heavy chain binds to target nerve cells with a higher or lower affinity than the native (unmodified) neurotoxin. Such modifications in the $H_C$ domain can include modifying residues in the ganglioside binding site of the $H_C$ domain or in the protein (SV2 or synaptotagmin) binding site that alter binding to the ganglioside receptor and/or the protein receptor of the target nerve cell. Examples of such modified neurotoxins are described in WO 2006/027207 and WO 2006/114308, both of which are hereby incorporated by reference in their entirety.

A modified neurotoxin may have one or more modifications in the amino acid sequence of the light chain, for example modifications in the substrate binding or catalytic domain which may alter or modify the SNARE protein specificity of the modified LC. Examples of such modified neurotoxins are described in WO 2010/120766 and US 2011/0318385, both of which are hereby incorporated by reference in their entirety.

A modified neurotoxin may comprise one or more modifications that increases or decreases the biological activity and/or the biological persistence of the modified neurotoxin. For example, a modified neurotoxin may comprise a leucine- or tyrosine-based motif, wherein said motif increases or decreases the biological activity and/or the biological persistence of the modified neurotoxin. Suitable leucine-based motifs include xDxxxLL, xExxxLL, xExxxIL, and xExxxLM (wherein x is any amino acid). Suitable tyrosine-based motifs include Y-x-x-Hy (wherein Hy is a hydrophobic amino acid). Examples of modified neurotoxins comprising leucine- and tyrosine-based motifs are described in WO 2002/08268, which is hereby incorporated by reference in its entirety.

In one embodiment, the first or second neurotoxin is a modified BoNT/A which has an amino acid sequence having at least 70%, preferably at least 75%, 80%, 85%, 90%, 95% or 99% sequence identity to SEQ ID NO: 1.

In one embodiment, the first or second neurotoxin is a modified BoNT/B which has an amino acid sequence having at least 70%, preferably at least 75%, 80%, 85%, 90%, 95% or 99% sequence identity to SEQ ID NO: 2.

In one embodiment, the first or second neurotoxin is a modified BoNT/C which has an amino acid sequence having at least 70%, preferably at least 75%, 80%, 85%, 90%, 95% or 99% sequence identity to SEQ ID NO: 3.

In one embodiment, the first or second neurotoxin is a modified BoNT/D which has an amino acid sequence having at least 70%, preferably at least 75%, 80%, 85%, 90%, 95% or 99% sequence identity to SEQ ID NO: 4.

In one embodiment, the first or second neurotoxin is a modified BoNT/E which has an amino acid sequence having at least 70%, preferably at least 75%, 80%, 85%, 90%, 95% or 99% sequence identity to SEQ ID NO: 5.

In one embodiment, the first or second neurotoxin is a modified BoNT/F which has an amino acid sequence having at least 70%, preferably at least 75%, 80%, 85%, 90%, 95% or 99% sequence identity to SEQ ID NO: 6.

In one embodiment, the first or second neurotoxin is a modified BoNT/G which has an amino acid sequence having at least 70%, preferably at least 75%, 80%, 85%, 90%, 95% or 99% sequence identity to SEQ ID NO: 7.

In one embodiment, the first or second neurotoxin is a modified TeNT which has an amino acid sequence having at least 70%, preferably at least 75%, 80%, 85%, 90%, 95% or 99% sequence identity to SEQ ID NO: 8.

In one embodiment, the second neurotoxin is a BoNT/B. Such a chimeric neurotoxin is referred to herein as a "BoNT/XB neurotoxin".

In a preferred embodiment, the first neurotoxin is a BoNT/A and the second neurotoxin is a BoNT/B. Such a chimeric neurotoxin is referred to herein as a "BoNT/AB neurotoxin". More preferably, the first neurotoxin is a BoNT/A1 and the second neurotoxin is a BoNT/B1. More preferably still, the $LH_N$ domain from a first neurotoxin corresponds to amino acid residues 1 to 872 of BoNT/A1 and the $H_C$ domain from a second neurotoxin corresponds to amino acid residues 860 to 1291 of BoNT/B1. In one preferred embodiment, the $LH_N$ domain from a first neurotoxin corresponds to amino acid residues 1 to 872 of SEQ ID NO: 1 and the $H_C$ domain from a second neurotoxin corresponds to amino acid residues 860 to 1291 of SEQ ID NO: 2.

In other words, a preferred chimeric neurotoxin according to the invention comprises or consists of the amino acid sequence SEQ ID NO:13.

Compared to the BoNT/A serotype, natural BoNT/B is much less potent despite a comparatively greater abundance of its receptor on synaptic vesicles. This is due to a unique amino acid change within the toxin binding site in human synaptotagmin II (Syt II) as compared to rodent (rat/mouse) Syt II (Peng, L., et al., J Cell Sci, 125(Pt 13):3233-42 (2012); Rummel, A. et al, FEBS J 278:4506-4515 (2011).13, 22. As a result of this residue change, human Syt II has greatly diminished binding to natural BoNT/B, as well as to natural BoNT/D-C, and /G.

These findings provide an explanation for the clinical observations that a much higher dose of BoNT/B than BoNT/A (which binds a different receptor) is needed to achieve the same levels of therapeutic effects in patients. In a preferred embodiment of a BoNT/XB or BoNT/AB neurotoxin according to the invention, the $H_C$ domain from a BoNT/B neurotoxin comprises at least one amino acid residue substitution, addition or deletion in the $H_{CC}$ subdomain which has the effect of increasing the binding affinity of BoNT/B neurotoxin for human Syt II as compared to the natural BoNT/B sequence.

Suitable amino acid residue substitution, addition or deletion in the BoNT/B $H_{CC}$ subdomain have been disclosed in WO2013/180799 and in PCT/US2016/024211 which is not yet published (both herein incorporated by reference).

Suitable amino acid residue substitution, addition or deletion in the BoNT/B $H_{CC}$ subdomain include substitution mutations selected from the group consisting of: V1118M; Y1183M; E1191M; E1191I; E1191Q; E1191T; S1199Y; S1199F; S1199L; 51201V; E1191C, E1191V, E1191L, E1191Y, S1199W, S1199E, S1199H, W1178Y, W1178Q, W1178A, W1178S, Y1183C, Y1183P and combinations thereof.

Suitable amino acid residue substitution, addition or deletion in the BoNT/B $H_{CC}$ subdomain further include combinations of two substitution mutations selected from the group consisting of: E1191M and S1199L, E1191M and S1199Y, E1191M and S1199F, E1191Q and S1199L, E1191Q and S1199Y, E1191Q and S1199F, E1191M and S1199W, E1191M and W1178Q, E1191C and S1199W, E1191C and S1199Y, E1191C and W1178Q, E1191Q and S1199W, E1191V and S1199W, E1191V and S1199Y, or E1191V and W1178Q.

Suitable amino acid residue substitution, addition or deletion in the BoNT/B $H_{CC}$ subdomain also include a combination of three substitution mutations which are E1191M, S1199W and W1178Q.

In a preferred embodiment, the suitable amino acid residue substitution, addition or deletion in the BoNT/B $H_{CC}$ subdomain include a combination of two substitution mutations which are E1191M and S1199Y. In other words, a preferred chimeric neurotoxin according to the invention comprises or consists of the amino acid sequence SEQ ID NO: 11 or SEQ ID NO: 12.

In another preferred embodiment, the first neurotoxin is a BoNT/C and the second neurotoxin is a BoNT/B. Such a chimeric neurotoxin is referred to herein as a "BoNT/CB neurotoxin". More preferably, the first neurotoxin is a BoNT/C1 and the second neurotoxin is a BoNT/B1. More preferably still, the $LH_N$ domain from a first neurotoxin corresponds to amino acid residues 1 to 867 of BoNT/C1 and the $H_C$ domain from a second neurotoxin corresponds to amino acid residues 860 to 1291 of BoNT/B1. In one preferred embodiment, the $LH_N$ domain from a first neurotoxin corresponds to amino acid residues 1 to 867 of SEQ ID NO: 3 and the $H_C$ domain from a second neurotoxin corresponds to amino acid residues 860 to 1291 of SEQ ID NO: 2. In a preferred embodiment, the $H_C$ domain from the BoNT/B neurotoxin comprises at least one amino acid residue substitution, addition or deletion in the $H_{CC}$ subdomain which has the effect of increasing the binding affinity of BoNT/B neurotoxin for human Syt II as compared to the natural BoNT/B sequence. Suitable amino acid residue substitution, addition or deletion in the BoNT/B $H_{CC}$ subdomain is as described above.

In a preferred embodiment of a BoNT/XDC neurotoxin (chimeric neurotoxin in which the second neurotoxin is a mosaic BoNT/DC) according to the invention, the $H_C$ domain from a mosaic BoNT/DC neurotoxin comprises at least one amino acid residue substitution, addition or deletion in the $H_{CC}$ subdomain which has the effect of increasing the binding affinity of mosaic BoNT/DC neurotoxin for human Syt II as compared to the natural mosaic BoNT/DC sequence.

In a preferred embodiment of a BoNT/XG neurotoxin according to the invention, the $H_C$ domain from a BoNT/G neurotoxin comprises at least one amino acid residue substitution, addition or deletion in the $H_{CC}$ subdomain which has the effect of increasing the binding affinity of BoNT/G neurotoxin for human Syt II as compared to the natural BoNT/G sequence.

Other preferred neurotoxins according to the invention are as follows.

In a preferred embodiment, the first neurotoxin is a BoNT/A and the second neurotoxin is a BoNT/C. Such a chimeric neurotoxin is referred to herein as a "BoNT/AC neurotoxin". More preferably, the first neurotoxin is a BoNT/A1 and the second neurotoxin is a BoNT/C1. More preferably still, the $LH_N$ domain from a first neurotoxin corresponds to amino acid residues 1 to 872 of BoNT/A1 and the $H_C$ domain from a second neurotoxin corresponds to amino acid residues 868 to 1291 of BoNT/C1. In one preferred embodiment, the $LH_N$ domain from a first neurotoxin corresponds to amino acid residues 1 to 872 of SEQ ID NO: 1 and the $H_C$ domain from a second neurotoxin corresponds to amino acid residues 868 to 1291 of SEQ ID NO: 3.

In another preferred embodiment, the first neurotoxin is a BoNT/B and the second neurotoxin is a BoNT/A. Such a chimeric neurotoxin is referred to herein as a "BoNT/BA neurotoxin". More preferably, the first neurotoxin is a BoNT/B1 and the second neurotoxin is a BoNT/A1. More preferably still, the $LH_N$ domain from a first neurotoxin corresponds to amino acid residues 1 to 859 of BoNT/B1 and the $H_C$ domain from a second neurotoxin corresponds to amino acid residues 873 to 1296 of BoNT/A1. In one preferred embodiment, the $LH_N$ domain from a first neurotoxin corresponds to amino acid residues 1 to 859 of SEQ ID NO: 2 and the $H_C$ domain from a second neurotoxin corresponds to amino acid residues 873 to 1293 of SEQ ID NO: 1.

In another preferred embodiment, the first neurotoxin is a BoNT/B and the second neurotoxin is a BoNT/C. Such a chimeric neurotoxin is referred to herein as a "BoNT/BC neurotoxin". More preferably, the first neurotoxin is a BoNT/B1 and the second neurotoxin is a BoNT/C1. More preferably still, the $LH_N$ domain from a first neurotoxin corresponds to amino acid residues 1 to 859 of BoNT/B1 and the $H_C$ domain from a second neurotoxin corresponds to amino acid residues 868 to 1291 of BoNT/C1. In one preferred embodiment, the $LH_N$ domain from a first neurotoxin corresponds to amino acid residues 1 to 859 of SEQ ID NO: 2 and the $H_C$ domain from a second neurotoxin corresponds to amino acid residues 868 to 1291 of SEQ ID NO:

3. In other words, a preferred chimeric neurotoxin according to the invention comprises or consists of the amino acid sequence SEQ ID NO: 56.

In another preferred embodiment, the first neurotoxin is a BoNT/C and the second neurotoxin is a BoNT/A. Such a chimeric neurotoxin is referred to herein as a "BoNT/CA neurotoxin". More preferably, the first neurotoxin is a BoNT/C1 and the second neurotoxin is a BoNT/A1. More preferably still, the $LH_N$ domain from a first neurotoxin corresponds to amino acid residues 1 to 867 of BoNT/C1 and the $H_C$ domain from a second neurotoxin corresponds to amino acid residues 873 to 1296 of BoNT/A1. In one preferred embodiment, the $LH_N$ domain from a first neurotoxin corresponds to amino acid residues 1 to 867 of SEQ ID NO: 3 and the $H_C$ domain from a second neurotoxin corresponds to amino acid residues 873 to 1296 of SEQ ID NO: 1.

The chimeric neurotoxins of the present invention can be produced using recombinant technologies. Thus, in one embodiment, a chimeric neurotoxin according to the invention is a recombinant chimeric neurotoxin. It shall be readily understood that, according to this preferred embodiment, a nucleotide sequence encoding a recombinant chimeric neurotoxin of the invention, a vector comprising said nucleotide sequence, and a cell comprising said vector, as further described below, can mutatis mutandis be referred as being recombinant.

In another aspect, the invention provides a nucleotide sequence encoding a chimeric neurotoxin according to the invention, for example a DNA or RNA sequence. In a preferred embodiment, the nucleotide sequence is a DNA sequence.

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

The DNA sequence of the present invention is preferably designed in silico, and then synthesised by conventional DNA synthesis techniques.

The above-mentioned nucleic acid sequence information is optionally modified for codon-biasing according to the ultimate host cell (e.g. *E. coli*) expression system that is to be employed.

In another aspect, the invention provides a vector comprising a nucleotide sequence according to the invention. In one embodiment, the nucleic acid sequence is prepared as part of a DNA vector comprising a promoter and terminator. In a preferred embodiment, the vector has a promoter selected from Tac, AraBAD, T7-Lac, or T5-Lac.

A vector may be suitable for in vitro and/or in vivo expression of the above-mentioned nucleic acid sequence. The vector can be a vector for transient and/or stable gene expression. The vector may additionally comprise regulatory elements and/or selection markers. Said vector may be of viral origin, of phage origin, or of bacterial origin. For example, said expression vector may be a pET, pJ401, pGEX vector or a derivative thereof.

In another aspect, the invention provides a cell comprising a nucleotide sequence or a vector according to the invention. The term "cell" can herein be used interchangeably with the term "host cell" or "cell line". Suitable cell type includes prokaryotic cells, for example *E. coli*, and eukaryotic cells, such as yeast cells, mammalian cells, insect cells, etc. Preferably, the cell is *E. coli*.

In another aspect, the invention provides a method for producing a chimeric neurotoxin according to the invention, said method comprising the step of culturing a cell as described above, under conditions wherein said chimeric neurotoxin is produced. Said conditions are well-known to the skilled practitioner and therefore need not be further detailed herein. Preferably, said method further comprises the step of recovering the chimeric neurotoxin from the culture.

In another aspect, the invention provides a pharmaceutical composition comprising a chimeric neurotoxin according to the invention. Preferably, the pharmaceutical composition comprises a chimeric neurotoxin together with at least one component selected from a pharmaceutically acceptable carrier, excipient, adjuvant, propellant and/or salt.

In another aspect, the invention provides a chimeric neurotoxin or pharmaceutical composition according to the invention for use in therapy. More precisely, the invention relates to the use of a chimeric neurotoxin or pharmaceutical composition as described herein, for manufacturing a medicament. In other words, the invention relates to a method for treating a subject in need thereof, comprising the step of administering an effective amount of a chimeric neurotoxin or pharmaceutical composition as described herein, to said subject. By "effective amount", it is meant that the chimeric neurotoxin or pharmaceutical composition is administered in a quantity sufficient to provide the effect for which it is indicated. As used herein, the term "subject" preferably refers to a human being or an animal, more preferably to a human being.

A chimeric neurotoxin according to the invention is preferably suitable for use in treating a condition associated with unwanted neuronal activity in a subject in need thereof, for example a condition selected from the group consisting of spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhidrosis, excessive salivation, excessive gastrointestinal secretions, secretory disorders, pain from muscle spasms, headache pain, migraine and dermatological conditions. More precisely, the invention relates to the use of a chimeric neurotoxin or pharmaceutical composition as described herein, for manufacturing a medicament intended to treat a condition associated with unwanted neuronal activity, as described above. In other words, the invention relates to a method for treating a condition associated with unwanted neuronal activity, as described above, in a subject in need thereof, said method comprising the step of administering an effective amount of a chimeric neurotoxin or pharmaceutical composition as described herein, to said subject.

In another aspect, the invention provides a non-therapeutic use of a chimeric neurotoxin according to the invention for treating an aesthetic or cosmetic condition, in a subject in need thereof. In other words, the invention relates to a method for treating an aesthetic or cosmetic condition in a subject in need thereof, comprising the step of administering an effective amount of a chimeric neurotoxin or pharmaceutical composition as described herein, to said subject. According to this aspect of the invention, the subject to be treated is preferably not suffering from a condition associated with unwanted neuronal activity as described above.

More preferably, said subject is a healthy subject, i.e. a subject which is not suffering from any disease.

In another aspect, the invention provides a kit for use in a therapeutic or non-therapeutic (cosmetic or aesthetic) method, or for a therapeutic or non-therapeutic (cosmetic or aesthetic) use, as described above, said kit comprising a pharmaceutical composition of the invention and instructions for performing said method or use. More precisely, the invention relates to a kit comprising a pharmaceutical composition of the invention and instructions for therapeutic or cosmetic administration of said composition to a subject in need thereof. As used herein, the term "instructions" refers to a publication, a recording, a diagram, or any other medium of expression which can be used to communicate how to perform a method or use of the invention, such as therapeutic or cosmetic administration of said composition to a subject in need thereof. Said instructions can, for example, be affixed to a container which comprises said composition or said kit.

The engineered chimeric neurotoxins of the present invention may be formulated for oral, parenteral, continuous infusion, inhalation or topical application. Compositions suitable for injection may be in the form of solutions, suspensions or emulsions, or dry powders which are dissolved or suspended in a suitable vehicle prior to use.

In the case of a chimeric neurotoxin that is to be delivered locally, the chimeric neurotoxin may be formulated as a cream (e.g. for topical application), or for sub-dermal injection.

Local delivery means may include an aerosol, or other spray (e.g. a nebuliser). In this regard, an aerosol formulation of a chimeric neurotoxin enables delivery to the lungs and/or other nasal and/or bronchial or airway passages.

Chimeric neurotoxins of the invention may be administered to a patient by intrathecal or epidural injection in the spinal column at the level of the spinal segment involved in the innervation of an affected organ.

A preferred route of administration is via laparoscopic and/or localised, particularly intramuscular, injection.

The dosage ranges for administration of the chimeric neurotoxins of the present invention are those to produce the desired therapeutic effect. It will be appreciated that the dosage range required depends on the precise nature of the chimeric neurotoxin or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Fluid dosage forms are typically prepared utilising the chimeric neurotoxin and a pyrogen-free sterile vehicle. The engineered clostridial toxin, depending on the vehicle and concentration used, can be either dissolved or suspended in the vehicle. In preparing solutions the chimeric neurotoxin can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively, the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Administration in accordance with the present invention may take advantage of a variety of delivery technologies including microparticle encapsulation, viral delivery systems or high-pressure aerosol impingement.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a clostridial neurotoxin" includes a plurality of such candidate agents and reference to "the clostridial neurotoxin" includes reference to one or more clostridial neurotoxins and equivalents thereof known to those skilled in the art, and so forth.

The invention will now be described, by way of example only, with reference to the following Figures and Examples.

DESCRIPTION OF THE DRAWINGS

FIGS. 1A-X—Sequence alignment of BoNT/A1-8, /B1-8, /C, /D, /E1-12, /F1-7, /G, /"H", and TeNT using CLUSTAL Omega (1.2.1) multiple sequence alignment tool. The location of the putative $3_{10}$ helix separating the $LH_N$ and $H_C$ domains is in bold and underlined characters.

FIGS. 2A-C—SDS PAGE of purified recombinant BoNT/AB chimera 1 (FIG. 2A), 2 (FIG. 2B) and 3A (FIG. 2C) (SEQ ID NO: 9, 10 and 11 respectively). Lanes are labelled "Marker" (molecular weight marker), "−DTT" (oxidised BoNT/AB chimera sample), and "+DTT" (reduced BoNT/AB chimera sample).

FIGS. 5A and B—SDS PAGE of purified recombinant BoNT/AB chimera 3B (FIG. 5A) and 3C (FIG. 5B) (SEQ ID NO: 12 and 13 respectively). Lanes are labelled "Marker" (molecular weight marker), "−DTT" (oxidised BoNT/AB chimera sample), and "+DTT" (reduced BoNT/AB chimera sample).

EXAMPLES

Figure 3:
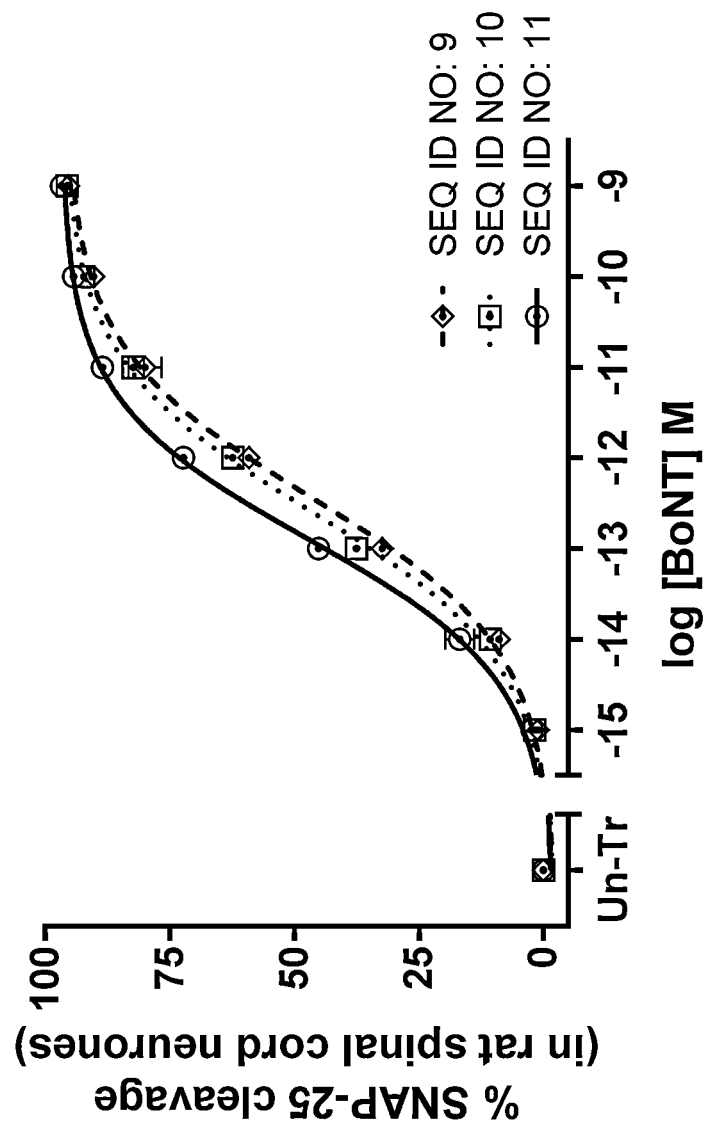
FIG. 3—Cleavage of SNAP-25 in rat spinal cord neurons by recombinant BoNT/AB chimera 1, 2 and 3A (SEQ ID NOs: 9, 10 and 11 respectively). Cultured rat primary spinal cord neurons (SCN) were exposed to various concentrations of recombinant BoNT/AB chimera 1, 2 or 3A for 24 hours, at 37° C. in a humidified atmosphere with 10% $CO_2$. Cells were then lysed with 1× NUPAGE™ buffer supplemented with DTT and BENZONASE® nuclease. The samples were transferred to microcentrifuge tubes, heated for 5 min at 90oC on heat block and stored at −20° C., before analysis of SNAP-25 cleavage by Western blot. SNAP-25 was detected using a polyclonal antibody, that detects both the full length and cleaved forms of SNAP-25 (Sigma #S9684). Anti-rabbit HRP (Sigma #A6154) was used as the secondary antibody.

The following Examples serve to illustrate particular embodiments of the invention, and do not limit the scope of the invention defined in the claims in any way.

Example 1—Mapping of $3_{10}$ Helix in Clostridial Neurotoxins

The amino acid sequences of all BoNT serotypes and TeNT were obtained from a public database (e.g., UNIPROT® or the National Center for Biotechnology Information) NCBI and then modelled onto the known crystal structure of BoNT/A1 (3BTA.pdb) using LOOPP. This yielded a predicted protein structure which was edited to retain only to N-terminal part of the HCN domain and ~80 residues before it (C-terminal part of the $H_N$ domain)—this domain ("$H_N/H_{CN}$") is structurally highly conserved, therefore, making it the best region to superimpose different serotypes. Each edited structure was then superimposed onto 3BTA.pdb using SuperPose and the residues corresponding to a conspicuous $3_{10}$ helix at the start of the He of BoNT/A1 ($^{872}$NIINTS$^{876}$) and corresponding residues in the other serotype were then identified. These were cross-checked with a sequence alignment of all BoNT serotypes with Clustal Omega (FIG. 1).

By identifying this region of structural equivalence between different neurotoxins, it was possible to identify a specific point at which a C-terminal half of one neurotoxin may transition over to a N-terminal half of another neurotoxin without interrupting the secondary structure of the overall molecule. This point was chosen to be the start of the $3_{10}$ helix.

The results are presented in table 2 above.

Example 2—Cloning, Expression and Purification of BoNT/AB Chimeras

BoNT/AB chimeric constructs 1, 2, 3A, 3B, and 3C (SEQ ID NO: 9 to 13) were constructed from DNA encoding the parent serotype molecule and appropriate oligonucleotides using standard molecular biology techniques. These were then cloned into the pJ401 expression vector with or without a C-terminal His$_{10}$-tag and transformed into BLR (DE3) E. coli cells for over-expression. These cells were grown at 37° C. and 225 RPM shaking in 2 L baffled conical flasks containing 1 L modified Terrific Broth (mTB) supplemented with the appropriate antibiotic. Once the $A_{600}$ reached >0.5, the incubator temperature was decreased to 16° C., and then induced with 1 mM IPTG an hour later for 20 h at 225 RPM shaking, to express the recombinant BoNT/AB construct.

Harvested cells were lysed by ultrasonication and clarified by centrifugation at 4500 RPM for 1 h at 4° C. The recombinant BoNT/AB chimeric molecules were then extracted in ammonium sulphate and purified by standard fast protein liquid chromatography (FPLC) techniques. This involved using a hydrophobic interaction resin for capture and an anion-exchange resin for the intermediate purification step. The partially purified molecules were then proteolytically cleaved with endoproteinase Lys-C to yield the active di-chain. This was further purified with a second hydrophobic interaction resin to obtain the final BoNT/AB chimera.

For BoNT/AB chimeric molecules with a decahistadine tag ($H_{10}$) (chimera 1, 2, 3A), the capture step employed the use of an immobilised nickel resin instead of the hydrophobic interaction resin.

The sequence of each chimera is presented in table 3.

TABLE 3 chimeric BoNT/AB constructs

| Molecule | SEQ ID NO | Sequence |
|---|---|---|
| Chimera 1 | 9 | A1:1-871 + B1:858-1291 (E1191M/S1199Y) + $His_{10}$-tag |
| Chimera 2 | 10 | A1:1-874 + ELGGGGSEL + B1:858-1291 (E1191M/S1199Y) + $His_{10}$-tag |
| Chimera 3A | 11 | A1:1-872 + B1:860-1291 (E1191M/S1199Y) + $His_{10}$-tag |
| Chimera 3B | 12 | A1:1-872 + B1:860-1291 (E1191M/S1199Y) |
| Chimera 3C | 13 | A1:1-872 + B1:860-1291 |

Example 3—Comparison of BoNT/AB Chimera 1, 2 and 3A

BoNT/AB chimera 1, 2 and 3A which have a C-terminal $His_{10}$ tag and E1191M/S1199Y double mutation were purified as described in Example 1 (FIG. 2) and tested for functional activity.

Rat Spinal Cord Neurons Snap-25 Cleavage Assay

Primary cultures of rat spinal cord neurons (SCN) were prepared and grown, for 3 weeks, in 96 well tissue culture plates (as described in: Masuyer et al., 2011, J. Struct. Biol. Structure and activity of a functional derivative of Clostridium botulinum neurotoxin B; and in: Chaddock et al., 2002, Protein Expr. Purif. Expression and purification of catalytically active, non-toxic endopeptidase derivatives of Clostridium botulinum toxin type A). Serial dilutions of BoNT/AB were prepared in SCN feeding medium. The growth medium from the wells to be treated was collected and filtered (0.2 μm filter). 125 μL of the filtered medium was added back to each test well. 125 μL of diluted toxin was then added to the plate (triplicate wells). The treated cells were incubated at 37° C., 10% $CO_2$, for 24±1 h).

Analysis of BoNT Activity Using the SNAP-25 Cleavage Assay

Following treatment, BoNT was removed and cells were washed once in PBS (Gibco, UK). Cells were lysed in 1× NUPAGE™ lysis buffer (Life Technologies) supplemented with 0.1 M dithiothreitol (DTT) and 250 units/mL BENZONASE® nuclease (Sigma). Lysate proteins were separated by SDS-PAGE and transferred to nitrocellulose membranes. Membranes were probed with a primary antibody specific for SNAP-25 (Sigma #S9684) which recognizes uncleaved SNAP-25 as well as SNAP-25 cleaved by the BoNT/A endopeptidase. The secondary antibody used was an HRP-conjugated anti-rabbit IgG (Sigma #A6154). Bands were detected by enhanced chemiluminescence and imaged using a pXi6 Access (Synoptics, UK). The intensity of bands was determined using GENETOOLS® software (Syngene, Cambridge, UK) and the percentage of SNAP-25 cleaved at each concentration of BoNT calculated. Data were fitted to a 4-parameter logistic equation and $pEC_{50}$ calculated using GRAPHPAD PRISM® version 6 (GraphPad).

Table 4 below provides the $pEC_{50}$ values determined for Chimera 1, 2 and 3A in the rat SCN SNAP-25 cleavage assay. These results show that the three BoNT/AB chimeras retained the ability to enter rat spinal cord neurons and cleave their target substrate. However, chimera 3A was more potent than chimera 1 and 2 in this assay (see also FIG. 3).

TABLE 4

| | $pEC_{50}$ ± SEM |
|---|---|
| Chimera 1 | 12.42 ± 0.04 |
| Chimera 2 | 12.57 ± 0.01 |
| Chimera 3A | 12.89 ± 0.04 |

Digit Abduction Scoring (DAS) Assay

The method to measure the activity of BoNT/AB chimera 1, 2 and 3A in the DAS assay is based on the startled response toe spreading reflex of mice, when suspended briefly by the tail. This reflex is scored as Digit Abduction Score (DAS) and is inhibited after administration of BoNT into the gastrocnemius-soleus muscles of the hind paw. Mice are suspended briefly by the tail to elicit a characteristic startled response in which the animal extends its hind limb and abducts its hind digits. (Aoki et al. 1999, Eur. J. Neurol.; 6 (suppl. 4) S3-S10)

On the day of injection, mice were anaesthetized in an induction chamber receiving isoflurane 3% in oxygen. Each mouse received an intramuscular injection of BoNT/AB chimera or vehicle (phosphate buffer containing 0.2% gelatine) in the gastrocnemius-soleus muscles of the right hind paw.

Following neurotoxin injection, the varying degrees of digit abduction were scored on a scale from zero to four, where 0=normal and 4=maximal reduction in digit abduction and leg extension. ED50 was determined by nonlinear adjustment analysis using average of maximal effect at each dose. The mathematical model used was the 4 parameters logistic model.

DAS was performed every 2 hours during the first day after dosing; thereafter it was performed 3 times a day for 4 days.

Figure 4:
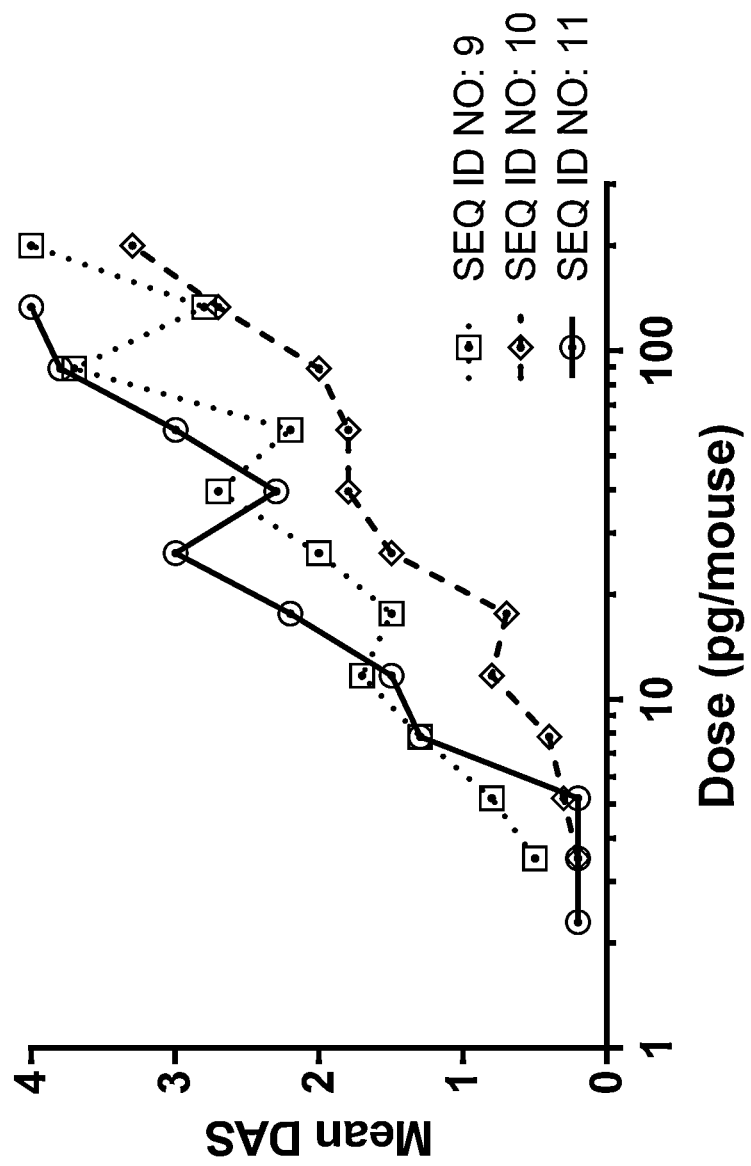
FIG. 4—Mouse digit abduction scoring assay. Mice were injected into the gastrocnemius-soleus complex muscles of one hind limb, under short general anaesthesia; muscle weakening was measured on a 0-4 scale using the digit abduction score (DAS). DAS max values were determined for each dose and plotted against dose and the data were fitted to a 4-parameter logistic equation, ED50 and dose leading to DAS 4 (DAS 4 dose) values were determined.

FIG. 4 shows the fitted curves for chimera 1, 2 and 3A (SEQ ID NO: 9, 10 and 11 respectively). The chimera 3A curve is shifted to the left, meaning lower doses of chimera 3A achieved a similar DAS response compared to chimera 1 and 2, therefore showing that chimera 3A is more potent than the others in the mouse DAS assay; see also the table below (table 5) that provides the values for the calculated ED50 and the dose leading to DAS 4 (highest score) for each chimera.

Table 5 below provides the $ED_{50}$ and DAS 4 doses determined for recombinant BoNT/A1 (rBoNT/A1) and chimeras 1, 2 and 3A in the mouse DAS assay. These results show that of the three chimeras, chimera 3A has the highest in vivo potency in inducing muscle weakening. Studies shown in FIG. 4 and table 5 were performed in mice obtained from Charles River laboratories.

TABLE 5

| | $ED_{50}$ (pg/mouse) | DAS 4 dose (pg/mouse) |
|---|---|---|
| rBoNT/A1 | 1 | 5 |
| Chimera 1 | 23 | 200 |

TABLE 5-continued

| | ED$_{50}$ (pg/mouse) | DAS 4 dose (pg/mouse) |
|---|---|---|
| Chimera 2 | 89 | >300 |
| Chimera 3A | 18 | 133 |

Example 4—Comparison of BoNT/AB Chimera 3B, 3C and BoNT/A1

Untagged BoNT/AB chimera 3B and 3C, respectively with and without the presence of the E1191M/S1199Y double mutation (SEQ ID NO: 12 and 13) were purified as described in Example 1 (FIG. 5), and tested for functional activity using recombinant BoNT/A1 (SEQ ID NO: 1) as a reference.

Human Pluripotent Stem Cells Snap-25 Cleavage Assay

Cryopreserved PERI.4U-cells were purchased from Axiogenesis (Cologne, Germany). Thawing and plating of the cells were performed as recommended by the manufacturer. Briefly, cryovials containing the cells were thawed in a water bath at 37° C. for 2 minutes. After gentle resuspension the cells were transferred to a 50 mL tube. The cryovial was washed with 1 mL of PERI.4U® thawing medium supplied by the manufacturer and the medium was transferred drop-wise to the cell suspension to the 50 mL tube, prior to adding a further 2 mL of PERI.4U® thawing medium drop-wise to the 50 mL tube. Cells were then counted using a hemocytometer. After this, a further 6 mL of PERI.4U® thawing medium was added to the cell suspension. A cell pellet was obtained by centrifugation at 260×g (e.g. 1,100 RPM) for 6 minutes at room temperature. Cells were then resuspended in complete PERI.4U® culture medium supplied by the manufacturer. Cells were plated at a density of 50,000 to 150,000 cells per cm$^2$ on cell culture plates coated with poly-L-ornithine and laminin. Cells were cultured at 37° C. in a humidified $CO_2$ atmosphere, and medium was changed completely every 2-3 days during culture.

For toxin treatment, serial dilutions of BoNTs were prepared in PERI.4U® culture medium. The medium from the wells to be treated was collected and filtered (0.2 µm filter). 125 µL of the filtered medium was added back to each test well. 125 µL of diluted toxin was then added to the plate (triplicate wells). The treated cells were incubated at 370 C, 10% $CO_2$, for 48±1 h).

Analysis of BoNT Activity Using the SNAP-25 Cleavage Assay

Following treatment, BoNT was removed and cells were washed once in PBS (Gibco, UK). Cells were lysed in 1× NUPAGE™ lysis buffer (Life Technologies) supplemented with 0.1 M dithiothreitol (DTT) and 250 units/mL BENZONASE® nuclease (Sigma). Lysate proteins were separated by SDS-PAGE and transferred to nitrocellulose membranes. Membranes were probed with a primary antibody specific for SNAP-25 (Sigma #S9684) which recognizes uncleaved SNAP-25 as well as SNAP-25 cleaved by the BoNT/A endopeptidase. The secondary antibody used was an HRP-conjugated anti-rabbit IgG (Sigma #A6154). Bands were detected by enhanced chemiluminescence and imaged using a pXi6 Access (Synoptics, UK). The intensity of bands was determined using GENETOOLS® software (Syngene, Cambridge, UK) and the percentage of SNAP-25 cleaved at each concentration of BoNT calculated. Data were fitted to a 4-parameter logistic equation and pEC$_{50}$ calculated using GRAPHPAD PRISM® version 6 (GraphPad).

Figure 6:
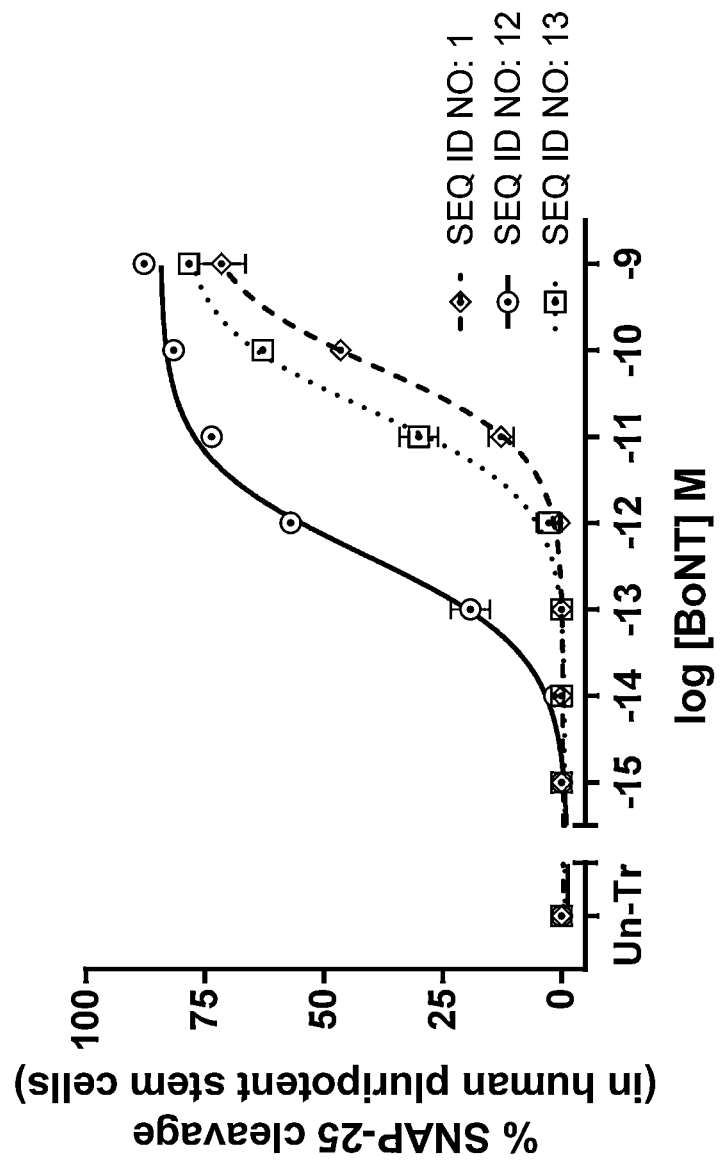
FIG. 6—Cleavage of SNAP-25 by recombinant BoNT/A and BoNT/AB chimera 3B and 3C (SEQ ID NOs: 1, 12 and 13 respectively) in human induced pluripotent stem cell derived peripheral neurons (PERI.4U—Axiogenesis, Germany). PERI.4U cells were exposed to various concentrations of recombinant BoNT/A, or BoNT/AB chimera 3B or 3C for 24 hours, at 37° C. in a humidified $CO_2$ atmosphere containing 5% $CO_2$. Cells were then lysed with 1× NUPAGE™ buffer supplemented with DTT and BENZONASE® nuclease. The samples were transferred to microcentrifuge tubes, heated for 5 min at 90° C. on heat block and stored at −20° C., before analysis of SNAP-25 cleavage by Western blot. SNAP-25 was detected using a polyclonal antibody, that detects both the full length and cleaved forms of SNAP-25 (Sigma #S9684). Anti-rabbit HRP (Sigma #A6154) was used as the secondary antibody.

FIG. 6 shows that chimera 3B and 3C displayed greater potency than rBoNT/A1 in cleaving SNAP-25 in induced human pluripotent stem cells but the former significantly more so. This can be explained by the double mutation which increases the affinity of chimera 3B for the human synaptotagmin II protein receptor present in these cells (FIG. 6, table 6).

TABLE 6

| | pEC$_{50}$ ± SEM |
|---|---|
| rBoNT/A1 | 10.21 ± 0.05 |
| Chimera 3B | 12.38 ± 0.06 |
| Chimera 3C | 10.72 ± 0.08 |

Digit Abduction Scoring (DAS) Assay—Safety Ratio

The method to measure the activity of BoNTs in the DAS assay is based on the startled response toe spreading reflex of mice, when suspended briefly by the tail. This reflex is scored as Digit Abduction Score (DAS) and is inhibited after administration of BoNT into the gastrocnemius-soleus muscles of the hind paw. Mice are suspended briefly by the tail to elicit a characteristic startled response in which the animal extends its hind limb and abducts its hind digits. (Aoki et al. 1999, Eur. J. Neurol.; 6 (suppl. 4) S3-S10)

On the day of injection, mice were anaesthetized in an induction chamber receiving isoflurane 3% in oxygen. Each mouse received an intramuscular injection of BoNT or vehicle (phosphate buffer containing 0.2% gelatine) in the gastrocnemius-soleus muscles of the right hind paw.

Following neurotoxin injection, the varying degrees of digit abduction were scored on a scale from zero to four, where 0=normal and 4=maximal reduction in digit abduction and leg extension. ED50 was determined by nonlinear adjustment analysis using average of maximal effect at each dose. The mathematical model used was the 4 parameters logistic model.

DAS was performed every 2 hours during the first day after dosing; thereafter it was performed 3 times a day for 4 days for all doses. Animals of the groups injected with vehicle and the lowest dose that induced during the first four days of injection a DAS of 4 were thereafter monitored until complete recovery of the muscle weakness to a DAS of 0 (no observed muscle weakness).

For calculation of the safety ratio all animals were weighed the day before toxin injection (DO) and thereafter once daily throughout the duration of the study. The average body weight, its standard deviation, and the standard error mean were calculated daily for each dose-group. To obtain the safety ratio for a BoNT (−10% ΔBW/ED$_{50}$), the dose at which at any time during the study the average weight of a dose-group was lower than 10% of the average weight at DO of that same dose-group was divided by the ED$_{50}$ for the BoNT studied. The lethal dose was defined as the dose at which one or more of the animals within that dose-group died.

Figure 7:
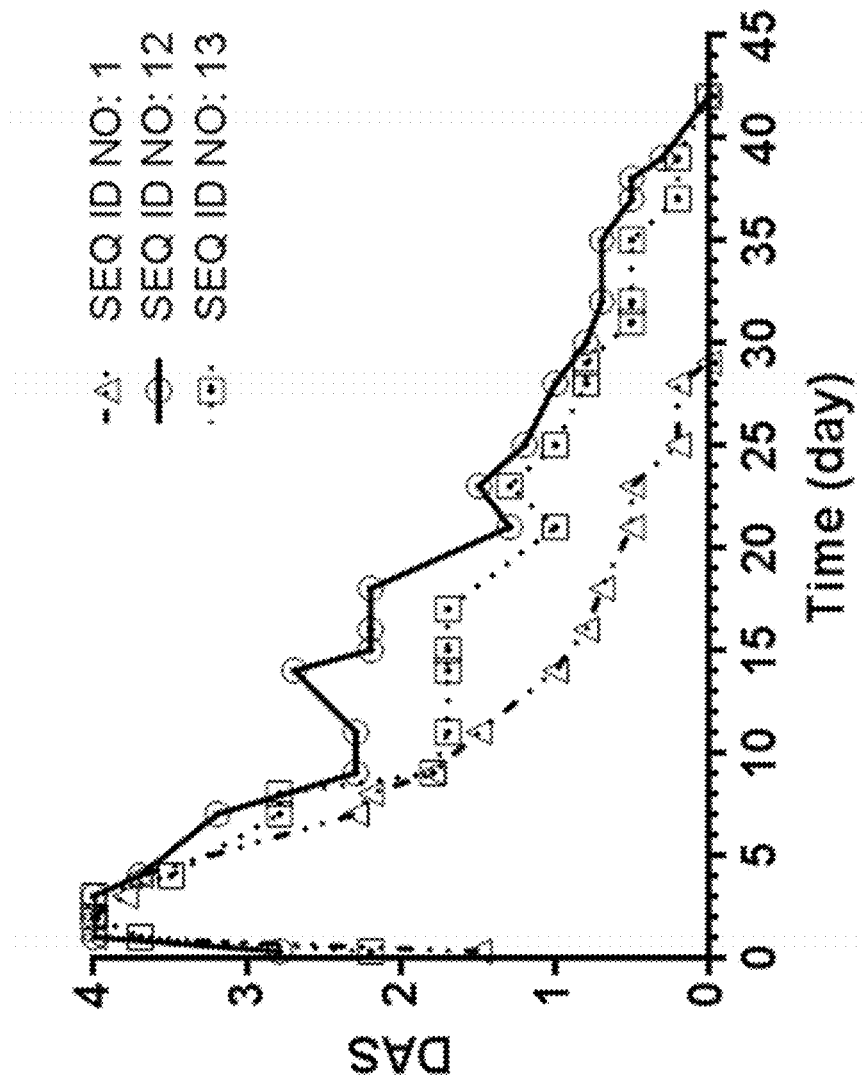
FIG. 7—Duration of muscle weakening over time in the mouse digit abduction scoring assay. Mice were injected into the gastrocnemius-soleus complex muscles of one hind limb, under short general anaesthesia; muscle weakening was measured on a 0-4 scale using the digit abduction score (DAS). Animals of the group injected with the lowest dose that induced during the first four days of injection a DAS of 4 were monitored until complete recovery of the muscle weakness to a DAS of 0 (no observed muscle weakness).

FIG. 7 shows the duration of muscle weakening over time in the mouse digit abduction scoring assay for rBoNT/A1, chimera 3B and chimera 3C (SEQ ID NO: 1, 12 and 13), showing that the chimera has longer duration of action.

Table 7 below provides the ED$_{50}$ and DAS 4 doses determined for rBoNT/A1 and chimeras 3B and 3C in the mouse DAS assay. The table also provide the total duration of action for the DAS 4 dose until complete recovery of the muscle weakness to a DAS of 0 (no observed muscle weakness). In addition, the table shows the mouse lethal dose and the safety ratio (−10% ΔBW/ED$_{50}$), as defined in the text above. In comparison to rBoNT/A1, chimeras 3B and 3C have longer duration of action, a better safety ratio, and a higher lethal dose. Studies shown in FIG. 7 and table 7 were performed in mice obtained from Janvier laboratories.

TABLE 7

| | ED$_{50}$ (DAS 2) Dose (pg/mouse) | DAS 4 dose (pg/mouse) | Total duration of action (day) with lowest DAS 4 dose | Mouse lethal dose (pg) | Safety ratio (−10% ΔBW/ED$_{50}$) |
|---|---|---|---|---|---|
| rBoNT/A1 | 0.9 | 2.3 | 29 | 18 | 4.5 |
| Chimera 3B | 8.0 | 89 | 42 | 200 | 14.1 |
| Chimera 3C | 5.0 | 26 | 42 | 8.9 | 7.4 |

Figure 8:
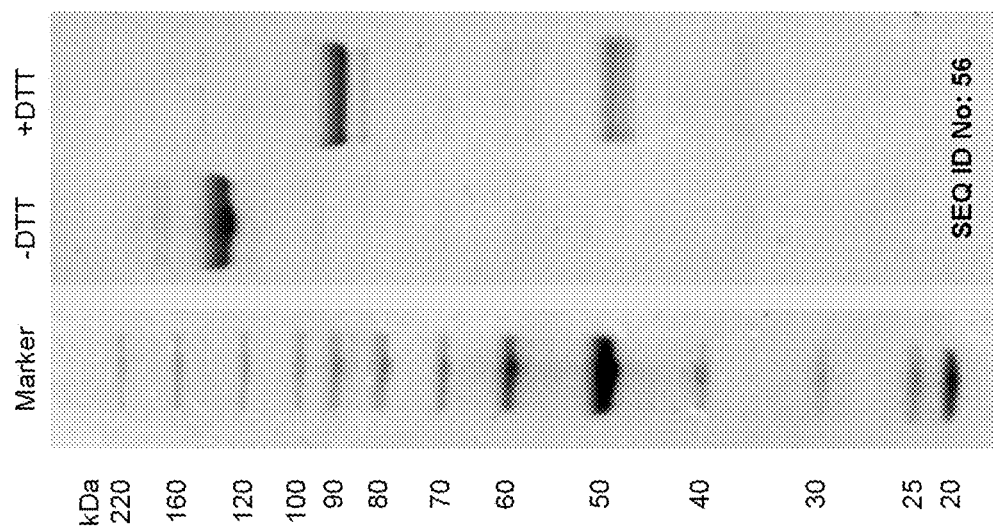
FIG. 8—SDS PAGE of purified recombinant BoNT/BC (SEQ ID NO: 56). Lanes are labelled "Marker" (molecular weight marker), "−DTT" (oxidised BoNT/BC chimera sample), and "+DTT" (reduced BoNT/BC chimera sample).

Example 5—Expression and Purification of BoNT/BC Chimera and Confirmation of Functional Activity BoNT/BC chimera 4 (SEQ ID NO: 56) was cloned, expressed and purified as described in Example 2 except for the use of a different expression cell strain (BL21) and proteolytic cleavage with trypsin rather than endoproteinase Lys-C (FIG. 8).

TABLE 8

| chimeric BoNT/BC construct | | |
|---|---|---|
| Molecule | SEQ ID NO | Sequence |
| Chimera 4 | 56 | B1:1-859 + C1:868-1291 |

This chimera was tested for functional activity in a VAMP-2 cleavage assay.

Rat Cortical Neuron Vamp-2 Cleavage Assay

Rat cortical neurons were prepared and maintained on poly-L-ornithine (PLO) coated 96-well plates at a density of 20000 cells/well in 125 μL NEUROBASAL® media containing 2% B27 supplement, 0.5 mM GLUTAMAX™ supplement, 1% foetal bovine serum (FBS) and 100 U/mL penicillin/streptomycin, at 37° C. in a humidified atmosphere containing 5% C02. A further 125 μL NEUROBASAL® medium containing 2% B27, 0.5 mM GLUTAMAX™ supplement was added on DIV 4. Cells were maintained by replacement of half the medium every 3-4 days. On DIV 11, 1.5 μM cytosine β-D-arabinofuranoside (AraC) was added to the medium to prevent proliferation of non-neuronal cells. Cortical neurons at DIV 19-21 were treated with a concentration range of BoNT (30 fM-3 nM) for 24 hours at 37° C.

Analysis of BoNT Activity Using the VAMP-2 Cleavage Assay

Cells were briefly washed in assay medium (NEUROBASAL® media w/o phenol red, 2% B27, 0.5 mM GLUTAMAX™ supplement, 10 μM TFB-TBOA ((3S)-3-[[3-[[4-(Trifluoromethyl) benzoyl] amino]phenyl] methoxy]-L-aspartic acid, before lysis in 100 μL lysis buffer (NUPAGE® LDS sample buffer, 1 mM DTT and 1:500 BENZONASE® nuclease) and heated at 90° C. for 5 minutes. 15 μL lysates were run in 12% Bis-Tris gels at 200 V for 50 minutes with MES buffer. Proteins were transferred onto nitrocellulose membranes via a TRANS-BLOT® TURBO™ transfer system (Biorad) using the low MW program Membranes were blocked with 5% low fat milk in PBST and then probed with rabbit anti-VAMP-2 (Abcam ab3347, 1:1000) primary antibody and then HRP-conjugated anti-rabbit secondary antibody (Sigma #A6154). Membranes were developed with SUPERSIGNAL® West Dura chemiluminescent substrate and visualized using a SYNGENE® PXi system. Band densitometry was analyzed using GENETOOLS® software (Syngene) and VAMP-2 percentage cleavage at each concentration of BoNT was determined relative to the control wells. Data was fit to a 4-parameter logistic equation and the pEC$_{50}$ calculated using GRAPHPAD PRISM® software (GraphPad).

Figure 9:
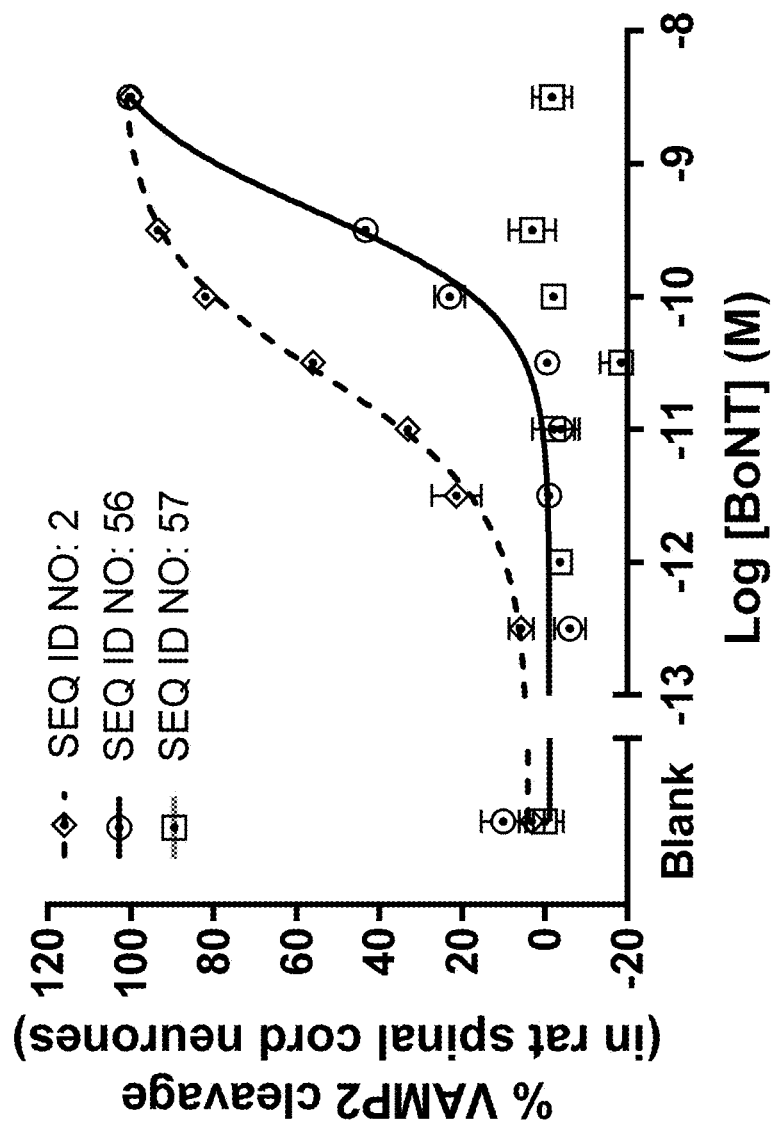
FIG. 9—Cleavage of VAMP-2 by native BoNT/B, BoNT/BC chimera, and inactive recombinant BoNT/B (SEQ ID NOs: 2, 56 and 57, respectively) in rat cortical neurons. Cells were exposed to various concentrations of BoNT for 24 hours, at 37° C. in a humidified $CO_2$ atmosphere containing 5% $CO_2$. Cells were lysed with 1× NUPAGE™ buffer supplemented with DTT and BENZONASE® nuclease, and heated for 5 min at 90° C. before storage at −20° C. Samples were analysed for VAMP-2 cleavage by Western blot using a polyclonal rabbit anti-VAMP-2 (Abcam ab3347, 1:1000) primary antibody, and an HRP-conjugated anti-rabbit secondary antibody (Sigma #A6154).

FIG. 9 shows that chimera 4 is able to bind to rat spinal cord neurones, translocate into the cytoplasm, and specifically cleave its substrate VAMP-2. As a point of reference, this chimera is clearly functional compared an inactive recombinant BoNT/B1 molecule (having a double mutation at E231Q and H234Y, and also referred herein as BoNT/B1 (0)) (SEQ ID NO: 57), and is almost as active as the native BoNT/B1 molecule (SEQ ID NO: 2) (Table 9). This may be explained by the high affinity binding of BoNT/B to synaptotagmin and various gangliosides present on the rat cell surface, whereas the binding domain of C in chimera 4, is only known to bind with lower affinity to gangliosides. This is supported by data from the light chain protease activity assay, as shown further below.

TABLE 9

| | pEC$_{50}$ ± SEM (VAMP-2 cleavage assay in rat cortical cells) |
|---|---|
| native BoNT/B1 | 10.60 ± 0.06 |
| Chimera 4 | 9.36 ± 0.15 |
| BoNT/B1(0) | inactive |

Light Chain Protease Activity Assay

The light chain activity of serotype B was assessed using the BOTEST® (BioSentinel A1009) cell-free assay according to the manufacturer's instructions. For example, BoNTs were diluted to 1.39 nM in BOTEST® Reaction Buffer (50 mM HEPES-NaOH, 5 mM NaCl, 10 μM ZnCl$_2$, 0.1% Tween-20, 0.1 mg/ml BSA, pH 7.1) and reduced with 5 mM DTT for 30 minutes at room temperature. VAMP-2 peptide reporter (CFP-VAMP-2 (33-94)-YFP in 50 mM HEPES-NaOH, 10 mM NaCl, 15% glycerol) at a final concentration of 200 nM was combined with a concentration range of BoNTs (500 fM-1.25 nM, final) in black MAXISORP® plates (Nunc) in a final assay volume of 100 μl/well. The plates were sealed and incubated at 30° C. for 18 hours away from light. The loss of CFP to YFP FRET fluorescence at 528 nm and gain of GFP fluorescence at 485 nm following excitation at 440 nm was measured using a BIOTEK® SYNGERY® HT plate reader. The fluorescence emission ratio of uncleaved:cleaved reporter substrate at each BoNT concentration was fit to a 4-parameter logistic equation and the pEC$_{50}$ calculated using GRAPHPAD PRISM® software.

Figure 10:
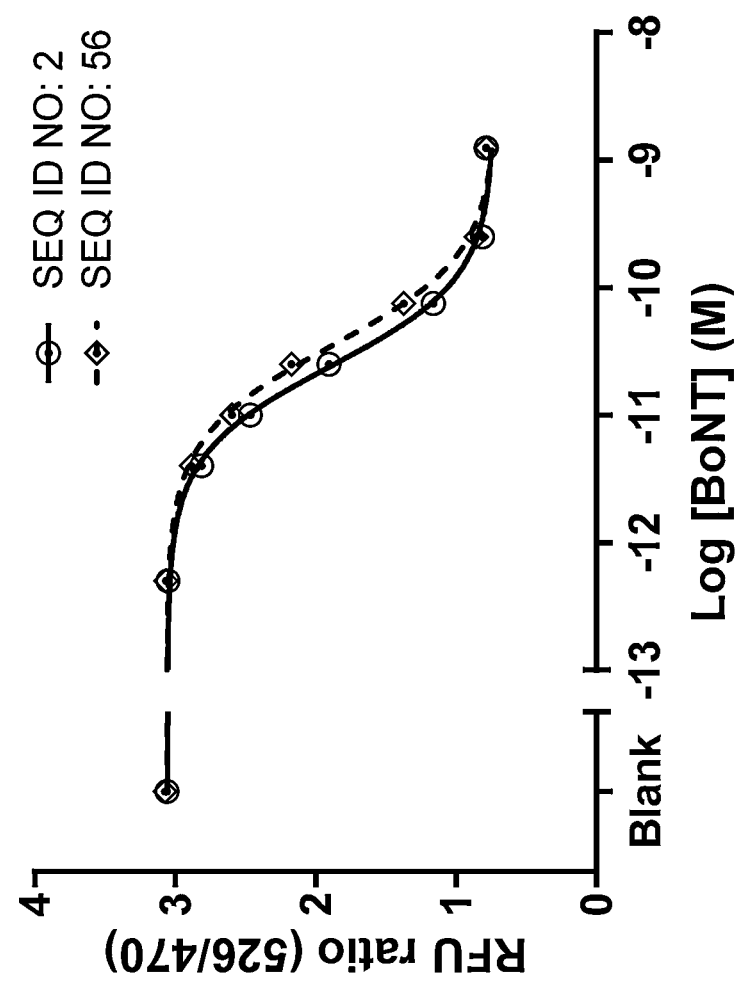
FIG. 10—Cleavage of VAMP-2 peptide reporter by native BoNT/B and BoNT/BC chimera (SEQ ID NO: 2 and 56, respectively) using the BOTEST® BoNT detection kit (BioSentinel). Various concentrations of BoNT were incubated at 30° C. for 18 hours with a VAMP-2 peptide with a CFP-YFP FRET pair as a reporter and the proportion of uncleaved: cleaved reporter substrate was measured as a loss of YFP fluorescence intensity at 528 nm and gain of CFP fluorescence at 485 nm following excitation at 440 nm.

The light chain protease activity assay confirms that the light chain of chimera 4 is as active as the one of native BoNT/B1 (see FIG. 10, and Table 10), and therefore that, as explained above, the results of the VAMP-2 cleavage assay may be explained by the fact that BoNT/B has a higher affinity to synaptotagmin and various gangliosides present on the rat cell surface, compared to the binding domain of C in chimera 4 which only binds to gangliosides.

TABLE 10

|  | pEC$_{50}$ ± SEM (VAMP-2 peptide cleavage assay in vitro) |
| --- | --- |
| native BoNT/B1 | 10.62 ± 0.01 |
| Chimera 4 | 10.46 ± 0.01 |
| BoNT/B1 (0) | NA |

The invention claimed is:

1. A nucleic acid sequence encoding a chimeric neurotoxin comprising a LH$_N$ domain from a first neurotoxin covalently linked to a H$_C$ domain from a second neurotoxin, wherein:
   the first and second neurotoxins are different;
   the C-terminal amino acid residue of said LH$_N$ domain corresponds to the first amino acid residue of the 3$_{10}$ helix separating the LH$_N$ and H$_C$ domains in said first neurotoxin; and
   the N-terminal amino acid residue of the H$_C$ domain corresponds to the second amino acid residue of the 3$_{10}$ helix separating the LH$_N$ and H$_C$ domains in the second neurotoxin.

2. A vector comprising the nucleic acid sequence of claim 1.

3. A cell comprising the nucleotide sequence of claim 1.

4. A method for producing a chimeric neurotoxin, the method comprising the step of culturing the cell of claim 3 under conditions wherein the chimeric neurotoxin is produced.

5. The nucleic acid of claim 1, wherein the first and second neurotoxins are each individually selected from botulinum neurotoxin (BoNT) serotypes A, B, C, D, E, F, or G, or Tetanus neurotoxin (TeNT).

6. The nucleic acid of claim 1, encoding a chimeric neurotoxin comprising an amino acid sequence having at least 95% sequence identity with any one of SEQ ID NO: 11-13 and 56.

7. The nucleic acid of claim 1, encoding a chimeric neurotoxin comprising an amino acid sequence having at least 95% sequence identity with SEQ ID NO: 11.

8. The nucleic acid of claim 1, encoding a chimeric neurotoxin comprising an amino acid sequence of SEQ ID NO: 11.

9. The nucleic acid of claim 1, wherein:
   the LH$_N$ domain comprises:
      amino acid residues 1 to 872 of SEQ ID NO: 1, or a sequence having at least 70% sequence identity thereto;
      amino acid residues 1 to 859 of SEQ ID NO: 2, or a sequence having at least 70% sequence identity thereto;
      amino acid residues 1 to 867 of SEQ ID NO: 3, or a sequence having at least 70% sequence identity thereto;
      amino acid residues 1 to 863 of SEQ ID NO: 4, or a sequence having at least 70% sequence identity thereto;
      amino acid residues 1 to 846 of SEQ ID NO: 5, or a sequence having at least 70% sequence identity thereto;
      amino acid residues 1 to 865 of SEQ ID NO: 6, or a sequence having at least 70% sequence identity thereto;
      amino acid residues 1 to 864 of SEQ ID NO: 7, or a sequence having at least 70% sequence identity thereto; or amino acid residues 1 to 880 of SEQ ID NO: 8, or a sequence having at least 70% sequence identity thereto; and the H$_C$ domain comprises:

amino acid residues 873 to 1296 SEQ ID NO: 1, or a sequence having at least 70% sequence identity thereto;

amino acid residues 860 to 1291 of SEQ ID NO: 2, or a sequence having at least 70% sequence identity thereto;

amino acid residues 868 to 1291 of SEQ ID NO: 3, or a sequence having at least 70% sequence identity thereto;

amino acid residues 864 to 1276 of SEQ ID NO: 4, or a sequence having at least 70% sequence identity thereto;

amino acid residues 847 to 1251 of SEQ ID NO: 5, or a sequence having at least 70% sequence identity thereto;

amino acid residues 866 to 1275 of SEQ ID NO: 6, or a sequence having at least 70% sequence identity thereto;

amino acid residues 865 to 1297 of SEQ ID NO: 7, or a sequence having at least 70% sequence identity thereto; or amino acid residues 881 to 1315 of SEQ ID NO: 8, or a sequence having at least 70% sequence identity thereto.

10. The nucleic acid of claim 1, wherein the first neurotoxin is a BoNT/A and the second neurotoxin is a BoNT/B.

11. The nucleic acid of claim 10, wherein the first neurotoxin is a BoNT/A1 and the second neurotoxin is a BoNT/B1.

12. The chimeric neurotoxin of claim 11, wherein the LH$_N$ domain comprises amino acid residues 1 to 872 of SEQ ID NO: 1, or a sequence having at least 70% sequence identity therewith, and the H$_C$ domain comprises amino acid residues 860 to 1291 of SEQ ID NO: 2, or a sequence having at least 70% sequence identity therewith.

13. The nucleic acid of claim 10, wherein the H$_C$ domain has at least one amino acid residue substitution, addition or deletion in the H$_{CC}$ subdomain that has the effect of increasing the binding affinity of the H$_C$ domain for the human Syt II receptor as compared to the natural sequence.

14. The nucleic acid of claim 13, wherein the H$_C$ domain comprises amino acid residues 860 to 1291 of SEQ ID NO: 2, or a sequence having at least 70% sequence identity therewith, and has an amino acid substitution selected from the group consisting of: V1118M; Y1183M; E1191M; E1191I; E1191Q; E1191T; S1199Y; S1199F; S1199L; S1201V; E1191C; E1191V; E1191L; E1191Y; S1199W; S1199E; S1199H; W1178Y; W1178Q; W1178A; W1178S; Y1183C; and Y1183P.

15. The nucleic acid of claim 13, wherein the H$_C$ domain comprises amino acid residues 860 to 1291 of SEQ ID NO: 2, or a sequence having at least 70% sequence identity therewith, and has the following two amino acid substitutions: E1191M and S1199L; E1191M and S1199Y; E1191M and S1199F; E1191Q and S1199L; E1191Q and S1199Y; E1191Q and S1199F; E1191M and S1199W; E1191M and W1178Q; E1191C and S1199W; E1191C and S1199Y; E1191C and W1178Q; E1191Q and S1199W; E1191V and S1199W; E1191V and S1199Y; or E1191V and W1178Q.

16. The nucleic acid of claim 15, wherein the two substitutions are E1191M and S1199Y.

17. The nucleic acid of claim 13, wherein the H$_C$ domain comprises amino acid residues 860 to 1291 of SEQ ID NO: 2, or a sequence having at least 70% sequence identity therewith, and has the following substitutions: E1191M; S1199W; and W1178Q.

18. The nucleic acid of claim 1, wherein the first neurotoxin is a BoNT/B and the second neurotoxin is a BoNT/C.

19. The nucleic acid of claim 18, wherein the first neurotoxin is a BoNT/B1 and the second neurotoxin is a BoNT/C1.

20. The nucleic acid of claim 19, wherein the LH$_N$ domain comprises amino acid residues 1 to 859 of SEQ ID NO: 2, or a sequence having at least 70% sequence identity therewith, and the H$_C$ domain comprises amino acid residues 868 to 1291 of SEQ ID NO: 3, or a sequence having at least 70% sequence identity therewith.

* * * * *

```
SEQUENCE LISTING

Sequence total quantity: 91
SEQ ID NO: 1            moltype = AA  length = 1296
FEATURE                 Location/Qualifiers
source                  1..1296
                        mol_type = protein
                        organism = Clostridium botulinum
SEQUENCE: 1
MPFVNKQFNY KDPVNGVDIA YIKIPNAGQM QPVKAFKIHN KIWVIPERDT FTNPEEGDLN    60
PPPEAKQVPV SYYDSTYLST DNEKDNYLKG VTKLFERIYS TDLGRMLLTS IVRGIPFWGG   120
STIDTELKVI DTNCINVIQP DGSYRSEELN LVIIGPSADI IQFECKSFGH EVLNLTRNGY   180
GSTQYIRFSP DFTFGFEESL EVDTNPLLGA GKFATDPAVT LAHELIHAGH RLYGIAINPN   240
RVFKVNTNAY YEMSGLEVSF EELRTFGGHD AKFIDSLQEN EFRLYYYNKF KDIASTLNKA   300
KSIVGTTASL QYMKNVFKEK YLLSEDTSGK FSVDKLKFDK LYKMLTEIYT EDNFVKFFKV   360
LNRKTYLNFD KAVFKINIVP KVNYTIYDGF NLRNTNLAAN FNGQNTEINN MNFTKLKNFT   420
GLFEFYKLLC VRGIITSKTK SLDKGYNKAL NDLCIKVNNW DLFFSPSEDN FTNDLNKGEE   480
ITSDTNIEAA EENISLDLIQ QYYLTFNFDN EPENISIENL SSDIIGQLEL MPNIERFPNG   540
KKYELDKYTM FHYLRAQEFE HGKSRIALTN SVNEALLNPS RVYTFFSSDY VKKVNKATEA   600
AMFLGWVEQL VYDFTDETSE VSTTDKIADI TIIIPYIGPA LNIGNMLYKD DFVGALIFSG   660
AVILLEFIPE IAIPVLGTFA LVSYIANKVL TVQTIDNALS KRNEKWDEVY KYIVTNWLAK   720
VNTQIDLIRK KMKEALENQA EATKAIINYQ YNQYTEEEKN NINFNIDDLS SKLNESINKA   780
MININKFLNQ CSVSYLMNSM IPYGVKRLED FDASLKDALL KYIYDNRGTL IGQVDRLKDK   840
VNNTLSTDIP FQLSKYVDNQ RLLSTFTEYI KNIINTSILN LRYESNHLID LSRYASKINI   900
GSKVNFDPID KNQIQLFNLE SSKIEVILKN AIVYNSMYEN FSTSFWIRIP KYFNSISLNN   960
EYTIINCMEN NSGWKVSLNY GEIIWTLQDT QEIKQRVVFK YSQMINISDY INRWIFVTIT  1020
NNRLNNSKIY INGRLIDQKP ISNLGNIHAS NNIMFKLDGC RDTHRYIWIK YFNLFDKELN  1080
EKEIKDLYDN QSNSGILKDF WGDYLQYDKP YYMLNLYDPN KYVDVNNVGI RGYMYLKGPR  1140
GSVMTTNIYL NSSLYRGTKF IIKKYASGNK DNIVRNNDRV YINVVVKNKE YRLATNASQA  1200
GVEKILSALE IPDVGNLSQV VVMKSKNDQG ITNKCKMNLQ DNNGNDIGFI GFHQFNNIAK  1260
LVASNWYNRQ IERSSRTLGC SWEFIPVDDG WGERPL                           1296

SEQ ID NO: 2            moltype = AA  length = 1291
FEATURE                 Location/Qualifiers
source                  1..1291
                        mol_type = protein
                        organism = Clostridium botulinum
SEQUENCE: 2
MPVTINNFNY NDPIDNNNII MMEPPFARGT GRYYKAFKIT DRIWIIPERY TFGYKPEDFN    60
KSSGIFNRDV CEYYDPDYLN TNDKKNIFLQ TMIKLFNRIK SKPLGEKLLE MIINGIPYLG   120
DRRVPLEEFN TNIASVTVNK LISNPGEVER KKGIFANLII FGPGPVLNEN ETIDIGIQNH   180
FASREGFGGI MQMKFCPEYV SVFNNVQENK GASIFNRRGY FSDPALILMH ELIHVLHGLY   240
GIKVDDLPIV PNEKKFFMQS TDAIQAEELY TFGGQDPSII TPSTDKSIYD KVLQNFRGIV   300
DRLNKVLVCI SDPNINNIY KNKFKDKYKF VEDSEGKYSI DVESFDKLYK SLMFGFTETN   360
IAENYKIKTR ASYFSDSLPP VKIKNLLDNE IYTIEEGFNI SDKDMEKEYR GQNKAINKQA   420
YEEISKEHLA VYKIQMCKSV KAPGICIDVD NEDLFFIADK NSFSDDLSKN ERIEYNTQSN   480
YIENDFPINE LILDTDLISK IELPSENTES LTDFNVDVPV YEKQPAIKKI FTDENTIFQY   540
LYSQTFPLDI RDISLTSSFD DALLFSNKVY SFFSMDYIKT ANKVVEAGLF AGWVKQIVND   600
FVIEANKSNT MDKIADISLI VPYIGLALNV GNETAKGNFE NAFEIAGASI LLEFIPELLI   660
PVVGAFLLES YIDNKNKIIK TIDNALTKRN EKWSDMYGLI VAQWLSTVNT QFYTIKEGMY   720
KALNYQAQAL EEIIKYRYNI YSEKEKSNIN IDFNDINSKL NEGINQAIDN INNFINGCSV   780
SYLMKKMIPL AVEKLLDFDN TLKKNLLNYI DENKLYLIGS AEYEKSKVNK YLKTIMPFDL   840
SIYTNDTILI EMFNKYNSEI LNNIILNLRY KDNNLIDLSG YGAKVEVYDG VELNDKNQFK   900
LTSSANSKIR VTQNQNIIFN SVFLDFSVSF WIRIPKYKND GIQNYIHNEY TIINCMKNNS   960
GWKISIRGNR IIWTLIDING KTKSVFFEYN IREDISEYIN RWFFVTITNN LNNAKIYING  1020
KLESNTDIKD IREVIANGEI IFKLDGDIDR TQFIWMKYFS IFNTELSQSN IEERYKIQSY  1080
SEYLKDFWGN PLMYNKEYYM FNAGNKNSYI KLKKDSPVGE ILTRSKYNQN SKYINYRDLY  1140
IGEKFIIRRK SNSQSINDDI VRKEDYIYLD FFNLNQEWRV YTYKYFKKEE EKLFLAPISD  1200
SDEFYNTIQI KEYDEQPTYS CQLLFKKDEE STDEIGLIGI HRFYESGIVF EEYKDYFCIS  1260
KWYLKEVKRK PYNLKLGCNW QFIPKDEGWT E                                 1291

SEQ ID NO: 3            moltype = AA  length = 1291
FEATURE                 Location/Qualifiers
source                  1..1291
                        mol_type = protein
                        organism = Clostridium botulinum
```

```
SEQUENCE: 3
MPITINNFNY SDPVDNKNIL YLDTHLNTLA NEPEKAFRIT GNIWVIPDRF SRNSNPNLNK    60
PPRVTSPKSG YYDPNYLSTD SDKDPFLKEI IKLFKRINSR EIGEELIYRL STDIPFPGNN   120
NTPINTFDFD VDFNSVDVKT RQGNNWVKTG SINPSVIITG PRENIIDPET STFKLTNNTF   180
AAQEGFGALS IISISPRFML TYSNATNDVG EGRFSKSEFC MDPILILMHE LNHAMHNLYG   240
IAIPNDQTIS SVTSNIFYSQ YNVKLEYAEI YAFGGPTIDL IPKSARKYFE EKALDYYRSI   300
AKRLNSITTA NPSSFNKYIG EYKQKLIRKY RFVVESSGEV TVNRNKFVEL YNELTQIFTE   360
FNYAKIYNVQ NRKIYLSNVY TPVTANILDD NVYDIQNGFN IPKSNLNVLF MGQNLSRNPA   420
LRKVNPENML YLFTKFCHKA IDGRSLYNKT LDCRELLVKN TDLPFIGDIS DVKTDIFLRK   480
DINEETEVIY YPDNVSVDQV ILSKNTSEHG QLDLLYPSID SESEILPGEN QVFYDNRTQN   540
VDYLNSYYYL ESQKLSDNVE DFTFTRSIEE ALDNSAKVYT YFPPTLANKVN AGVQGGLFLM   600
WANDVVEDFT TNILRKDTLD KISDVSAIIP YIGPALNISN SVRRGNFTEA FAVTGVTILL   660
EAFPEFTIPA LGAFVIYSKV QERNEIIKTI DNCLEQRIKR WKDSYEWMMG TWLSRIITQF   720
NNISYQMYDS LNYQAGAIKA KIDLEYKKYS GSDKENIKSQ VENLKNSLDV KISEAMNNIN   780
KFIRECSVTY LFKNMLPKVI DELNEFDRNT KAKLINLIDS HNIILVGEVD KLKAKVNNSF   840
QNTIPFNIFS YTNNSLLKDI INEYFNNIND SKILSLQNRK NTLVDTSGYN AEVSEEGDVQ   900
LNPIFPFDFK LGSSGEDRGK VIVTQNENIV YNSMYESFSI SFWIRINKWV SNLPGYTIID   960
SVKNNSGWSI GIISNFLVFT LKQNEDSEQS INFSYDISNN APGYNKWFFV TVTNNMMGNM  1020
KIYINGKLID TIKVKELTGI NFSKTITFEI NKIPDTGLIT SDSDNINMWI RDFYIFAKEL  1080
DGKDINILFN SLQYTNVVKD YWGNDLRYNK EYYMVNIDYL NRYMYANSRQ IVFNTRRNNN  1140
DFNEGYKIII KRIRGNTNDT RVRGGDILYF DMTINNKAYN LFMKNETMYA DNHSTEDIYA  1200
IGLREQTKDI NDNIIFQIQP MNNTYYYASQ IFKSNFNGEN ISGICSIGTY RFRLGGDWYR  1260
HNYLVPTVKQ GNYASLLEST STHWGFVPVS E                                1291

SEQ ID NO: 4           moltype = AA  length = 1276
FEATURE                Location/Qualifiers
source                 1..1276
                       mol_type = protein
                       organism = Clostridium botulinum
SEQUENCE: 4
MTWPVKDFNY SDPVNDNDIL YLRIPQNKLI TTPVKAFMIT QNIWVIPERF SSDTNPSLSK    60
PPRPTSKYQS YYDPSYLSTD EQKDTFLKGI IKLFKRINER DIGKKLINYL VVGSPFMGDS   120
STPEDTFDFT RHTTNIAVEK FENGSWKVTN IITPSVLIFG PLPNILDYTA SLTLQGQQSN   180
PSFEGFGTLS ILKVAPEFLL TFSDVTSNQS SAVLGKSIFC MDPVIALMHE LTHSLHQLYG   240
INIPSDKRIR PQVSEGFFSQ DGPNVQFEEL YTFGGLDVEI IPQIERSQLR EKALGHYKDI   300
AKRLNNINKT IPSSWISNID KYKKIFSEKY NFDKDNTGNF VVNIDKFNSL YSDLTNVMSE   360
VVYSSQYNVK NRTHYFSRHY LPVFANILDD NIYTIRDGFN LTNKGFNIEN SGQNIERNPA   420
LQKLSSESVV DLFTKVCLRL TKNSRDDSTC IKVKNNRLPY VADKDSISQE IFENKIITDE   480
TNVQNYSDKF SLDESILDGQ VPINPEIVDP LLPNVNMEPL NLPGEEIVFY DDITKYVDYL   540
NSYYYLESQK LSNNVENITL TTSVEEALGY SNKIYTFLPS LAEKVNKGVQ AGLFLNWANE   600
VVEDFTTNIM KKDTLDKISD VSVIIPYIGP ALNIGNSALR GNFNQAFATA GVAFLLEGFP   660
EFTIPALGVF TFYSSIQERE KIIKTIENCL EQRVRKWKDS YQWMVSNWLS RITTQFNHIN   720
YQMYDSLSYQ ADAIKAKIDL EYKKYSGSDK ENIKSQVENL KNSLDVKISE AMNNINKFIR   780
ECSVTYLFKN MLPKVIDELN KFDLRTKTEL INLIDSHNII LVGEVDRLKA KVNESFENTM   840
PFNIFSYTNN SLLKDIINEY FNSINDSKIL SLQNKKNALV DTSGYNAEVR VGDNVQLNTI   900
YTNDFKLSSS GDKIIVNLNN NILYSAIYEN SSVSFWIKIS KDLTNSHNEY TIINSIEQNS   960
GWKLCIRNGN IEWILQDVNR KYKSLIFDYS ESLSHTGYTN KWFFVTITNN IMGYMKLYIN  1020
GELKQSQKIE DLDEVKLDKT IVFGIDENID ENQMLWIRDF NIFSKELSNE DINIVYEGQI  1080
LRNVIKDYWG NPLKFDTEYY IINDNYIDRY IAPESNVLVL VQYPDRSKLY TGNPITIKSV  1140
SDKNPYSRIL NGDNIILHML YNSRKYMIIR DTDTIYATQG GECSQNCVYA LKLQSNLGNY  1200
GIGIFSIKNI VSKNKYCSQI FSSFRENTML LADIYKPWRF SFKNAYTPVA VTNYETKLLS  1260
TSSFWKFISR DPGWVE                                                 1276

SEQ ID NO: 5           moltype = AA  length = 1252
FEATURE                Location/Qualifiers
source                 1..1252
                       mol_type = protein
                       organism = Clostridium botulinum
SEQUENCE: 5
MPKINSFNYN DPVNDRTILY IKPGGCQEFY KSFNIMKNIW IIPERNVIGT TPQDFHPPTS    60
LKNGDSSYYD PNYLQSDEEK DRFLKIVTKI FNRINNNLSG GILLEELSKA NPYLGNDNTP   120
DNQFHIGDAS AVEIKFSNGS QDILLPNVII MGAEPDLFET NSSNISLRNN YMPSNHGFGS   180
IAIVTFSPEY SFRFNDNSMN EFIQDPALTL MHELIHSLHG LYGAKGITTK YTITQKQNPL   240
ITNIRGTNIE EFLTFGGTDL NIITSAQSND IYTNLLADYK KIASKLSKVQ VSNPLLNPYK   300
DVFEAKYGLD KDASGIYSVN INKFNDIFKK LYSFTEFDLA TKFQVKCRQT YIGQYKYFKL   360
SNLLNDSIYN ISEGYNINNL KVNFRGQNAN LNPRIITPIT GRGLVKKIIR FCKNIVSVKG   420
IRKSICIEIN NGELFFVASE NSYNDDNINT PKEIDDTVTS NNNYENDLDQ VILNFNSESA   480
PGLSDEKLNL TIQNDAYIPK YDSNGTSDIE QHDVNELNVF FYLDAQKVPE GENNVNLTSS   540
IDTALLEQPK IYTFFSSEFI NNVNKPVQAA LFVSWIQQVL VDFTTEANQK STVDKIADIS   600
IVVPYIGLAL NIGNEAQKGN FKDALELLGA GILLEFEPEL LIPTILVFTI KSFLGSSDNK   660
NKVIKAINNA LKERDEKWKE VYSFIVSNWM TKINTQFNKR KEQMYQALQN QVNAIKTIIE   720
SKYNSYTLEE KNELTNKYDI KQIENELNQK VSIAMNNIDR FLTESSISYL MKLINEVKIN   780
KLREYDENVK TYLLNYIIQH GSILGESQQE LNSMVTDTLN NSIPFKLSSY TDDKILISYF   840
NKFFKRIKSS SVLNMRYKND YKVDTSGYDS NININGDVYK YPTNKNQFGI YNDKLSEVNI   900
SQNDYIIYDN KYKNFSISFW VRIPNYDNKI VNVNNEYTII NCMRDNNSGW KVSLNHNEII   960
WTLQDNAGIN QKLAFNYGNA NGISDYINKW IFVTITNDRL GDSKLYINGN LIDQKSILNL  1020
GNIHVSDNIL FKIVNCSYTR YIGIRYFNIF DKELDETEIQ TLYSNEPNTN ILKDFWGNYL  1080
LYDKEYYLLN VLKPNNFIDR RKDSTLSINN IRSTILLANR LYSGIKVKIQ RVNNSSTNDN  1140
LVRKNDQVYI NFVASKTHLF PLYADTATTN KEKTIKISSS GNRFNQVVVM NSVGNNCTMN  1200
```

```
FKNNNGNNIG LLGFKADTVV ASTWYYTHMR DHTNSNGCFW NFISEEHGWQ EK        1252

SEQ ID NO: 6            moltype = AA   length = 1278
FEATURE                 Location/Qualifiers
source                  1..1278
                        mol_type = protein
                        organism = Clostridium botulinum
SEQUENCE: 6
MPVVINSFNY NDPVNDDTIL YMQIPYEEKS KKYYKAFEIM RNVWIIPERN TIGTDPSDFD  60
PPASLENGSS AYYDPNYLTT DAEKDRYLKT TIKLFKRINS NPAGEVLLQE ISYAKPYLGN 120
EHTPINEFHP VTRTTSVNIK SSTNVKSSII LNLLVLGAGP DIFENSSYPV RKLMDSGGVY 180
DPSNDGFGSI NIVTFSPEYE YTFNDISGGY NSSTESFIAD PAISLAHELI HALHGLYGAR 240
GVTYKETIKV KQAPLMIAEK PIRLEEFLTF GGQDLNIITS AMKEKIYNNL LANYEKIATR 300
LSRVNSAPPE YDINEYKDYF QWKYGLDKNA DGSYTVNENK FNEIYKKLYS FTEIDLANKF 360
KVKCRNTYFI KYGFLKVPNL LDDDIYTVSE GFNIGNLAVN NRGQNIKLNP KIIDSIPDKG 420
LVEKIVKFCK SVIPRKGTKA PPRLCIRVNN RELFFVASES SYNENDINTP KEIDDTTNLN 480
NNYRNNLDEV ILDYNSETIP QISNQTLNTL VQDDSYVPRY DSNGTSEIEE HNVVDLNVFF 540
YLHAQKVPEG ETNISLTSSI DTALSEESQV YTFFSSEFIN TINKPVHAAL FISWINQVIR 600
DFTTEATQKS TFDKIADISL VVPYVGLALN IGNEVQKENF KEAFELLGAG ILLEFVPELL 660
IPTILVFTIK SFIGSSENKN KIIKAINNSL MERETKWKEI YSWIVSNWLT RINTQFNKRK 720
EQMYQALQNQ VDAIKTVIEY KYNNYTSDER NRLESEYNIN NIREELNKKV SLAMENIERF 780
ITESSIFYLM KLINEAKVSK LREYDEGVKE YLLDYISEHR SILGNSVQEL NDLVTSTLNN 840
SIPFELSSYT NDKILILYFN KLYKKIKDNS ILDMRYENNK FIDISGYGSN ISINGDVYIY 900
STNRNQFGIY SSKPSEVNIA QNNDIIYNGR YQNFSISFWV RIPKYFNKVN LNNEYTIIDC 960
IRNNNSGWKI SLNYNKIIWT LQDTAGNNQK LVFNYTQMIS ISDYINKWIF VTITNNRLGN 1020
SRIYINGNLI DEKSISNLGD IHVSDNILFK IVGCNDTRYV GIRYFKVFDT ELGKTEIETL 1080
YSDEPDPSIL KDFWGNYLLY NKRYYLLNLL RTDKSITQNS NFLNINQQRG VYQKPNIFSN 1140
TRLYTGVEVI IRKNGSTDIS NTDNFVRKND LAYINVVDRD VEYRLYADIS IAKPEKIIKL 1200
IRTSNSNNLS GQIIVMDSIG NNCTMNFQNN NGGNIGLLGF HSNNLVASSW YYNNIRKNTS 1260
SNGCFWSFIS KEHGWQEN                                              1278

SEQ ID NO: 7            moltype = AA   length = 1297
FEATURE                 Location/Qualifiers
source                  1..1297
                        mol_type = protein
                        organism = Clostridium botulinum
SEQUENCE: 7
MPVNIKNFNY NDPINNDDII MMEPFNDPGP GTYYKAFRII DRIWIVPERF TYGFQPDQFN  60
ASTGVFSKDV YEYYDPTYLK TDAEKDKFLK TMIKLFNRIN SKPSGQRLLD MIVDAIPYLG 120
NASTPPDKFA ANVANVSINK KIIQPGAEDQ IKGLMTNLII FGPGPVLSDN FTDSMIMNGH 180
SPISEGFGAR MMIRFCPSCL NVFNNVQENK DTSIFSRRAY FADPALTLMH ELIHVLHGLY 240
GIKISNLPIT PNTKEFFMQH SDPVQAEELY TFGGHDPSVI SPSTDMNIYN KALQNFQDIA 300
NRLNIVSSAQ GSGIDISLYK QIYKNKYDFV EDPNGKYSVD KDKFDKLYKA LMFGFTETNL 360
AGEYGIKTRY SYFSEYLPPI KTEKLLDNTI YTQNEGFNIA SKNLKTEFNG QNKAVNKEAY 420
EEISLEHLVI YRIAMCKPVM YKNTGKSEQC IIVNNEDLFF IANKDSFSKD LAKAETIAYN 480
TQNNTIENNF SIDQLILDND LSSGIDLPNE NTEPFTNFDD IDIPVYIKQS ALKKIFVDGD 540
SLFEYLHAQT FPSNIENLQL TNSLNDALRN NNKVYTFEST NNKATVV GASLFVNWVK 600
GVIDDFTSES TQKSTIDKVS DVSIIIPYIG PALNVGNETA KENFKNAFEI GGAAILMEFI 660
PELIVPIVGF FTLESYVGNK GHIIMTISNA LKKRDQKWTD MYGLIVSQWL STVNTQFYTI 720
KERMYNALNN QSQAIEKIIE DQYNRYSEED KMNINIDFND IDFKLNQSIN LAINNIDDFI 780
NQCSISYLMN RMIPLAVKKL KDFDDNLKRD LLEYIDTNEL IVKLDEVNILK SKVNRHLKDS 840
IPFDLSLYTK DTILIQVFNN YISNISSNAI LSLSYRGGRL IDSSGYGATM NVGSDVIFND 900
IGNGQFKLNN SENSNITAHQ SKFVVYDSMF DNFSINFWVR TPKYNNNDIQ TYLQNEYTII 960
SCIKNDSGWK VSIKGNRIIW TLIDVNAKSK SIFFEYSIKD NISDYINKWF SITITNDRLG 1020
NANIYINGSL KKSEKILNLD RINSSNDIDF KLINCTDTTK FVWIKDFNIF GRELNATEVS 1080
SLYWIQSSTN TLKDFWGNPL RYDTQYYLFN QGMQNIYIKY FSKASMGETA PRTNFNNAAI 1140
NYQNLYLGLR FIIKKASNSR NINNDNIVRE GDYIYLNIDN ISDESYRVYV LVNSKEIQTQ 1200
LFLAPINDDP TFYDVLQIKK YYEKTTYNCQ ILCEKDTKTF GLFGIGKFVK DYGYVWDTYD 1260
NYFCISQWYL RRISENINKL RLGCNWQFIP VDEGWTE                         1297

SEQ ID NO: 8            moltype = AA   length = 1315
FEATURE                 Location/Qualifiers
source                  1..1315
                        mol_type = protein
                        organism = Clostridium tetani
SEQUENCE: 8
MPITINNFRY SDPVNNDTII MMEPPYCKGL DIYYKAFKIT DRIWIVPERY EFGTKPEDFN  60
PPSSLIEGAS EYYDPNYLRT DSDKDRFLQT MVKLFNRIKN NVAGEALLDK IINAIPYLGN 120
SYSLLDKFDT NSNSVSFNLL EQDPSGATTK SAMLTNLIIF GPGPVLNKNE VRGIVLRVDN 180
KNYFPCRDGF GSIMQMAFCP EYVPTFDNVI ENITSLTIGK SKYFQDPALL LMHELIHVLH 240
GLYGMQVSSH EIIPSKQEIY MQHTYPISAE ELFTFGGQDA NLISIDIKND LYEKTLNDYK 300
AIANKLSQVT SCNDPNIDID SYKQIYQQKY QFDKDSNGQY IVNEDKFQIL YNSIMYGFTE 360
IELGKKFNIK TRLSYFSMNH DPVKIPNLLD DTIYNDTEGF NIESKDLKSE YKGQNMRVNT 420
NAFRNVDGSG LVSKLIGLCK KIIPPTNIRE NLYNRTASLT DLGGELCIKI KNEDLTFIAE 480
KNSFSEEPFQ DEIVSYNTKN KPLNFNYSLD KIIVDYNLQS KITLPNDRTT PVTKGIPYAP 540
EYKSNAASTI EIHNIDDNTI YQYLYAQKSP TTLQRITMTN SVDDALINST KIYSYFPSVI 600
SKVNQGAQGI LFLQWVRDII DDFTNESSQK TTIDKISDVS TIVPYIGPAL NIVKQGYEGN 660
FIGALETTGV VLLLEYIPEI TLPVIAALSI AESSTQKEKI IKTIDNFLEK RYEKWIEVYK 720
LVKAKWLGTV NTQFQKRSYQ MYRSLEYQVD AIKKIIDYEY KIYSGPDKEQ IADEINNLKN 780
```

```
KLEEKANKAM ININIFMRES SRSFLVNQMI NEAKKQLLEF DTQSKNILMQ YIKANSKFIG  840
ITELKKLESK INKVFSTPIP FSYSKNLDCW VDNEEDIDVI LKKSTILNLD INNDIISDIS  900
GFNSSVITYP DAQLVPGING KAIHLVNNES SEVIVHKAMD IEYNDMFNNF TVSFWLRVPK  960
VSASHLEQYG TNEYSIISSM KKHSLSIGSG WSVSLKGNNL IWTLKDSAGE VRQITFRDLP  1020
DKFNAYLANK WVFITITNDR LSSANLYING VLMGSAEITG LGAIREDNNI TLKLDRCNNN  1080
NQYVSIDKFR IFCKALNPKE IEKLYTSYLS ITFLRDFWGN PLRYDTEYYL IPVASSSKDV  1140
QLKNITDYMY LTNAPSYTNG KLNIYYRRLY NGLKFIIKRY TPNNEIDSFV KSGDFIKLYV  1200
SYNNNEHIVG YPKDGNAFNN LDRILRVGYN APGIPLYKKM EAVKLRDLKT YSVQLKLYDD  1260
KNASLGLVGT HNGQIGNDPN RDILIASNWY FNHLKDKILG CDWYFVPTDE GWTND       1315

SEQ ID NO: 9              moltype = AA   length = 1315
FEATURE                   Location/Qualifiers
REGION                    1..1315
                          note = BoNT/AB
source                    1..1315
                          mol_type = protein
                          organism = synthetic construct
SEQUENCE: 9
MPFVNKQFNY KDPVNGVDIA YIKIPNAGQM QPVKAFKIHN KIWVIPERDT FTNPEEGDLN  60
PPPEAKQVPV SYYDSTYLST DNEKDNYLKG VTKLFERIYS TDLGRMLLTS IVRGIPFWGG  120
STIDTELKVI DTNCINVIQP DGSYRSEELN LVIIGPSADI IQFECKSFGH EVLNLTRNGY  180
GSTQYIRFSP DFTFGFEESL EVDTNPLLGA GKFATDPAVT LAHELIHAGH RLYGIAINPN  240
RVFKVNTNAY YEMSGLEVSF EELRTFGGHD AKFIDSLQEN EFRLYYYNKF KDIASTLNKA  300
KSIVGTTASL QYMKNVFKEK YLLSEDTSGK FSVDKLKFDK LYKMLTEIYT EDNFVKFFKV  360
LNRKTYLNFD KAVFKINIVP KVNYTIYDGF NLRNTNLAAN FNGQNTEINN MNFTKLKNFT  420
GLFEFYKLLC VRGIITSKTK SLDKGYNKAL NDLCIKVNNW DLFFSPSEDN FTNDLNKGEE  480
ITSDTNIEAA EENISLDLIQ QYYLTFNFDN EPENISIENL SSDIIGQLEL MPNIERFPNG  540
KKYELDKYTM PHYLRAQEFE HGKSRIALTN SVNEALLNPS RVYTFFSSDY VKKVNKATEA  600
AMFLGWVEQL VYDFTDETSE VSTTDKIADI TIIIPYIGPA LNIGNMLYKD DFVGALIFSG  660
AVILLEFIPE IAIPVLGTFA LVSYIANKVL TVQTIDNALS KRNEKWDEVY KYIVTNWLAK  720
VNTQIDLIRK KMKEALENQA EATKAIINYQ YNQYTEEEKN NINFNIDDLS SKLNESINKA  780
MININKFLNQ CSVSYLMNSM IPYGVKRLED FDASLKDALL KYIYDNRGTL IGQVDRLKDK  840
VNNTLSTDIP FQLSKYVDNQ RLLSTFTEYI KSEILNNIIL NLRYKDNNLI DLSGYGAKVE  900
VYDGVELNDK NQFKLTSSAN SKIRVTQNQN IIFNSVFLDF SVSFWIRIPK YKNDGIQNYI  960
HNEYTIINCM KNNSGWKISI RGNRIIWTLI DINGKTKSVF FEYNIREDIS EYINRWFFVT  1020
ITNNLNNAKI YINGKLESNT DIKDIREVIA NGEIIFKLDG DIDRTQFIWM KYFSIFNTEL  1080
SQSNIEERYK IQSYSEYLKD FWGNPLMYNK EYYMFNAGNK NSYIKLKKDS PVGEILTRSK  1140
YNQNSKYINY RDLYIGEKFI IRRKSNSQSI NDDIVRKEDY YILDFFNLNQ EWRVYTYKYF  1200
KKEEMKLFLA PIYDSDEFYN TIQIKEYDEQ PTYSCQLLFK KDEESTDEIG LIGIHRFYES  1260
GIVFEEYKDY FCISKWYLKE VKRKPYNLKL GCNWQFIPKD EGWTEHHHHH HHHHH       1315

SEQ ID NO: 10             moltype = AA   length = 1327
FEATURE                   Location/Qualifiers
REGION                    1..1327
                          note = BoNT/AB
source                    1..1327
                          mol_type = protein
                          organism = synthetic construct
SEQUENCE: 10
MPFVNKQFNY KDPVNGVDIA YIKIPNAGQM QPVKAFKIHN KIWVIPERDT FTNPEEGDLN  60
PPPEAKQVPV SYYDSTYLST DNEKDNYLKG VTKLFERIYS TDLGRMLLTS IVRGIPFWGG  120
STIDTELKVI DTNCINVIQP DGSYRSEELN LVIIGPSADI IQFECKSFGH EVLNLTRNGY  180
GSTQYIRFSP DFTFGFEESL EVDTNPLLGA GKFATDPAVT LAHELIHAGH RLYGIAINPN  240
RVFKVNTNAY YEMSGLEVSF EELRTFGGHD AKFIDSLQEN EFRLYYYNKF KDIASTLNKA  300
KSIVGTTASL QYMKNVFKEK YLLSEDTSGK FSVDKLKFDK LYKMLTEIYT EDNFVKFFKV  360
LNRKTYLNFD KAVFKINIVP KVNYTIYDGF NLRNTNLAAN FNGQNTEINN MNFTKLKNFT  420
GLFEFYKLLC VRGIITSKTK SLDKGYNKAL NDLCIKVNNW DLFFSPSEDN FTNDLNKGEE  480
ITSDTNIEAA EENISLDLIQ QYYLTFNFDN EPENISIENL SSDIIGQLEL MPNIERFPNG  540
KKYELDKYTM PHYLRAQEFE HGKSRIALTN SVNEALLNPS RVYTFFSSDY VKKVNKATEA  600
AMFLGWVEQL VYDFTDETSE VSTTDKIADI TIIIPYIGPA LNIGNMLYKD DFVGALIFSG  660
AVILLEFIPE IAIPVLGTFA LVSYIANKVL TVQTIDNALS KRNEKWDEVY KYIVTNWLAK  720
VNTQIDLIRK KMKEALENQA EATKAIINYQ YNQYTEEEKN NINFNIDDLS SKLNESINKA  780
MININKFLNQ CSVSYLMNSM IPYGVKRLED FDASLKDALL KYIYDNRGTL IGQVDRLKDK  840
VNNTLSTDIP FQLSKYVDNQ RLLSTFTEYI KNIIELGGGG SELSEILNNI ILNLRYKDNN  900
LIDLSGYGAK VEVDGVELN DKNQFKLTSS ANSKIRVTQN QNIIFNSVFL DFSVSFWIRI  960
PKYKNDGIQN YIHNEYTIIN CMKNNSGWKI SIRGNRIIWT LIDINGKTKS VFFEYNIRED  1020
ISEYINRWFF VTITNNLNNA KIYINGKLES NTDIKDIREV IANGEIIFKL DGDIDRTQFI  1080
WMKYFSIFNT ELSQSNIEER YKIQSYSEYL KDFWGNPLMY NKEYYMFNAG NKNSYIKLKK  1140
DSPVGEILTR SKYNQNSKYI NYRDLYIGEK FIIRRKSNSQ SINDDIVRKE DYIYLDFFNL  1200
NQEWRVYTYK YFKKEEMKLF LAPIYDSDEF YNTIQIKEYD EQPTYSCQLL FKKDEESTDE  1260
IGLIGIHRFY ESGIVFEEYK DYFCISKWYL KEVKRKPYNL KLGCNWQFIP KDEGWTEHHH  1320
HHHHHHH                                                           1327

SEQ ID NO: 11             moltype = AA   length = 1314
FEATURE                   Location/Qualifiers
REGION                    1..1314
                          note = BoNT/AB
source                    1..1314
                          mol_type = protein
```

```
                        organism = synthetic construct
SEQUENCE: 11
MPFVNKQFNY KDPVNGVDIA YIKIPNAGQM QPVKAFKIHN KIWVIPERDT FTNPEEGDLN    60
PPPEAKQVPV SYYDSTYLST DNEKDNYLKG VTKLFERIYS TDLGRMLLTS IVRGIPFWGG   120
STIDTELKVI DTNCINVIQP DGSYRSEELN LVIIGPSADI IQFECKSFGH EVLNLTRNGY   180
GSTQYIRFSP DFTFGFEESL EVDTNPLLGA GKFATDPAVT LAHELIHAGH RLYGIAINPN   240
RVFKVNTNAY YEMSGLEVSF EELRTFGGHD AKFIDSLQEN EFRLYYYNKF KDIASTLNKA   300
KSIVGTTASL QYMKNVFKEK YLLSEDTSGK FSVDKLKFDK LYKMLTEIYT EDNFVKFFKV   360
LNRKTYLNFD KAVFKINIVP KVNYTIYDGF NLRNTNLAAN FNGQNTEINN MNFTKLKNFT   420
GLFEFYKLLC VRGIITSKTK SLDKGYNKAL NDLCIKVNNW DLFFSPSEDN FTNDLNKGEE   480
ITSDTNIEAA EENISLDLIQ QYYLTFNFDN EPENISIENL SSDIIGQLEL MPNIERFPNG   540
KKYELDKYTM FHYLRAQEFE HGKSRIALTN SVNEALLNPS RVYTFFSSDY VKKVNKATEA   600
AMFLGWVEQL VYDFTDETSE VSTTDKIADI TIIIPYIGPA LNIGNMLYKD DFVGALIFSG   660
AVILLEFIPE IAIPVLGTFA LVSYIANKVL TVQTIDNALS KRNEKWDEVY KYIVTNWLAK   720
VNTQIDLIRK KMKEALENQA EATKAIINYQ YNQYTEEEKN NINFNIDDLS SKLNESINKA   780
MININKFLNQ CSVSYLMNSM IPYGVKRLED FDASLKDALL KYIYDNRGTL IGQVDRLKDK   840
VNNTLSTDIP FQLSKYVDNQ RLLSTFTEYI KNILNNIILN LRYKDNNLID LSGYGAKVEV   900
YDGVELNDKN QFKLTSSANS KIRVTQNQNI IFNSVFLDFS VSFWIRIPKY KNDGIQNYIH   960
NEYTIINCMK NNSGWKISIR GNRIIWTLID INGKTKSVFF EYNIREDISE YINRWFFVTI  1020
TNNLNNAKIY INGKLESNTD IKDIREVIAN GEIIFKLDGD IDRTQFIWMK YFSIFNTELS  1080
QSNIEERYKI QSYSEYLKDF WGNPLMYNKE YYMFNAGNKN SYIKLKKDSP VGEILTRSKY  1140
NQNSKYINYR DLYIGEKFII RRKSNSQSIN DDIVRKEDYI YLDFFNLNQE WRVYTYKYFK  1200
KEEMKLFLAP IYDSDEFYNT IQIKEYDEQP TYSCQLLFKK DEESTDEIGL IGIHRFYESG  1260
IVFEEYKDYF CISKWYLKEV KRKPYNLKLG CNWQFIPKDE GWTEHHHHHH HHHH         1314

SEQ ID NO: 12              moltype = AA   length = 1304
FEATURE                    Location/Qualifiers
REGION                     1..1304
                           note = BoNT/AB
source                     1..1304
                           mol_type = protein
                           organism = synthetic construct
SEQUENCE: 12
MPFVNKQFNY KDPVNGVDIA YIKIPNAGQM QPVKAFKIHN KIWVIPERDT FTNPEEGDLN    60
PPPEAKQVPV SYYDSTYLST DNEKDNYLKG VTKLFERIYS TDLGRMLLTS IVRGIPFWGG   120
STIDTELKVI DTNCINVIQP DGSYRSEELN LVIIGPSADI IQFECKSFGH EVLNLTRNGY   180
GSTQYIRFSP DFTFGFEESL EVDTNPLLGA GKFATDPAVT LAHELIHAGH RLYGIAINPN   240
RVFKVNTNAY YEMSGLEVSF EELRTFGGHD AKFIDSLQEN EFRLYYYNKF KDIASTLNKA   300
KSIVGTTASL QYMKNVFKEK YLLSEDTSGK FSVDKLKFDK LYKMLTEIYT EDNFVKFFKV   360
LNRKTYLNFD KAVFKINIVP KVNYTIYDGF NLRNTNLAAN FNGQNTEINN MNFTKLKNFT   420
GLFEFYKLLC VRGIITSKTK SLDKGYNKAL NDLCIKVNNW DLFFSPSEDN FTNDLNKGEE   480
ITSDTNIEAA EENISLDLIQ QYYLTFNFDN EPENISIENL SSDIIGQLEL MPNIERFPNG   540
KKYELDKYTM FHYLRAQEFE HGKSRIALTN SVNEALLNPS RVYTFFSSDY VKKVNKATEA   600
AMFLGWVEQL VYDFTDETSE VSTTDKIADI TIIIPYIGPA LNIGNMLYKD DFVGALIFSG   660
AVILLEFIPE IAIPVLGTFA LVSYIANKVL TVQTIDNALS KRNEKWDEVY KYIVTNWLAK   720
VNTQIDLIRK KMKEALENQA EATKAIINYQ YNQYTEEEKN NINFNIDDLS SKLNESINKA   780
MININKFLNQ CSVSYLMNSM IPYGVKRLED FDASLKDALL KYIYDNRGTL IGQVDRLKDK   840
VNNTLSTDIP FQLSKYVDNQ RLLSTFTEYI KNILNNIILN LRYKDNNLID LSGYGAKVEV   900
YDGVELNDKN QFKLTSSANS KIRVTQNQNI IFNSVFLDFS VSFWIRIPKY KNDGIQNYIH   960
NEYTIINCMK NNSGWKISIR GNRIIWTLID INGKTKSVFF EYNIREDISE YINRWFFVTI  1020
TNNLNNAKIY INGKLESNTD IKDIREVIAN GEIIFKLDGD IDRTQFIWMK YFSIFNTELS  1080
QSNIEERYKI QSYSEYLKDF WGNPLMYNKE YYMFNAGNKN SYIKLKKDSP VGEILTRSKY  1140
NQNSKYINYR DLYIGEKFII RRKSNSQSIN DDIVRKEDYI YLDFFNLNQE WRVYTYKYFK  1200
KEEMKLFLAP IYDSDEFYNT IQIKEYDEQP TYSCQLLFKK DEESTDEIGL IGIHRFYESG  1260
IVFEEYKDYF CISKWYLKEV KRKPYNLKLG CNWQFIPKDE GWTE                   1304

SEQ ID NO: 13              moltype = AA   length = 1304
FEATURE                    Location/Qualifiers
REGION                     1..1304
                           note = BoNT/AB
source                     1..1304
                           mol_type = protein
                           organism = synthetic construct
SEQUENCE: 13
MPFVNKQFNY KDPVNGVDIA YIKIPNAGQM QPVKAFKIHN KIWVIPERDT FTNPEEGDLN    60
PPPEAKQVPV SYYDSTYLST DNEKDNYLKG VTKLFERIYS TDLGRMLLTS IVRGIPFWGG   120
STIDTELKVI DTNCINVIQP DGSYRSEELN LVIIGPSADI IQFECKSFGH EVLNLTRNGY   180
GSTQYIRFSP DFTFGFEESL EVDTNPLLGA GKFATDPAVT LAHELIHAGH RLYGIAINPN   240
RVFKVNTNAY YEMSGLEVSF EELRTFGGHD AKFIDSLQEN EFRLYYYNKF KDIASTLNKA   300
KSIVGTTASL QYMKNVFKEK YLLSEDTSGK FSVDKLKFDK LYKMLTEIYT EDNFVKFFKV   360
LNRKTYLNFD KAVFKINIVP KVNYTIYDGF NLRNTNLAAN FNGQNTEINN MNFTKLKNFT   420
GLFEFYKLLC VRGIITSKTK SLDKGYNKAL NDLCIKVNNW DLFFSPSEDN FTNDLNKGEE   480
ITSDTNIEAA EENISLDLIQ QYYLTFNFDN EPENISIENL SSDIIGQLEL MPNIERFPNG   540
KKYELDKYTM FHYLRAQEFE HGKSRIALTN SVNEALLNPS RVYTFFSSDY VKKVNKATEA   600
AMFLGWVEQL VYDFTDETSE VSTTDKIADI TIIIPYIGPA LNIGNMLYKD DFVGALIFSG   660
AVILLEFIPE IAIPVLGTFA LVSYIANKVL TVQTIDNALS KRNEKWDEVY KYIVTNWLAK   720
VNTQIDLIRK KMKEALENQA EATKAIINYQ YNQYTEEEKN NINFNIDDLS SKLNESINKA   780
MININKFLNQ CSVSYLMNSM IPYGVKRLED FDASLKDALL KYIYDNRGTL IGQVDRLKDK   840
VNNTLSTDIP FQLSKYVDNQ RLLSTFTEYI KNILNNIILN LRYKDNNLID LSGYGAKVEV   900
```

```
YDGVELNDKN QFKLTSSANS KIRVTQNQNI IFNSVFLDFS VSFWIRIPKY KNDGIQNYIH    960
NEYTIINCMK NNSGWKISIR GNRIIWTLID INGKTKSVFF EYNIREDISE YINRWFFVTI   1020
TNNLNNAKIY INGKLESNTD IKDIREVIAN GEIIFKLDGD IDRTQFIWMK YFSIFNTELS   1080
QSNIEERYKI QSYSEYLKDF WGNPLMYNKE YYMFNAGNKN SYIKLKKDSP VGEILTRSKY   1140
NQNSKYINYR DLYIGEKFII RRKSNSQSIN DDIVRKEDYI YLDFFNLNQE WRVYTYKYFK   1200
KEEEKLFLAP ISDSDEFYNT IQIKEYDEQP TYSCQLLFKK DEESTDEIGL IGIHRFYESG   1260
IVFEEYKDYF CISKWYLKEV KRKPYNLKLG CNWQFIPKDE GWTE                   1304

SEQ ID NO: 14          moltype = AA   length = 6
FEATURE                Location/Qualifiers
REGION                 1..6
                       note = artificial
source                 1..6
                       mol_type = protein
                       organism = synthetic construct
SEQUENCE: 14
NIINTS                                                                6

SEQ ID NO: 15          moltype = AA   length = 6
FEATURE                Location/Qualifiers
REGION                 1..6
                       note = artificial
source                 1..6
                       mol_type = protein
                       organism = synthetic construct
SEQUENCE: 15
NIVNTS                                                                6

SEQ ID NO: 16          moltype = AA   length = 6
FEATURE                Location/Qualifiers
REGION                 1..6
                       note = artificial
source                 1..6
                       mol_type = protein
                       organism = synthetic construct
SEQUENCE: 16
NIVNTS                                                                6

SEQ ID NO: 17          moltype = AA   length = 6
FEATURE                Location/Qualifiers
REGION                 1..6
                       note = artificial
source                 1..6
                       mol_type = protein
                       organism = synthetic construct
SEQUENCE: 17
NITNAS                                                                6

SEQ ID NO: 18          moltype = AA   length = 6
FEATURE                Location/Qualifiers
REGION                 1..6
                       note = artificial
source                 1..6
                       mol_type = protein
                       organism = synthetic construct
SEQUENCE: 18
NIINTS                                                                6

SEQ ID NO: 19          moltype = AA   length = 6
FEATURE                Location/Qualifiers
REGION                 1..6
                       note = artificial
source                 1..6
                       mol_type = protein
                       organism = synthetic construct
SEQUENCE: 19
NIINTS                                                                6

SEQ ID NO: 20          moltype = AA   length = 6
FEATURE                Location/Qualifiers
REGION                 1..6
                       note = artificial
source                 1..6
                       mol_type = protein
                       organism = synthetic construct
SEQUENCE: 20
NIINTS                                                                6

SEQ ID NO: 21          moltype = AA   length = 6
```

```
FEATURE              Location/Qualifiers
REGION               1..6
                     note = artificial
source               1..6
                     mol_type = protein
                     organism = synthetic construct
SEQUENCE: 21
NITNTS                                                                         6

SEQ ID NO: 22        moltype = AA  length = 6
FEATURE              Location/Qualifiers
REGION               1..6
                     note = artificial
source               1..6
                     mol_type = protein
                     organism = synthetic construct
SEQUENCE: 22
EILNNI                                                                         6

SEQ ID NO: 23        moltype = AA  length = 6
FEATURE              Location/Qualifiers
REGION               1..6
                     note = artificial
source               1..6
                     mol_type = protein
                     organism = synthetic construct
SEQUENCE: 23
EILNNI                                                                         6

SEQ ID NO: 24        moltype = AA  length = 6
FEATURE              Location/Qualifiers
REGION               1..6
                     note = artificial
source               1..6
                     mol_type = protein
                     organism = synthetic construct
SEQUENCE: 24
EILNNI                                                                         6

SEQ ID NO: 25        moltype = AA  length = 6
FEATURE              Location/Qualifiers
REGION               1..6
                     note = artificial
source               1..6
                     mol_type = protein
                     organism = synthetic construct
SEQUENCE: 25
EILNNI                                                                         6

SEQ ID NO: 26        moltype = AA  length = 6
FEATURE              Location/Qualifiers
REGION               1..6
                     note = artificial
source               1..6
                     mol_type = protein
                     organism = synthetic construct
SEQUENCE: 26
DILNNI                                                                         6

SEQ ID NO: 27        moltype = AA  length = 6
FEATURE              Location/Qualifiers
REGION               1..6
                     note = artificial
source               1..6
                     mol_type = protein
                     organism = synthetic construct
SEQUENCE: 27
EILNNI                                                                         6

SEQ ID NO: 28        moltype = AA  length = 6
FEATURE              Location/Qualifiers
REGION               1..6
                     note = artificial
source               1..6
                     mol_type = protein
                     organism = synthetic construct
SEQUENCE: 28
EILNNI                                                                         6
```

```
SEQ ID NO: 29          moltype = AA   length = 6
FEATURE                Location/Qualifiers
REGION                 1..6
                       note = artificial
source                 1..6
                       mol_type = protein
                       organism = synthetic construct
SEQUENCE: 29
EILNNI                                                                    6

SEQ ID NO: 30          moltype = AA   length = 6
FEATURE                Location/Qualifiers
REGION                 1..6
                       note = artificial
source                 1..6
                       mol_type = protein
                       organism = synthetic construct
SEQUENCE: 30
NINDSK                                                                    6

SEQ ID NO: 31          moltype = AA   length = 6
FEATURE                Location/Qualifiers
REGION                 1..6
                       note = artificial
source                 1..6
                       mol_type = protein
                       organism = synthetic construct
SEQUENCE: 31
SINDSK                                                                    6

SEQ ID NO: 32          moltype = AA   length = 6
FEATURE                Location/Qualifiers
REGION                 1..6
                       note = artificial
source                 1..6
                       mol_type = protein
                       organism = synthetic construct
SEQUENCE: 32
SINDSK                                                                    6

SEQ ID NO: 33          moltype = AA   length = 6
FEATURE                Location/Qualifiers
REGION                 1..6
                       note = artificial
source                 1..6
                       mol_type = protein
                       organism = synthetic construct
SEQUENCE: 33
SINDSK                                                                    6

SEQ ID NO: 34          moltype = AA   length = 6
FEATURE                Location/Qualifiers
REGION                 1..6
                       note = arttificial
source                 1..6
                       mol_type = protein
                       organism = synthetic construct
SEQUENCE: 34
RIKSSS                                                                    6

SEQ ID NO: 35          moltype = AA   length = 6
FEATURE                Location/Qualifiers
REGION                 1..6
                       note = artificial
source                 1..6
                       mol_type = protein
                       organism = synthetic construct
SEQUENCE: 35
RIKSSS                                                                    6

SEQ ID NO: 36          moltype = AA   length = 6
FEATURE                Location/Qualifiers
REGION                 1..6
                       note = artificial
source                 1..6
                       mol_type = protein
                       organism = synthetic construct
SEQUENCE: 36
RIKSSS                                                                    6
```

```
SEQ ID NO: 37          moltype = AA   length = 6
FEATURE                Location/Qualifiers
REGION                 1..6
                       note = artificial
source                 1..6
                       mol_type = protein
                       organism = synthetic construct
SEQUENCE: 37
RIKSSS                                                                    6

SEQ ID NO: 38          moltype = AA   length = 6
FEATURE                Location/Qualifiers
REGION                 1..6
                       note = artificial
source                 1..6
                       mol_type = protein
                       organism = synthetic construct
SEQUENCE: 38
RIKSSS                                                                    6

SEQ ID NO: 39          moltype = AA   length = 6
FEATURE                Location/Qualifiers
REGION                 1..6
                       note = artificial
source                 1..6
                       mol_type = protein
                       organism = synthetic construct
SEQUENCE: 39
RIKSSS                                                                    6

SEQ ID NO: 40          moltype = AA   length = 6
FEATURE                Location/Qualifiers
REGION                 1..6
                       note = artificial
source                 1..6
                       mol_type = protein
                       organism = synthetic construct
SEQUENCE: 40
RIKSSS                                                                    6

SEQ ID NO: 41          moltype = AA   length = 6
FEATURE                Location/Qualifiers
REGION                 1..6
                       note = artificial
source                 1..6
                       mol_type = protein
                       organism = synthetic construct
SEQUENCE: 41
RIKSSS                                                                    6

SEQ ID NO: 42          moltype = AA   length = 6
FEATURE                Location/Qualifiers
REGION                 1..6
                       note = artificial
source                 1..6
                       mol_type = protein
                       organism = synthetic construct
SEQUENCE: 42
RIKSSS                                                                    6

SEQ ID NO: 43          moltype = AA   length = 6
FEATURE                Location/Qualifiers
REGION                 1..6
                       note = artificial
source                 1..6
                       mol_type = protein
                       organism = synthetic construct
SEQUENCE: 43
RIKSSS                                                                    6

SEQ ID NO: 44          moltype = AA   length = 6
FEATURE                Location/Qualifiers
REGION                 1..6
                       note = artificial
source                 1..6
                       mol_type = protein
                       organism = synthetic construct
SEQUENCE: 44
```

```
RIKSSS                                                                          6

SEQ ID NO: 45            moltype = AA  length = 6
FEATURE                  Location/Qualifiers
REGION                   1..6
                         note = artificial
source                   1..6
                         mol_type = protein
                         organism = synthetic construct
SEQUENCE: 45
RIKSSS                                                                          6

SEQ ID NO: 46            moltype = AA  length = 6
FEATURE                  Location/Qualifiers
REGION                   1..6
                         note = artificial
source                   1..6
                         mol_type = protein
                         organism = synthetic construct
SEQUENCE: 46
RIKSSS                                                                          6

SEQ ID NO: 47            moltype = AA  length = 6
FEATURE                  Location/Qualifiers
REGION                   1..6
                         note = artificial
source                   1..6
                         mol_type = protein
                         organism = synthetic construct
SEQUENCE: 47
KIKDSS                                                                          6

SEQ ID NO: 48            moltype = AA  length = 6
FEATURE                  Location/Qualifiers
REGION                   1..6
                         note = artificial
source                   1..6
                         mol_type = protein
                         organism = synthetic construct
SEQUENCE: 48
KIKDSS                                                                          6

SEQ ID NO: 49            moltype = AA  length = 6
FEATURE                  Location/Qualifiers
REGION                   1..6
                         note = artificial
source                   1..6
                         mol_type = protein
                         organism = synthetic construct
SEQUENCE: 49
KIKDNC                                                                          6

SEQ ID NO: 50            moltype = AA  length = 6
FEATURE                  Location/Qualifiers
REGION                   1..6
                         note = artificial
source                   1..6
                         mol_type = protein
                         organism = synthetic construct
SEQUENCE: 50
KIKDSS                                                                          6

SEQ ID NO: 51            moltype = AA  length = 6
FEATURE                  Location/Qualifiers
REGION                   1..6
                         note = artificial
source                   1..6
                         mol_type = protein
                         organism = synthetic construct
SEQUENCE: 51
KIKDSS                                                                          6

SEQ ID NO: 52            moltype = AA  length = 6
FEATURE                  Location/Qualifiers
REGION                   1..6
                         note = artificial
source                   1..6
                         mol_type = protein
                         organism = synthetic construct
```

```
SEQUENCE: 52
KIKDSS                                                                        6

SEQ ID NO: 53           moltype = AA  length = 6
FEATURE                 Location/Qualifiers
REGION                  1..6
                        note = artificial
source                  1..6
                        mol_type = protein
                        organism = synthetic construct
SEQUENCE: 53
NISSNA                                                                        6

SEQ ID NO: 54           moltype = AA  length = 6
FEATURE                 Location/Qualifiers
REGION                  1..6
                        note = artificial
source                  1..6
                        mol_type = protein
                        organism = synthetic construct
SEQUENCE: 54
ELKYNC                                                                        6

SEQ ID NO: 55           moltype = AA  length = 6
FEATURE                 Location/Qualifiers
REGION                  1..6
                        note = artificial
source                  1..6
                        mol_type = protein
                        organism = synthetic construct
SEQUENCE: 55
ILKKST                                                                        6

SEQ ID NO: 56           moltype = AA  length = 1286
FEATURE                 Location/Qualifiers
REGION                  1..1286
                        note = BoNT/BC
source                  1..1286
                        mol_type = protein
                        organism = synthetic construct
SEQUENCE: 56
MPVTINNFNY NDPIDNN

```
YEEISKEHLA VYKIQMCKSV KAPGICIDVD NEDLFFIADK NSFSDDLSKN ERIEYNTQSN   480
YIENDFPINE LILDTDLISK IELPSENTES LTDFNVDVPV YEKQPAIKKI FTDENTIFQY   540
LYSQTFPLDI RDISLTSSFD DALLFSNKVY SFFFSMDYIKT ANKVVEAGLF AGWVKQIVND  600
FVIEANKSNT MDKIADISLI VPYIGLALNV GNETAKGNFE NAFEIAGASI LLEFIPELLI   660
PVVGAPLLES YIDNKNKIIK TIDNALTKRN EKWSDMYGLI VAQWLSTVNT QFYTIKEGMY   720
KALNYQAQAL EEIIKYRYNI YSEKEKSNIN IDFNDINSKL NEGINQAIDN INNFINGCSV   780
SYLMKKMIPL AVEKLLDFDN TLKKNLLNYI DENKLYLIGS AEYEKSKVNK YLKTIMPFDL   840
SIYTNDTILI EMFNKYNSEI LNNIILNLRY KDNNLIDLSG YGAKVEVYDG VELNDKNQFK   900
LTSSANSKIR VTQNQNIIFN SVFLDFSVSF WIRIPKYKND GIQNYIHHNEY TIINCMKNNS  960
GWKISIRGNR IIWTLIDING KTKSVFFEYN IREDISEYIN RWFFVTITNN LNNAKIYING  1020
KLESNTDIKD IREVIANGEI IFKLGDIDR TQFIWMKYFS IFNTELSQSN IEERYKIQSY   1080
SEYLKDFWGN PLMYNKEYYM FNAGNKNSYI KLKKDSPVGE ILTRSKYNQN SKYINYRDLY  1140
IGEKFIIRRK SNSQSINDDI VRKEDYIYLD FFNLNQEWRV YTYKYFKKEE EKLFLAPISD  1200
SDEFYNTIQI KEYDEQPTYS CQLLFKKDEE STDEIGLIGI HRFYESGIVF EEYKDYFCIS  1260
KWYLKEVKRK PYNLKLGCNW QFIPKDEGWT E                                1291

SEQ ID NO: 58          moltype = AA  length = 1285
FEATURE                Location/Qualifiers
source                 1..1285
                       mol_type = protein
                       organism = Clostridium botulinum
SEQUENCE: 58
MTWPVKDFNY SDPVNDNDIL YLRIPQNKLI TTPVKAFMIT QNIWVIPERF SSDTNPSLSK    60
PPRPTSKYQS YYDPSYLSTD EQKDTFLKGI IKLFKRINER DIGKKLINYL VVGSPFMGDS   120
STPEDTFDFT RHTTNIAVEK FENGSWKVTN IITPSVLIFG PLPNILDYTA SLTLQGQQSN   180
PSFEGFGTLS ILKVAPEFLL TFSDVTSNQS SAVLGKSIFC MDPVIALMHE LTHSLHQLYG   240
INIPSDKRIR PQVSEGFFSQ DGPNVQFEEL YTFGGSDVEI IPQIERLQLR EKALGHYKDI   300
AKRLNNINKT IPSSWSSNID KYKKIFSEKY NFDKDNTGNF VVNIDKFNSL YSDLTNVMSE   360
VVYSSQYNVK NRTHYFSKHY LPVFANILDD NIYTIINGFN LTTKGFNIEN SGQNIERNPA   420
LQKLSSESVV DLFTKVCLRL TRNSRDDSTC IQVKNNTLPY VADKDSISQE IFESQIITDE   480
TNVENYSDNF SLDESILDAK VPTNPEAVDP LLPNVNMEPL NVPGEEEVFY DDITKDVDYL   540
NSYYYLEAQK LSNNVENITL TTSVEEALGY SNKIYTFLPS LAEKVNKGVQ AGLFLNWANE   600
VVEDFTTNIM KKDTLDKISD VSAIIPYIGP ALNIGNSALR GNFKQAFATA GVAFLLEGFP   660
EFTIPALGVF TFYSSIQERE KIIKTIENCL EQRVKRWKDS YQWMVSNWLS RITTQFNHIS   720
YQMYDSLSYQ ADAIKAKIDL EYKKYSGSDK ENIKSQVENL KNSLDVKISE AMNNINKFIR   780
ECSVTYLFKN MLPKVIDELN KFDLKTKTEL INLIDSHNII LVGEVDRLKA KVNESFENTI   840
PFNIFSYTNN SLLKDMINEY FNSINDSKIL SLQNKKNTLM DTSGYNAEVR VEGNVQLNPI   900
FPFDFKLGSS GDDRGKVIVT QNENIVYNAM YESFSISFWI RINKWVSNLP QTIIDSVKN   960
NSGWSIGIIS NFLVFTLKQN ENSEQDINFS YDISKNAAGY NKWFFVTITT NMMGNMMIYI  1020
NGKLIDTIKV KELTGINFSK TITFQMNKIP NTGLITSDSD NINMWIRDFY IFAKELDDKD  1080
INILFNSLQY TNVVKDYWGN DLRYDKEYYM INVNYMNRYM SKKGNGIVFN TRKNNNDFNE  1140
GYKIIIKRII GNTNDTRVRG ENVLYFNTTI DNKQYSLGMY KPSRNLGTDL VPLGALDQPM  1200
DEIRKYGSFI IQPCNTFDYY ASQLFLSSNA TTNRIGILSI GSYSFKLGDD YWFNHEYLIP  1260
VIKIEHYASL LESTSTHWVF VPASE                                       1285

SEQ ID NO: 59          moltype = AA  length = 1280
FEATURE                Location/Qualifiers
source                 1..1280
                       mol_type = protein
                       organism = Clostridium botulinum
SEQUENCE: 59
MPITINNFNY SDPVDNKNIL YLDTHLNTLA NEPEKAFRII GNIWVIPDRF SRDSNPNLNK    60
PPRVTSPKSG YYDPNYLSTD SEKDTFLKEI IKLFKRINSR EIGEELIYRL ATDIPFFPGNN  120
NTPINTFDFD VDFNSVDVKT RQGNNWVKTG SINPSVIITG PRENIIDPET STFKLTNNTF   180
AAQEGFGALS IISISPRFML TYSNATNNVG EGRFSKSEFC MDPILILMHE LNHAMHNLYG   240
IAIPNDQRIS SVTSNIFYSQ YNVKLEYAEI YAFGGPTIDL IPKSARKYFE EKALDYYRSI   300
AKRLNSITTA NPSSFNKYIG EYKQKLIRKY RFVVESSGEV AVDRNKFAEL YKELTQIFTE   360
FNYAKIYNVQ NRKIYLSNVY TPVTANILDD NVYDIQNGFN IPKSNLNVLF MGQNLSRNPA   420
LRKVNPENML YLFTKFCHKA IDGRSLYNKT LDCRELLVKN TDLPFIGDIS DIKTDIFLSK   480
DINEETEVID YPDNVSVDQV ILSKNTSEHG QLDLLYPIIE GESQVLPGEN QVFYDNRTQN   540
VDYLNSYYYL ESQKLSDNVE DFTFTTSIEE ALDNSGKVYT YPPKLADKVN TGVQGGLFLM   600
WANDVVEDFT TNILRKDTLD KISDVSAIIP YIGPALNISN SVRRGNFTEA FAVTGVTILL   660
EAFQEFTIPA LGAFVIYSKV QERNEIIKTI DNCLEQRIYN WKDSYEWMIG TWLSRITTQF   720
NNISYQMYDS LNYQADAIKD KIDLEYKKYS GSDKENIKSQ VENLKNSLDI KISEAMNNIN   780
KFIRECSVTY LFKNMLPKVI DELNKFDLKT KTELINLIDS HNIILVGEVD RLKAKINESF   840
ENTIPFNIFS YTNNSLLKDI INEYFNSIND SKILSLQNKK NALVDTSGYN AEVRLEGDVQ   900
VNTIYTNDFK LSSSGDKIIV NLNNNILSIA IYENSSVSFW IKISKDLTNS HNEYTIINSI   960
KQNSGWKLCI RNGNIEWILQ DINRKYKSLI FDYSESLSHT IVTNKWFFVT ITNNIMGYMK  1020
LYINGELKQS ERIEDLDEVK LDKTIVFGID ENIDENQMLW IRDFNIFSKE LSNEDINIVY  1080
EGQILRNVIK DYWGNPLKFD TEYYMINYNY IDRYIAPKNN ILVLVQYSDI SKLYTKNPIT  1140
IKSAANKNPY SRILNGDDIM FHMLYDSREY MIIRDTDTIY ATQGGQCSKN CVYALKLQSN  1200
LGNYGIGIFS IKNIVSQNKY CSQIFSSFMK NTMLLADIYK PWRFSFENAY TPVAVTNYET  1260
KLLSTSSFWK FISRDPGWVE                                             1280

SEQ ID NO: 60          moltype = AA  length = 1291
FEATURE                Location/Qualifiers
source                 1..1291
                       mol_type = protein
                       organism = Clostridium botulinum
```

-continued

```
SEQUENCE: 60
MPVTINNFNY NDPIDNDNII MMEPPFARGT GRYYKAFKIT DRIWIIPERY TFGYKPEDFN    60
KSSGIFNRDV CEYYDPDYLN TNDKKNIFLQ TMIKLFNRIK SKPLGEKLLE MIINGIPYLG   120
DRRVPLEEFN TNIASVTVNK LISNPGEVEQ KKGIFANLII FGPGPVLNEN ETIDIGIQNH   180
FASREGFGGI MQMKFCPEYV SVFNNVQENK GASIFNRRGY FSDPALILMH ELIHVLHGLY   240
GIKVDDLPIV PNEKKFFMQS TDTIQAEELY TFGGQDPSII SPSTDKSIYD KVLQNFRGIV   300
DRLNKVLVCI SDPNINNINY KNKFKDKYKF VEDSEGKYSI DVESFNKLYK SLMFGFTEIN   360
IAENYKIKTR ASYFSDSLPP VKIKNLLDNE IYTIEEGFNI SDKNMGKEYR GQNKAINKQA   420
YEEISKEHLA VYKIQMCKSV KVPGICIDVD NENLFFIADK NSFSDDLSKN ERVEYNTQNN   480
YIGNDFPINE LILDTDLISK IELPSENTES LTDFNVDVPV YEKQPAIKKV FTDENTIFQY   540
LYSQTFPLNI RDISLTSSFD DALLVSSKVY SFFSMDYIKT ANKVVEAGLF AGWVKQIVDD   600
FVIEANKSST MDKIADISLI VPYIGLALNV GDETAKGNFE SAFEIAGSSI LLEFIPELLI   660
PVVGVFLLES YIDNKNKIIK TIDNALTKRV EKWIDMYGLI VAQWLSTVNT QFYTIKEGMY   720
KALNYQAQAL EEIIKYKYNI YSEEEKSNIN INFNDINSKL NDGINQAMDN INDFINECSV   780
SYLMKKMIPL AVKKLLDFDN TLKKNLLNYI DENKLYLIGS VEDEKSKVDK YLKTIIPFDL   840
STYTNNEILI KIFNKYNSEI LNNIILNLRY RDNNLIDLSG YGAKVEVDG VKLNDKNQFK   900
LTSSADSKIR VTQNQNIIFN SMFLDFSVSF WIRIPKYRND DIQNYIHNEY TIINCMKNNS   960
GWKISIRGNR IIWTLIDING KTKSVFFEYN IREDISEYIN RWFFVTITNN LDNAKIYING  1020
TLESNMDIKD IGEVIVNGEI TFKLDGDVDR TQFIWMKYFS IFNTQLNQSN IKEIYKIQSY  1080
SEYLKDFWGN PLMYNKEYYM FNAGNKNSYI KLKVKDSSVGE ILIRSKYNQN SNYINYRNLY  1140
IGEKFIIRRK SNSQSINDDI VRKEDYIHLD FVNSNEEWRV YAYKNFKEQE QKLFLSIIYD  1200
SNEFYKTIQI KEYDEQPTYS CQLLFKKDEE STDDIGLIGI HRFYESGVLR KKYKDYFCIS  1260
KWYLKEVKRK PYKSNLGCNW QFIPKDEGWT E                                 1291

SEQ ID NO: 61          moltype = AA  length = 1292
FEATURE                Location/Qualifiers
source                 1..1292
                       mol_type = protein
                       organism = Clostridium botulinum
SEQUENCE: 61
MPVTINNFNY NDPIDNNNII MMEPPFARGT GRYYKAFKIT DRIWIIPERY TFGYKPEDFN    60
KSSGIFNRDV CEYYDPDYLN TNDKKNIFLQ TMIKLFNRIK SKPLGEKLLE MIINGIPYLG   120
DRRVPLEEFN TNIASVTVNK LISNPGGEER KEGIFANLII FGPGPVLNEN ETIDIGIQNH   180
FASREGFGGI MQMKFCPEYV SVFNNVQENK GASIFNRRGY FSDPALILMH ELIHVLHGLY   240
GIKVDDLPIV PNGKKFFMQS TDAIQAEELY TFGGQDPSII TPSTDKSIYD KVLQNFRGIV   300
DRLNKVLVCI SDPNININIY KNKFKDKYKF VEDSEGKYSI DVESFDKLYK SLMFGFTETN   360
IAENYKIKTR ASYFSDSLPP VKIKNLLDDE IYTIEEGFNI SDKNMGKEYR GQNKAINKQA   420
YEEISKEHLA VYKIQMCKSV RAPGICIDVD NEDLFFIADK NSFSDDLSKN ERIEYNTQSN   480
YIENDFSINE LILDTDLISK IELPSENTES LTDFNVDVPV YEKQPAIKKI FTDENTIFQY   540
LYSQTFPLDI RDISLTSSFD DALLFSNKVY SFFSMDYIKT ANKVVEAGLF AGWVKQIVDD   600
FVIEANKSNT MDKIADISLI VPYIGLALNV GNETAKGNFE NAFEIAGSSI LLEFIPELLI   660
PVVGAFLLES YIDNKNKIIK TIDNALTKRD EKWIDMYGLI VAQWLSTVNT QFYTIKEGMY   720
KALNYQAQAL EEIIKYKYNI YSEKEKSNIS IDFNDINSKL NEGINQAIDN INDFINECSV   780
SYLMKKMIPL AVEKLLDFDN TLKKNLLNYI DENKLYLIGS AEYEKSKVDK HLKTIMTFDL   840
SMYTNNTILI KMVNKYNSEI LNNIILNLRY RDNNLIDLSG YGANVEVDG VELNDKNQFK   900
LTSSTNSEIR VTQNQNIIVN SMFLDFSVSF WIRIPKYKND GIQNYIHNEY TIINCMKNNS   960
GWKISIRGNR IIWTLIDING KIKSVFFEYS IRKDVSEYIN RWFFVTITNN LDNAKIYING  1020
KLESNMDIRD IREVIANGEI IFKLDGDIDR TQFIWMKYFS IFNTELSQSN IEEIYKIQSY  1080
SEYLKDFWGN PLMYNKEYYM FNAGSKNSYI KLKKDSSVGE ILTRSKYNQN SQYINYRDLY  1140
IGEKFIIRRK SNSQSINDDI VRKEDYIYLD FFNLNQEWRV YAYKDFKGQK EQKLFLANIH  1200
DSNEFYKTIQ IKEYDEQPTY SCQLLFKKDE ESTDEIGLIG IHRFYESGFV FQEYKYYFCI  1260
SKWYLKEVKK KPYNPDLGCN WQFIPKDEGW TE                                1292

SEQ ID NO: 62          moltype = AA  length = 1291
FEATURE                Location/Qualifiers
source                 1..1291
                       mol_type = protein
                       organism = Clostridium botulinum
SEQUENCE: 62
MPVTINNFNY NDPIDNNNII MMEPPFARGT GRYYKAFKIT DRIWIIPERY TFGYKPEDFN    60
KSSGIFNRDV CEYYDPDYLN TNDKKNIFLQ TMIKLFNRIK SKPLGEKLLE MIINGIPYLG   120
DRRVPLEEFN TNIASVTVNK LISNPGEVER KKGIFANLII FGPGPVLNEN ETIDIGIQNH   180
FASREGFGGI MQMKFCPEYV SVFNNVQENK GASIFNRRGY FSDPALILMH ELIHVLHGLY   240
GIKVDDLPIV PNEKKFFMQS TDAIQAEELY TFGGQDPSII TPSTDKSIYD KVLQNFRGIV   300
DRLNKVLVCI SDPNININIY KNKFKDKYKF VEDSEGKYSI DVESFDKLYK SLMFGFTETN   360
IAENYKIKTR ASYFSDSLPP VKIKNLLDNE IYTIEEGFNI SDKDMEKEYR GQNKAINKQA   420
YEEISKEHLA VYKIQMCKSV KAPGICIDVD NEDLFFIADK NSFSDDLSKN ERIEYNTKNI   480
YIENYFSINE LILDTDLISG IELPSENTES LTDFNVDVPV YEKQPAIKKI FTDENTIFQY   540
LYSQTFPLDI RDISLTSSFD DALLFSNKVY SFFSMDYIKT ANKVVEAGLF AGWVKQIIDD   600
FVIEANKSST MDKIADISLI VPYIGLALNV GNETAKGNFE NAFEIAGASI LLEFIPELLI   660
PVVGAFLLES YIDNKNKIIK TIDNALTKRV EKWIDMYGLI VAQWLSTVNT QFYTIKEGMY   720
KALNYQAQAL EEIIKYKYNI YSEKEKLNIN IDFNDINSKL NEGINQAIDN INNFINECSV   780
SYLMKKMIPL AIEKLLDFDN ALKKNLLNYI DENKLYLIGS VEEEKSKVDK FFKTIIPFDL   840
SMYTNNTILI EMVNKYNSEI LNNIILNLRY RDNNLIDSSG YGAKVEVYNG VELNDKNQFK   900
LTSSANSKIK VTQNQNITFN SMFLDFSVSF WIRIPKYKND GIQNYIHNEY TIINCMKNNS   960
GWKISIRGNR IIWTLTDING KTKSVFFEYS IREDISDYIN RWFFVTITNN LDNAKIYING  1020
KLESNIDIRD IREVIVNGEI IFKLDGEIDR TQFIWMKYFS IFNTELSQSN VKEIYKIQSY  1080
SKYLKDFWGN PLMYNKEYYM FNAGNKNSYI KLVKDSSVGE ILTRSKYNQN SNYINYRNLY  1140
IGEKFIIRRK SSSQSISDDI VRKEDYIYLD FFNSNREWRV YAYKNFKGQE EKLFLANIYD  1200
```

```
SNEFYKTIQI KEYDEQPTYS CQLLFKKDEE STDEIGLIGI HNFYESGILF KDYKDYFCIS   1260
KWYLKEVKKK PYSSNLGCNW QFIPKDEGWT E                                 1291

SEQ ID NO: 63            moltype = AA  length = 1291
FEATURE                  Location/Qualifiers
source                   1..1291
                         mol_type = protein
                         organism = Clostridium botulinum
SEQUENCE: 63
MPVTINNFNY NDPIDNNNII MMEPPFARGT GRYYKAFKIT DRIWIIPERY TFGYKPEDFN   60
KSSGIFNRDV CEYYDPDYLN TNDKKNIFLQ TMIKLFNRIK SKPLGEKLLE MIINGIPYLG   120
DRRVPLEEFN TNIASVTVNK LISNPGEVER KKGIFANLII FGPGPVLNEN ETIDIGIQNH   180
FASREGFGGI MQMKFCPEYV SVFNNVQENK GASIFNRRGY FSDPALILMH ELIHVLHGLY   240
GIKVDDLPIV PNEKKFFMQS TDAIQAEELY TFGGQDPSII TPSTDKSIYD KVLQNFRGIV   300
DRLNKVLVCI SDPNININIY KNKFKDKYKF VEDSEGKYSI DVESFDKLYK SLMFGFTETN   360
IAENYKIKTR ASYFSDSLPP VKIKNLLDNE IYTIEEGFNI SDKNMEKEYR GQNKAINKQA   420
YEEISKEHLA VYKIQMCKSV RAPGICIDVD NEDLFFIADK NSFSDDLSKN ERIEYDTQSN   480
YIENRSSIDE LILDTNLISK IELPSENTES LTDFNVDVPV YEKQPAIKKF FTDENTIFQY   540
LYSQTFPLDI RDISLTSSFD DALLFSNKVY SFFSMDYIKT ANKVVEAGLF AGWVKQIVDD   600
FVIEANKSNT MDKLADISLI VPYIGLALNV GNETAKGNFE NAFEIAGASI LLEFIPELLI   660
PVVGAFLLES YIDNKNKIIK TIDNALTKRD EKWRDMYGLI VAQWLSTVNT QFYTIKEGMY   720
KALNYQAQAL EEIIKYKYNI YSEKEKSNIN IDFNDINSKL NEGINQAIDN INNFINECSV   780
SYLMKKMIPL AVEKLLDFDN TLKKNLLNYI DENKLYLIGS AEYEKSKVDK HLKTIIPFDL   840
SMYTNNTILI EIFKKYNSEI LNNIILNLRY RDNNLIDLSG YGANVEVDG VELNDKNQFK   900
LTSSTNSEIR VTQNQNIIFN SMFLDFSVSF WIRIPKYKND GIQNYIHNEY TIINCIKNNS   960
GWKISIRGNR IIWTLTDING KTKSVFFEYS IREDISDYIN RWFFVTITNN SDNAKIYING   1020
KLESNIDIKD IGEVIANGEI IFKLDGDIDR TQFIWMKYFS IFNTELSQSN IKEIYKIQSY   1080
SEYLKDFWGN PLMYNKEYYM FNAGNKNSYI KLKKDSPVGE ILTRSKYNQN SNYINYRNLY   1140
IGEKFIIRRK SNSQSINDDI VRKEDYIYLD FFNLNQEWRV YALKNFKKKE EKLFLAPISD   1200
SDEFYNTIQI KEYDEQPTYS CQLLFKKDEE STDEIGLIGI HRFYESGIVF KDYKYYFCIS   1260
KWYLKEVKRK PYNPNLGCNW QFIPKDEGWI E                                 1291

SEQ ID NO: 64            moltype = AA  length = 1291
FEATURE                  Location/Qualifiers
source                   1..1291
                         mol_type = protein
                         organism = Clostridium botulinum
SEQUENCE: 64
MPVTINNFNY NDPIDNNNII MMEPPFARGT GRYYKAFKIT DRIWIIPERY TFGYKPEDFN   60
KSSGIFNRDV CEYYDPDYLN TNDKKNIFLQ TMIKLFNRIK SKPLGEKLLE MIINGIPYLG   120
DRRVPLEEFN TNIASVTVNK LISNPGEVER KKGIFANLII FGPGPVLNEN ETIDIGIQNH   180
FASREGFGGI MQMKFCPEYV SVFNNVQENK GASIFNRRGY FSDPALILMH ELIHVLHGLY   240
GIKVDDLPIV PNEKKFFMQS TDAIQAEELY TFGGQDPSII TPSTDKSIYD KVLQNFRGIV   300
DRLNKVLVCI SDPNININIY KNKFKDKYKF VEDSEGKYSI DVESFDKLYK SLMFGFTETN   360
IAENYKIKTR ASYFSDSLPP VKIKNLLDNE IYTIEEGFNI SDKNMEKEYR GQNKAINKQA   420
YEEISKEHLA VYKIQMCKSV RAPGICIDVD NEDLFFIADK NSFSDDLSKN ERIEYDTQSN   480
YIENRSSIDE LILDTNLISK IELPSENTES LTDFNVDVPV YEKQPAIKKI FTDENTIFQY   540
LYSQTFPLDI RDISLTSSFD DALLFSNKVY SFFSMDYIKT ANKVVEAGLF AGWVKQIVDD   600
FVIEANKSST MDKIADISLI VPYIGLALNV GNETAKGNFE NAFEIAGASI LLEFIPELLI   660
PVVGAFLLES YIDNKNKIIK TIDNALTKRD EKWIDMYGLI VAQWLSTVNT QFYTIKEGMY   720
KALNYQAQAL EEIIKYKYNI YSEKEKSNIN IDFNDINSKL NEGINQAVDN INNFINECSV   780
SYLMKKMIPL AVEKLLDFDN TLKKNLLNYI DENKLYLIGS AEYEKSKVDK HLKTIIPFDL   840
SMYTNNTILI EIFNKYNSEI LNNIILNLRY RDNNLIDLSG YGANVEVDG VELNDKNQFK   900
LTSSTNSEIR VTQNQNIIFN SMFLDFSVSF WIRIPKYKND GIQNYIHNEY TIINCIKNNS   960
GWKISIRGNR IIWTLTDING KTKSVFFEYS IREDISDYIN RWFFVTITNN SDNAKIYING   1020
KLESNIDIKD IGEVIANGEI IFKLDGDIDR TQFIWMKYFS IFNTELSQSN IKEIYKIQSY   1080
SEYLKDFWGN PLMYNKEYYM FNAGNKNSYI KLKKDSSVGE ILTRSKYNQN SNYINYRNLY   1140
IGEKFIIRRK SNSQSINDDI VRKEDYIYLD FFNSNREWRV YAYKDFKEEE KKLFLANIYD   1200
SNEFYKTIQI KEYDEQPTYS CQLLFKKDEE STDEIGLIGI HRFYESGIVL KDYKNYFCIS   1260
KWYLKEVKRK PYNPNLGCNW QFIPKDEGWI E                                 1291

SEQ ID NO: 65            moltype = AA  length = 1291
FEATURE                  Location/Qualifiers
source                   1..1291
                         mol_type = protein
                         organism = Clostridium botulinum
SEQUENCE: 65
MPVTINNFNY NDPIDNDNII MMEPPFARGT GRYYKAFKIT DRIWIIPERY TFGYKPEDFN   60
KSSGIFNRDV CEYYDPDYLN TNDKKNIFLQ TMIKLFNRIK SKPLGEKLLE MIINGIPYLG   120
DRRVPLEEFN TNIASVTVNK LISNPGEVER KKGIFANLII FGPGPVLNEN ETIDIGIQNH   180
FASREGFGGI MQMKFCPEYV SVFNNVQENK GASIFNRRGY FSDPALILMH ELIHVLHGLY   240
GIKVDDLPIV PNEKKFFMQS TDAIQAEELY TFGGQDPRII TPSTDKSIYD KVLQNFRGIV   300
DRLNKVLVCI SDPNININIY KNKFKDKYKF VEDSEGKYSI DVESFDKLYK SLMFGFTETN   360
IAENYKIKTR ASYFSDSLPP VKIKNLLDNE IYTIEEGFNI SDKNMEKEYR GQNKAINKQA   420
YEEISKEHLA VYKIQMCKSV RAPGICIDVD NEDLFFIADK NSFSDDLSKN ERIEYDTQSN   480
YIENRSSIDE LILDTNLISK IELPSENTES LTDFNVDVPV YEKQPAIKKI FTDENTIFQY   540
LYSQTFPLDI RDISLTSSFD DALLFSNKVY SFFSMDYIKT ANKVVEAGLF AGWVKQIVDD   600
FVIEANKSST MDKIADISLI VPYIGLALNV GNETAKGNFE NAFEIAGASI LLEFIPELLI   660
PVVGAFLLES YIDNKNKIIK TIDNALTKRD EKWIDMYGLI VAQWLSTVNT QFYTIKEGMY   720
```

```
KALNYQAQAL  EEIIKYKYNI  YSEKEKSNIN  IDFNDINSKL  NEGINQAIDN  INNFINECSV   780
SYLMKKMIPL  AVEKLLDFDN  TLKKNLLNYI  DENKLYLIGS  AEYEKSKVDK  HLKTIIPFDL   840
SMYTNNTILI  EIFNKYNSEI  LNNIILNLRY  RDNNLIDLSG  YGAKVEVYNG  VELNDKNQFK   900
LTSSANSKIR  VTQNQDIIFN  SMFLDFSVSF  WIRIPKYKND  GIQNYIHNEY  TIINCIKNNS   960
GWKISIRGNK  IIWTLTDING  KTKSVFFEYS  IRKDVSEYIN  RWFFVTITNN  SDNAKIYING  1020
KLESNIDIKD  IGEVIANGEI  IFKLDGDIDR  TQFIWMKYFS  IFNTELSQSN  IKEIYKIQSY  1080
SEYLKDFWGN  PLMYNKEYYM  FNAGNKNSYI  KLKKDSSVGE  ILTRSKYNQN  SNYINYRNLY  1140
IGEKFIIRRK  SNSQSINDDI  VRKEDYIYLD  FFNLNQEWRV  YAYKDFKKKE  EKLFLANIYD  1200
SNEFYNTIQI  KEYDEQPTYS  CQLLFKKDEE  STDEIGLIGI  HRFYESGIVF  KDYKDYFCIS  1260
KWYLKEVKRK  PYNPNLGCNW  QFIPKDEGWI  E                                   1291

SEQ ID NO: 66           moltype = AA  length = 1291
FEATURE                 Location/Qualifiers
source                  1..1291
                        mol_type = protein
                        organism = Clostridium botulinum
SEQUENCE: 66
MPVTINNFNY  NDPIDNNNII  MMEPPFARGM  GRYYKAFKIT  DRIWIIPERY  TFGYKPEDFN    60
KSSGIFNRDV  CEYYDPDYLN  TNDKKNIFLQ  TMIKLFNRIK  SKPLGEKLLE  MIINGIPYLG   120
DRRVPLEEFN  TNIASVTVNK  LISNPGEVER  KKGIFANLII  FGPGPVLNEN  ETIDIGIQNH   180
FASREGFGGI  MQMKFCPEYV  SVFNNVQENK  GASIFNRRGY  FSDPALILMH  ELIHVLHGLY   240
GIKVNDLPIV  PNEKKFFMQS  TDAIQAEELY  TFGGQDPSII  SPSTDKSIYD  KVLQNFRGIV   300
DRLNKVLVCI  SDPNININIY  KNKFKDKYKF  VEDSEGKYSI  DVESFDKLYK  SLMFGFTETN   360
IAENYKIKTR  ASYFSDSLPP  VKIKNLLDNE  IYTIEEGFNI  SDKNMEKEYR  GQNKAINQA    420
YEEISKEHLA  VYKIQMCKSV  KAPGICIDVD  NEDLFFIADK  NSFSDDLSKN  ERIAYNTQNN   480
YIENDDSINE  LILDTDLISK  IELPSENTES  LTDFNVYVPV  YKKQPAIKKI  FTDENTIFQY   540
LYSQTFPLDI  RDISLTSSFD  DALLFSNKVY  SFFSMDYIKT  ANKVVEAGLF  AGWVKQIVDD   600
FVIEANKSST  MDKIADISLI  VPYIGLALNV  GNETAKGNFE  NAFEIAGASI  LLEFIPELLI   660
PVVGAFLLES  YIDNKNKIIE  TINSALTKRD  EKWIDMYGLI  VAQWLSTVNT  QFYTIKEGMY   720
KALNYQAQAL  EEIIKYKYNI  YSEKERSNIN  IDFNDVNSKL  NEGINQAIDN  INNFINECSV   780
SYLMKKMIPL  AVEKLLDFDN  TLRKNLLNYI  DENKLYLIGS  AEYEKSKVDK  YLKTSIPFDL   840
STYTNNTILI  EIFNKYNSDI  LNNIILNLRY  RDNKLIDLSG  YGAKVEVYDG  VKLNDKNQFK   900
LTSSANSKIR  VIQNQNIIFN  SMFLDFSVSF  WIRIPKYKND  GIQNYIHNEY  TIINCMKNNS   960
GWKISIRGNM  IIWTLIDING  KIKSVFFEYS  IKEDISEYIN  RWFFVTITNN  SDNAKIYING  1020
KLESHIDIRD  IREVIANDEI  IFKLDGNIDR  TQFIWMKYFS  IFNTELSQSN  IEEIYKIQSY  1080
SEYLKDFWGN  PLMYNKEYYM  FNAGNKNSYI  KLKKDSSVGE  ILTRSKYNQN  SKYINYRDLY  1140
IGEKFIIRRK  SNSQSINDDI  VRKEDYIYLD  FFNLNQEWRV  YMYKYFKKEE  EKLFLAPISD  1200
SDEFYNTIQI  KEYDEQPTYS  CQLLFKKDEE  STDEIGLIGI  HRFYESGIVF  KEYKDYFCIS  1260
KWYLKEVKRK  PYNSKLGCNW  QFIPKDEGWT  E                                   1291

SEQ ID NO: 67           moltype = AA  length = 1296
FEATURE                 Location/Qualifiers
source                  1..1296
                        mol_type = protein
                        organism = Clostridium botulinum
SEQUENCE: 67
MPLVNQQINY  YDPVNGVDIA  YIKIPNAGKM  QPVKAFKIHN  KVWVIPERDI  FTNPEEVDLN    60
PPPEAKQVPI  SYYDSAYLST  DNEKDNYLKG  VIKLFERIYS  TDLGRMLLIS  IVRGIPFWGG   120
GKIDTELKVI  DTNCINIIQL  DDSYRSEELN  LAIIGPSANI  IESQCSSFRD  DVLNLTRNGY   180
GSTQYIRFSP  DFTVGFEESL  EVDTNPLLGA  GKFAQDPAVA  LAHELIHAEH  RLYGIAINTN   240
RVFKVNTNAY  YEMAGLEVSL  EELITFGGND  AKFIDSLQKK  EFSLYYYNKF  KDIASTLNKA   300
KSIVGTTASL  QYMKNVFKEK  YLLSEDATGK  FLVDRLKFDE  LYKLLTEIYT  EDNFVKFFKV   360
LNRKTYLNFD  KAVFKINIVP  DVNYTIHDGF  NLRNTNLAAN  FNGQNIEINN  KNFDKLKNFT   420
GLFEFYKLLC  VRGIITSKTK  SLDEGYNKAL  NELCIKVNNW  DLFFSPSEDN  FTNDLDKVEE   480
ITSDTNIEAA  EENISLDLIQ  QYYLNFNFDN  EPENTSIENL  SSDIGQLEP   MPNIERFPNG   540
KKYELNKYTM  FHYLRAQEFK  HSNSRIILTN  SAKEALLKPN  IVYTFFSSKY  IKAINKAVEA   600
VTFVNWIENL  VYDFTDETNE  VSTMDKIADI  TIVIPYIGPA  LNIGNMIYKG  EFVEAIIFSG   660
AVILLEIVPE  IALPVLGTFA  LVSYVSNKVL  TVQTIDNALS  KRNEKWDEVY  KYIVTNWLAI   720
VNTQINLIRE  KMKKALENQA  EATKAIINYQ  YNQYTEEEKN  INFNIDDLS   SKLNESINSA   780
MININKFLDQ  CSVSYLMNSM  IPYAVKRLKD  FDASVRDVLL  KYIYDNRGTL  IGQVNRLKDK   840
VNNTLSADIP  FQLSKYVDNK  KLLSTFTEYI  KNITNASILS  IVYKDDDLID  LSRYGAEIYN   900
GDKVYYNSID  KNQIRLINLE  SSTIEVILKK  AIVYNSMYEN  FSTSFWIRIP  KYFNSISLNN   960
EYTIINCMEN  NSGWKVSLNY  GEIIWTFQDT  QEIKQRVVFK  YSQMINISDY  INRWIFVTIT  1020
NNRITKSKIY  INGRLIDQKP  ISNLGNIHAS  NKIMFKLDGC  RDPHRYIVIK  YFNLFPDKELS 1080
EKEIKDLYDN  QSNSGILKDF  WGDYLQYDKS  YYMLNLYDPN  KYVDVNNVGI  RGYMYLKGPR  1140
DNVMTTNIYL  NSSLYMGTKF  IIKKYASGNK  DNIVRNNDRV  YINVVVKNKE  YRLATNASQA  1200
GVEKILSALE  IPDVGNLSQV  VVMKSKNDQG  ITNKCKMNLQ  DNNGNDIGFI  GFHQFNNIAK  1260
LVASNWYNRQ  IERSSRTLGC  SWEFIPVDDG  WRERPL                              1296

SEQ ID NO: 68           moltype = AA  length = 1296
FEATURE                 Location/Qualifiers
source                  1..1296
                        mol_type = protein
                        organism = Clostridium botulinum
SEQUENCE: 68
MPFVNKQFNY  KDPVNGVDIA  YIKIPNAGQM  QPVKAFKIHN  KIWVIPERDI  FTNPEEGDLN    60
PPPEAKQVPV  SYYDSTYLST  DNEKDNYLKG  VTKLFERIYS  TDLGRMLLTS  IVRGIPFWGG   120
STIDTELKVI  DTNCINVIQP  DGSYRSEELN  LVIIGPSADI  INFECKSFGH  DVLNLTRNGY   180
GSTQYIRFSP  DFTFGFEESL  EVDTNPLLGA  GKFAIDPAVT  LAHELIHAGH  RLYGIAINPN   240
```

-continued

```
RVFKVNTNAY YEMSGLEVSF EELRTFGGHD AKFIDSLQEN EFRLYYYNKF KEVASILNKA    300
KSIIGTTASL QYMKNVFKEK YLLSEDTSGK FSVDKLRFDK LYKMLTEIYT EDNFVKFFKV    360
LNRKTYLNFD KAVFKMNIVP EVNYTIYDGF NLRNTNLAAN FNGQNTEINN MNFTKLKNFT    420
GLFEFYKLLC VRGIITSKTK SLDEGYNKAL NDLCIKVNNW DLFFSPSEDN FTNDLNKGEE    480
ITSDTNIEAA EENISSDLIQ QYYLTFNFDN EPENISIENL SSDIIGQLEL MPNIERFPNG    540
KKYELDKYTM FHYLRAQEFE YGNSRIVLIN SVNEALLNPS SVYTFFSSDY VKKANEATEA    600
AMFLGWVEQL VYDFTDETSE VSTMDKIADI TIIVPYIGPA LNIGNMVYKK KFEEALIFSG    660
AVILLEFVPE IVLPILGTFA LVSYTSNKVL TVRTIDNALS KRNEKWEEVY KYIVTNWLAK    720
VNTQINLIRK KMKEALENQA EATKAIINYQ YNQYTEEEKN NINFNIGDLS SKLNDSINKA    780
MININKFLDQ CSVSYLMNSM IPQGVKQLKD FDTSLRDSLL KYIYDNRGTL IGQVDRLKDK    840
VNNTLSTDIP FQLSKYADNQ RLLSTFTEYI KNIINTSILN LRYESNHLID LSRYASKINI    900
GSRVNFDPID KNQIQLFNLE SSKIEVILKN AIVYNSMYEN FSTSFWIKIP KYFSKINLNN    960
EYTIINCIEN NSGWKVSLNY GEIIWTLQDN EQNIQRVVFK YSQMVNISDY INRWIFVTIT   1020
NNRLTKSKIY INGRLIDQKP ISNLGNIHAS NKIMFKLDGC RDPHRYILIK YFNLFDKELN   1080
EKEIKDLYDN QSNSGILKDF WGDYLQYDKP YYMLNLYDPN KYIDVNNIGI RGYMYLKGPR   1140
GSVTTTNIYL NSMLYMGTKF IIKKHASGNK DNIVRNNDRV YINVLVKNKE YRLATNASQA   1200
GGEKILSAVE IPDVGNLSQV VVMKSKNDQG IRNKCKMNLQ DNNGNDIGFI GFHQFNNIAK   1260
LVASNWYNRQ IGKTSVTLGC SWELIPVDYG WGESSL                             1296

SEQ ID NO: 69          moltype = AA   length = 1296
FEATURE                Location/Qualifiers
source                 1..1296
                       mol_type = protein
                       organism = Clostridium botulinum
SEQUENCE: 69
MPFVNKQFNY KDPVNGVDIA YIKIPNAGQM QPVKAFKIHN KIWVIPERDT FTNPEEGDLN     60
PPPEAKQVPV SYYDSTYLST DNEKDNYLKG VTKLFERIYS TDLGRMLLTS IVRGIPFWGG    120
STIDTELKVI DTNCINVIQP DGSYRSEELN LVIIGPSADI IQFECKSPGH EVLNLTRNGY    180
GSTQYIRFSP DFTFGFEESL EVDTNPLLGA GKFATDPAVT LAHELIHAGH RLYGIAINPN    240
RVFKVNTNAY YEMSGLEVSF EELRTFGGHD AKFIDSLQEN EFRLYYYNKF KDIASTLNKA    300
KSIVGTTASL QYMKNVFKEK YLLSEDTSGK FSVDKLKFDK LYKMLTEIYT EDNFVKFFKV    360
LNRKTYLNFD KAVFKINIVP KVNYTIYDGF NLRNTNLAAN FNGQNTEINN MNFAKLKNFT    420
GLFEFYKLLC VRGIITSKTK SLDKGYNKAL NDLCIKVNNW DLFFSPSEDN FTNDLNKGEE    480
ITSDTNIEAA EENISLDLIQ QYYLTFNFDN EPENISIENL SSDIIGQLEL MPNIERFPNG    540
KKYELDKYTM FHYLSAQEFE HGKSRIDLTN SVNEALLNPS HVYTFFSSDY VKKVNKATEA    600
AMFLGWVEQL VYDFTDETSE VSTTDKIADI TIIIPYIGPA LNIGNMLYKD DFVGALIFSG    660
AVILLEFIPE IAIPVLGTFA IVSYIANKVL TVQTINNALS KRNEKWDEVY KYTVTNWLAK    720
VNTQIDLIRE KMKKALENQA EATKAIINYQ YNQYTEEEKN NINFNIDDLS SKLNESINSA    780
MININKFLDQ CSVSYLMNSM IPYAVKRLKD FDASVRDVLL KYIYDNRGTL IGQVDRLKDK    840
VNNTLSTDIP FQLSKYVDNQ RLLSTFTEYI KNIINTSILS LRYENNHLID LSRYASKINI    900
GSRVNFDPID KNQIQLFNLE SSKIEVILKN AIVYNSMYEN FSTSFWIKIP KYFSEISLNN    960
EYTIINCIEN NSGWKVSLNY GEIIWTLQDN KQNIQRVVFK YSQMVAISDY INRWIFITIT   1020
NNRLTKSKIY INGRLIDQKP ISNLGNIHAS NKIMFKLDGC RDPRRYIMIK YFNLFDKELN   1080
EKEIKDLYDS QSNSGILKDF WGNYLQYDKP YYMLNLFDPN KYVDVNNVGI RGYMYLKGSR   1140
STLLTTNIYL NSGLYMGTKF IIKKYASGNK DNIVRNNDRV YINVVVNNKE YRLATNASQA   1200
GVEKILSALE IPDIGNLSQV VVMKSKNDQG IRNKCKMNLQ DNNGNDIGFI GFHKFNDIYK   1260
LVASNWYNRQ IEISSRTFGC SWEFIPVDDG WGEKPL                             1296

SEQ ID NO: 70          moltype = AA   length = 1296
FEATURE                Location/Qualifiers
source                 1..1296
                       mol_type = protein
                       organism = Clostridium botulinum
SEQUENCE: 70
MLFVNKQFNY KDPVNGVDIA YIKIPNAGQM QPVKAFKIHN KIWVIPERDT FTNPEEGDLN     60
PPPEAKQVPV SYYDSTYLST DNEKDNYLKG VTKLFERIYS TELGRMLLTS IVRGIPFWGG    120
STIDTELKVI DTNCINVIQP DGSYRSEELN LVIIGPSADI IQFECKSPGH DVLNLTRNGY    180
GSTQYIRFSP DFTFGFEESL EVDTNPLLGA GKFATDPAVT LAHELIHAGH RLYGIAINPN    240
RVFKVNTNAY YEMSGLEVSF EELRTFGEHD AKFIDSLQEN EFRLYYYNKF KDIASTLNKA    300
KSIVGTTASL QYMKNVFKEK YLLSEDTSGK FSVDKLKFDK LYKMLTEIYT EDNFVKFFKV    360
LNRKTYLNFD KAVFKINIVP EVNYTIYDGF NLRNTNLAAN FNGQNTEINN MNFTKLKNFT    420
GLFEFYKLLC VRGIITSKTK SLDEGYNKAL NDLCIKVNNW DLFFSPSEDN FTNDLNKGEE    480
ITSDTNIEAA EENISLDLIQ QYYLTFNFDN EPENISIENL SSDIIGQLEL MPNIERFPNG    540
KKYELDKYTM FHYLRAQEFE HGKSRIVLTN SVNEALLNPS SVYTFFSSDY VRKVNKATEA    600
AMFLGWVEQL VYDFTDETSE VSTTDKIADI TIIIPYIGPA LNIGNMLYKD DFVGALIFSG    660
AVILLEFIPE IAIPVLGTFA LVSYIANKVL TVQTIDNALS KRNEKWGEVY KYIVTNWLAK    720
VNTQIDLIRK KMKEALENQA EATKAIINYQ YNQYTEEEKN NINFNIGDLS SKLNDSINKA    780
MININKFLNQ CSVSYLMNSM IPYGVKRLED FDASLKDALL KYIYDNRGTL IGQVDRLKDK    840
VNNTLSTDIP FQLSKYVDNQ RLLSTFTEYI KNIINTSILN LRYESNHLID LSRYASEINI    900
GSKVNFDPID KNQIQLFNLE SSKIEIILKN AIVYNSMYEN FSTSFWIKIP KYFSKINLNN    960
EYTIINCIEN NSGWKVSLNY GEIIWTLQDN KQNIQRVVFK YSQMVAISDY INRWIFITIT   1020
NNRLNNSKIY INGRLIDQKP ISNLGNIHAS NNIMFKLDGC RDPHRYIWIK YFNLFDKELN   1080
EKEIKDLYDN QSNSGILKDF WGNYLQYDKP YYMLNLYDPN KYVDVNNVGI RGYMYLKGPR   1140
GSIVTTNIYL NSSLYMGTKF IIKKYASGNK DNIVRNNDRV YINVVVKNKE YRLATNASQA   1200
GVEKILSVLE IPDVGNLSQV VVMKSKNDQG IRNKCKMNLQ DNNGNDIGFI GFHQFNNIDK   1260
LVASNWYNRQ IERSSRTFGC SWEFIPVDDG WGESPL                             1296

SEQ ID NO: 71          moltype = AA   length = 1292
FEATURE                Location/Qualifiers
```

| source | 1..1292 |
| --- | --- |
| | mol_type = protein |
| | organism = Clostridium botulinum |

SEQUENCE: 71

```
MPFVNKPFNY RDPGNGVDIA YIKIPNAGQM QPVKAFKIHE GVWVIPERDT FTNPEEGDLN    60
PPPEAKQVPV SYYDSTYLST DNEKDNYLKG VIKLFDRIYS TGLGRMLLSF IVKGIPFWGG   120
STIDTELKVI DTNCINVIEP GGSYRSEELN LVITGPSADI IQFECKSFGH DVFNLTRNGY   180
GSTQYIRFSP DFTFGFEESL EVDTNPLLGA GTFATDPAVT LAHELIHAAH RLYGIAINPN   240
RVLKVKTNAY YEMSGLEVSF EELRTFGGND TNFIDSLWQK KFSRDAYDNL QNIARILNEA   300
KTIVGTTTPL QYMKNIFIRK YFLSEDASGK ISVNKAAFKE FYRVLTRGFT ELEFVNPFKV   360
INRKTYLNFD KAVFRINIVP DENYTINEGF NLEGANSNGQ NTEINSRNFT RLKNFTGLFE   420
FYKLLCVRGI IPFKTKSLDE GYNKALNYLC IKVNNWDLFF SPSEDNFTND LDKVEEITAD   480
TNIEAAEENI SSDLIQQYYL TFDFDNEPEN ISIENLSSDI IGQLEPMPNI ERFPNGKKYE   540
LDKYTMFHYL RAQEFEHGDS RIILTNSAEE ALLKPNVAYT FFSSKYVKKI NKAVEAVIFL   600
SWAEELVYDF TDETNEVTTM DKIADITIIV PYIGPALNIG NMVSKGEFVE AILFTGVVAL   660
LEFIPEYSLP VFGTFAIVSY IANKVLTVQT INNALSKRNE KWDEVYKYTV TNWLAKVNTQ   720
IDLIREKMKK ALENQAEATR AIINYQYNQY TEEEKNNINI NIDDLSSKLN RSINRAMINI   780
NKFLDQCSVS YLMNSMIPYA VKRLKDFDAS VRDVLLKYIY DNRGTLILQV DRLKDEVNNT   840
LSADIPFQLS KYVNDKKLLS TFTEYIKNIV NTSILSIVYK KDDLIDLSRY GAKINIGDRV   900
YYDSIDKNQI KLINLESSTI EVILKNAIVY NSMYENFSTS FWIKIPKYFS KINLNNEYTI   960
INCIENNSGW KVSLNYGEII WTLQDNKQNI QRVVFKYSQM VNISDYINRW MFVTITNNRL  1020
TKSKIYINGR LIDQKPISNL GNIHASNKIM FKLDGCRDPR RYIMIKYFNL FDKELNEKEI  1080
KDLYDSQSNP GILKDFWGNY LQYDKPYYML NLFDPNKYVD VNNIGIRGYM YLKGPRGSVM  1140
TTNIYLNSTL YMGTKFIIKK YASGNEDNIV RNNDRVYINV VVKNKEYRLA TNASQAGVEK  1200
ILSALEIPDV GNLSQVVVMK SKDDQGIRNK CKMNLQDNNG NDIGFVGPHL YDNIAKLVAS  1260
NWYNRQVGKA SRTFGCSWEF IPVDDGWGES SL                                1292
```

| SEQ ID NO: 72 | moltype = AA length = 1296 |
| --- | --- |
| FEATURE | Location/Qualifiers |
| source | 1..1296 |
| | mol_type = protein |
| | organism = Clostridium botulinum |

SEQUENCE: 72

```
MPFVNKQFNY KDPVNGVDIA YIKIPNAGQM QPVKAFKIHN KIWVIPERDT FTNPEEGDLN    60
PPPEAKQVPV SYYDSTYLST DNEKDNYLKG VTKLFERIYS TDLGRMLLTS IVRGIPFWGG   120
STIDTELKVI DTNCINVIQP DGSYRSEELN LVIIGPSADI IQFECKSFGH DVLNLTRNGY   180
GSTQYIRFSP DFTFGFEESL EVDTNPLLGA GKFATDPAVT LAHELIHAEH RLYGIAINPN   240
RVFKVNTNAY YEMSGLEVSF EELRTFGGHD AKFIDSLQEN KDVASTLNKA   300
KSIIGTTASL QYMKNVFKEK YLLSEDTSGK FSVDKLKFDK LYKMLTEIYT EDNFVNFFKV   360
INRKTYLNFD KAVFRINIVP DENYTIKDGF NLKGANLSTN FNGQNTEINS RNFTRLKNFT   420
GLFEFYKLLC VRGIIPFKTK SLDEGYNKAL NDLCIKVNNW DLFFSPSEDN FTNDLDKVEE   480
ITADTNIEAA EENISLDLIQ QYYLTFDFDN EPENISIENL SSDIIGQLEP MPNIERFPNG   540
KKYELDKYTM FHYLRAQEFE HGDSRIILTN SAEEALLKPN VAYTFFSSKY VKKINKAVEA   600
FMFLNWAEEL VYDFTDETNE VTTMDKIADI TIIVPYIGPA LNIGNMLSKG EFVEAIIFTG   660
VVAMLEFIPE YALPVFGTFA IVSYIANKVL TVQTINNALS KRNEKWDEVY KYTVTNWLAK   720
VNTQIDLIRE KMKKALENQA EATKAIINYQ YNQYTEEEKN NINFNIDDLS SKLNESINSA   780
MININKFLDQ CSVSYLMNSM IPYAVKRLKD FDASVRDVLL KYIYDNRGTL VLQVDRLKDE   840
VNNTLSADIP FQLSKYVDNK KLLSTFTEYI KNIVNTSILS IVYKKDDLID LSRYGAKINI   900
GDRVYYDSID KNQIKLINLE SSTIEVILKN AIVYNSMYEN FSTSFWIKIP KYFSKINLNN   960
EYTIIINCIEN NSGWKVSLNY GEIIWTLQDN KQNIQRVVFK YSQMVNISDY INRWIFVTIT  1020
NNRLTKSKIY INGRLIDQKP ISNLGNIHAS NKIMFKLDGC RDPRRYIMIK YFNLFDKELN  1080
EKEIKDLYDS QSNSGILKDF WGNYLQYDKP YYMLNLFDPN KYVDVNNIGI RGYMYLKGPR  1140
GSVVTTNIYL NSTLYEGTKF IIKKYASGNE DNIVRNNDRV YINVVVKNKE YRLATNASQA  1200
GVEKILSALE IPDVGNLSQV VVMKSKDDQG IRNKCKMNLQ DNNGNDIGFI GPHLYDNIAK  1260
LVASNWYNRQ VGKASRTFGC SWEFIPVDDG WGESSL                            1296
```

| SEQ ID NO: 73 | moltype = AA length = 1297 |
| --- | --- |
| FEATURE | Location/Qualifiers |
| source | 1..1297 |
| | mol_type = protein |
| | organism = Clostridium botulinum |

SEQUENCE: 73

```
MPFVNKQFNY KDTVNGIDIA YIKIPNAGQM QPVKAFKIHN KIWVIPERDT FTNPKEGDLN    60
PPPEAKQVPV SYYDSTYLST DNEKDNYLKG VTKLFERIYS TDLGRMLLTS IVRGIPFWGG   120
STIDTELKVI DTNCINVIQP DGSYRSEELN LVIIGPSADI IQFECKSFGH DVLNLTRNGY   180
GSTQYIRFSP DFTFGFEESL EVDTNPLLGA GKFATDPAVT LAHELIHAEH RLYGIAINPN   240
RVFKVNTNAY YEMSGLEVSF EELRTFGGHN AKFIDSLQEN EFRLYYYNKF KDIASTLNKA   300
KSIVGTTASL QYMKNVFKEK YLLSEDTSGK FSVDKLKFDK LYKMLTEIYT EDNFVKFFKV   360
LNRKTYLNFD KAVFKINIVP DENYTIKDGF NLKNTNLAAN FNGQNTEINS RNFTKLKNFT   420
GLFEFYKLLC VRGIIPFKTK SLDEGYNKAL NDLCIKVNNW DLFFSPSEDN FTNDLDKVEE   480
ITSDTNIEAA EENISLDLIQ QYYLTFDFDN EPENISIENL SSDIIGQLEP MPNIERFPNG   540
KKYELDKYTM FHYLRAQEFE HSKSRIALTN SVNEALLNPS RVYTFFSSDY VKKVNKATEA   600
AMFLGWVEQL VYDFTDETSE VSTTDKIADI TIIIPYIGPA LNIGNMLYKD DFVGALIFSG   660
AVILLEFIPE IAIPVLGTFA LVSYIANKVL TVQTIDNALS KRNEKWDEVY KYIVTNWLAK   720
VNTQIDLVRK KMKEALENQA EATKAIINYQ YNQYTEEEKN NINFNIDDLS SKLNESINSA   780
MTNINKFLDQ CSVSYLMNSM IPYAVKRLKD FDASVREVLL KYIYDNRGTL ILQVDRLKDK   840
VNNTLSADIP FQLSKYVDNK KLLSTFTEYI KNITNTSILS IVVDKDGRLI DLSRYGAEIY   900
NGDKVSYNSI DKNQIKLINL ESSAIEVILK NAIVYNSMYE NFSTSFWIKI PKYFSKINLN   960
NEYTIINCIE NNSGWKVSLN YGEIIWTLQD NQQNIQRVVF KYSQMVNISD YINRWIFVTI  1020
```

-continued

```
TNNRLDKSKI YINGRLIDQK PISNLGNIHA SNNIMFKLDG CRDPRRYIVI KYFNLFDKEL  1080
NEKEIKDLYD NQSNSGILKD FWGDYLQYDK PYYMLNLYDP NKYVDVNNIG IRGYMYLKGP  1140
RGSVVTTNIY LNSTLYMGTK FIIKKYASGN KDNIVRNNDR VYINVVVKNK EYRLATNALQ  1200
AGVEKILSAL EIPDVGNLSQ VVVMKSKNDQ GIRNKCKMNL QDNNGNDIGL IGFHQFNNIA  1260
KLVASNWYNR QVGKASRTFG CSWEFIPVDD GWGESSQ                          1297

SEQ ID NO: 74           moltype = AA  length = 1288
FEATURE                 Location/Qualifiers
source                  1..1288
                        mol_type = protein
                        organism = Clostridium botulinum
SEQUENCE: 74
MPVVINSFNY DDPVNDNTII YIRPPYYETS NTYFKAFQIM DNVWIIPERY RLGIDPSLFN  60
PPVSLKAGSD GYFDPNYLST NTEKNKYLQI MIKLFKRINS KPAGQILLEE IKNAIPYLGN  120
SYTQEEQFTT NNRTVSFNVK LANGNIVQQM ANLIIWGPGP DLTTNKTGGI IYSPYQSMEA  180
TPYKDGFGSI MTVEFSPEYA TAFNDISIAS HSPSLFIKDP ALILMHELIH VLHGLYGTYI  240
TEYKITPNVV QSYMKVTKPI TSAEFLTFGG RDRNIVPQSI QSQLYNKVLS DYKRIASRLN  300
KVNTATALIN IDEFKNLYEW KYQFAKDSNG VYSVDLNKFE QLYKKIYSFT EFNLAYEFKI  360
KTRLGYLAEN FGPFYLPNLL DDSIYTEVDG FNIGALSINY QGQNIGSDIN SIKKLQGQGV  420
VSRVVRLCSN SNTKNSLCIT VNNRDLFFIA SQESYGENTI NTYKEIDDTT TLDPSFEDIL  480
DKVILNFNEQ VIPQMPNRNV STDIQKDNYI PKYDYNRTDI IDSYEVGRNY NTFFYLNAQK  540
FSPNESNITL TSSFDTGLLE GSKVYTFFSS DFINNINKPV QALLFIEWVK QVIRDFTTEA  600
TKTSTVDKLK DISLVVPYIG LALNIGDEIY KQHFAEAVEL VGAGLLLEFS PEFLIPTLLI  660
FTIKGYLTGS IRDKDKIIKT LDNALNVRDQ KWKELYRWVV SKWLTTINTQ FNKRKEQMYK  720
ALKNQATAIK KIIENKYNNY TTDEKSKIDS SYNINEIERT LNEKINLAMK NIEQFITESS  780
IAYLINIINN ETIQKLKSYD DLVRRYLLGY IRNHSSILGN SVEELNSKVN NHLDNGIPFE  840
LSSYTNDSLL IRYFNKNYGE LKYNCILNIK YEMDRDKLVD SSGYRSRINI GTGVKFSEID  900
KNQVQLSNLE SSKIEVILNN GVIYNSMYEN FSTSFWIRIP KYFRNINNEY KIISCMQNNS  960
GWEVSLNFSN MNSKIIWTLQ DTEGIKKTVV FQYTQNINIS DYINRWIFVT ITNNRLSNSK  1020
IYINGRLINE ESISDLGNIH ASNNIMFKLD GCRDPHRYIW IKYFNLFDKE LNKKEIKDLY  1080
DNQSNSGILK DFWGDYLQYD KPYYMLNLYD PNKYLDVNNV GIRGYMYLKG PRGRIVTTNI  1140
YLNSTLYMGT KFIIKKYASG NKDNIVRNND RVYINVVVKN KEYRLATNAS QAGVEKILSA  1200
VEIPDVGNLS QVVVMKSEND QGIRNKCKMN LQDNNGNDIG FIGFHQFNNI AKLVASNWYN  1260
RQIGKASRTF GCSWEFIPVD DGWGESSL                                    1288

SEQ ID NO: 75           moltype = AA  length = 1251
FEATURE                 Location/Qualifiers
source                  1..1251
                        mol_type = protein
                        organism = Clostridium botulinum
SEQUENCE: 75
MPKINSFNYN DPVNDNTILY IKPGGCQQFY KSFNIMKNIW IIPERNVIGT IPQNFLPPTS  60
LKNGDSSYYD PNYLQNDQEK DRFLKIVTKV FNRINDNLSG RILLEELSKA NPYLGNDNTR  120
DDDDFIINDGS AVPIQFSNGS QSILLPTVII MGAEPDLFET NSSNVSLINN YSPSNHGFGS  180
IAIVTFSPEY SFRFNDNSMN EFIQDPALTL IHELIHSLHG LYGAKGITTK YTITQQQNPL  240
ITNIRGINIE EFLTFGGNNL NIITSSQLND IYTNLLDDYK KIASKLSKVQ VSNPQLNPYK  300
DVFQEKYGLD KNASGIYSVN INKFNDIFKK LYSFTEFDLA KFQVKCRET YIGQYKYFKL  360
SNLLNDSIYN ISEGYNINTL NVNFRGQNPN LNPRIITPIT DRGLVKKIIR FCKNIVSVKG  420
IRKSICIEVN NGDLFFVASE KSYNNDSINI PKEIDDTVTL NNNYENDLDQ VILNFNSESA  480
PGLSDKKLNI SIQDDVYIPK YDSNGTSDIE QYDVSELNVF FYLDAQKVPE GENNVNLTSS  540
IDTALLEQSK IYTFFSSEFI NNVNKPVQAA LFVGWIQQVL VDFTTEATQK STVDKIADIS  600
IVVPYIGLAL NIGNESQKGN FKDALELLGA GILLEFVPEL LIPTILVFTI KSFLGSSDNK  660
NKVIKAINNA LKERDEKWKE VYSFIVSNWI TKINTQFNKR KEQMYQALQN QVNALKTIIE  720
SKYNSYTLEE KNELTNKYDI EQIENELNQK VSIAMNNIDR FLTESSISYL MKLINEVKIN  780
KLREYDENVK TYLLDYITKH GSILGESQQE LNSMIIDTIK NSIPFKLSSY TDDKILISYF  840
NKFFKTIKSS SVLSMRYKND KYIDTSGYDS NININGDVFI YPTNKNQFGI YNSKLSEVNI  900
SQNDYIIYDN KYKNFSISFW VRIPNYNNKI VVNNEYTII NCMRDNNSGW KISLNHNEII  960
WTLQDNAGIN QKLVFKYGNA NGISDYINKW IFVTITNDRL GYSKLYINGH LIDQKSILNL  1020
GNIHVSDNIL FKIVNCSYTR YIGMRYFNIF DKELDETEIQ TLYNNEPNAN VLKDFWGFNL  1080
LYNKEYYLLN MLKPSKTISH NRDLTFSIYN NRNIVNGLYR LYSGIKVKIQ KINDSDTRDN  1140
IVRDNDQVYV NYINGNVYYS LYADTNATNK EKTIKSSTSG NRFNQVVVMN SVRNNCTMNF  1200
KNNNGHDIGL LGFKSNALVA STWYYTNMRD HTNSNGCFWS FIPEENGWQE H           1251

SEQ ID NO: 76           moltype = AA  length = 1254
FEATURE                 Location/Qualifiers
source                  1..1254
                        mol_type = protein
                        organism = Clostridium botulinum
SEQUENCE: 76
MLYMPKINSF NYNDPVNDRT ILYIKPGGCQ QFYKSFNIMK NIWIIPERNV IGTIPQDFQP  60
PTSLKNGDSS YYDPNYLQSN EEKDRFLKIV TKIFNRINDN LSGGILLEEL SKANPYLGND  120
NTPDGDFIIN DASAVPIQFS NGSQSILLPN VIIMGAEPDL FETNSSNISL INNYRPSNHG  180
FGSIAIVTFS PEYSFRFNDN SMNEFIQDPA LTLMHELIHS LHGLYGAKGI TTKYTITQQQ  240
NSLITNIRGI NIEEFLTFGG NDLNIITSSQ FNDIYTNLLD DYKKIASKLS QVRVSNPLNN  300
PYKDVFQEKY GLDKDASGIY SVNINKFNDI FKKLYSFTEF DLATKFQVKC RETYIGQYKY  360
FQLSNLLNDS IYNISEGYNI NNLKVNFRGQ NANLNPRIIT PITGRGLVKK IIRFCKNIVS  420
VKGIRKSICI EVNNNGELFF VASENSYNDD INTPKEIDDT VTSNNNYEND LDQVILNFNS  480
ESAPGLSDEK LNLTIQDDAY IPKYDSNGTS DIEQHDVNEL NVFFYLDAQK VPEGENNVNL  540
TSSIDTALLE QPKIYTFFSS EFINNVNKPV QAVLFVSWIQ QVLVDFTTEA TQKSTVDKIA  600
```

```
DISIVVPYIG LALNIGNEAQ KGNFKDALEL LGAGILLEFV PELLIPTILV FTIKSFLGSS    660
DNKNKIIKAI NNALKERDEK WKEVYSFIVS NWITKINTQF NKRKEQMYQA LQNQVNAIKT    720
IIESKYNSYT LEEKNELTNK YDIKQIENEL NQKVSIAMNN IDRFLTESSI SYLMKLINEV    780
KINKLREYDE NVKTYLLNYI IQHGSTLGES QQELNSMVIN TLNNSIPFKL SSYTDDKILI    840
SYFNKFFKRI KSSSVLNMRY KNDKYVDTSG YDSNININEI IFIYPTNKNQ FSIFNSKPSE    900
VNISQNDYII YDNKYKNFSI SFWVRIPNYD NKIVNVNNEY TIINCMRDNN SGWKVSLNHN    960
EIIWTLQDNA GINQKLAFNY GNSNGISDYI NKWIFVTITN DRLGDSKLYI NGNLIDQKSI   1020
LNLGNIHVSD NILFKIVNCS YTRYIGIRYF NIFDKELDET EIQTLYSNEP NTNILKDFWG   1080
NYLLYDKEYY LLNVLKPNSI ISHRRDLTFS FYNHRYIVNG LYRLYSGIKV KIQRVNDSST   1140
NDQFVRKNDQ VYINYIYNNL SYSLYADTNI KDKEKTIKSS LSGNIFNQVV VMNSVGNNCT   1200
MNFKNNNGNN IGLLGFKDNT LVASTWYYTH MRDNTNSNGC FWNFISEEHG WQEK         1254

SEQ ID NO: 77           moltype = AA   length = 1252
FEATURE                 Location/Qualifiers
source                  1..1252
                        mol_type = protein
                        organism = Clostridium botulinum
SEQUENCE: 77
MPKINSFNYN DPVNDKTILY IKPGGCQQFY KSFNIMKNIW IIPERNVIGT IPQDFLPPTS     60
LKNGDSSYYD PNYLQSNEEK DRFLKIVTKI FNRINDNLSG GILLEELSKA NPYLGNDNTP    120
NNQFHIGDAS AVEIKFSNGS QSILLPTVII MGAEPDLFET NSSNISLKNN YMPSNHGFGS    180
IAIVTFSPEY SFRFNDNSMN EFIQDPALTL MHELIHSLHG LYGAKGITTK YTITQQQNPL    240
ITNIRGTNIE EFLTFGGTDL NIITNAQSND IYTNLLDDYK KIASKLSQVQ VSNPQLNPYK    300
DVFQEKYGLD KDANGIYSVN INKFNDIFKK LYSFTEFDLA TKFQVKCRKT YIGHHKYFRL    360
SDLLNDSIYN ISDGYNINTL KVNFRGQNTN LNTRIITPIT GRGVVRKIIR FCTNIFSPKG    420
IRKSICIEVN NGELFFVASE NSYNDDNINT SKEIDDTVTS NNNYENDLDQ VILNFNSESA    480
PGLSDEKLNL TIQDDAYIPK YDSNGTSDIE QYDVSELNVF FYLDAQKVPE GENNVDFTSS    540
IDTALLEQPK IYTFFSSKFI SNLNKTMQAA LFVSWIQQVL VDFTTEATQK STVDKIADIS    600
IVVPYIGLAL NIGNEAQKGN FKDALELLGA GILLEFEPEL LIPIILVFTI KSFLGSSDNK    660
NKVIKAINNA LKERDENWKE VYSFIVSNWM TKINTQFNKR KEQMYQALQN QVNAIKTIIE    720
SKYNSYTLEE KNELKNKYDI EQIENELNQT VSIAMNNIEI FLTESSISYL MKLINEVKIN    780
KLKEYDENVK TYLLDYIIKH GSILGESQQE LNSMVIDTLN NSIPFKLSSY TDDKILISYF    840
NKFFKTIKSS SVLNMRYKND KYIDTSGYDS NINIKGDVFI YPTNKNQFGI YNNKLSEVNI    900
SQNDYIIYDN KYKNFSISFW VRIPNYDNKI VNVNEYTII NCMRDNNSGW KVSLNHNEII    960
WTLQDNAGIN QKLVFKYGNA NGISDYINKW IFVTITNDRL GDSKLYIGNG LIDKKSILNL   1020
GNIHVSDNIL FKIVNCSYTR YIGMRYFNIF DKELDKTEIE TLYNNEPNTN ILKDFWGNYL   1080
LYDKEYYLLN VLKPNNVIDS NRDSTFSIHN IRSTIVLANR LYSGIKVKIQ RVNNSSTNDN   1140
LVRKNDQVYI NFVASKTHLF PLYADTNTTN KEKTIKSSSS GNRFNQVVVM NSVGNNCTMN   1200
FKNNNGNNIG MLGFKDNTLV ASTWYYTHMR DNTNSNGCFW NFISEEHGWQ EK           1252

SEQ ID NO: 78           moltype = AA   length = 1252
FEATURE                 Location/Qualifiers
source                  1..1252
                        mol_type = protein
                        organism = Clostridium botulinum
SEQUENCE: 78
MPKINSFNYN DPVNDKTILY IKPGGCQQFY KSFNIMKNIW IIPERNVIGT IPQDFLPPTS     60
LKNGDSSYYD PNYLQSNEEK DRFLKIVTKI FNRINDNLSG GILLEELSKA NPYLGNDNTP    120
NNQFHIGDAS AVEIKFSNGS QSILLPTVII MGAEPDLFET NSSNISLKNN YMPSNHGFGS    180
IAIVTFSPEY SFRFNDNSMN EFIQDPALTL MHELIHSLHG LYGAKGITTK YTITQQQNPL    240
ITNIRGTNIE EFLTFGGTDL NIITNAQSND IYTNLLADYK KIASKLSQVQ VSNPQLNPYK    300
DIFQEKYGLD KNASGIYSVN INKFDDIFKK LYSFTEFDLA TKFQVKCRQT YIGQYKYFKL    360
SNLLNNSIYN ISEGYNINTL KVNFRGQNTN LNPRIITQLT GRGLVKKIIR FCKNIVPSKG    420
ITKSICIEIN NGELFFVASE NSYNDDNINT PKEIDDTVTS NNNYENDLDQ VILNFNSESA    480
PGLSDEKLNL TIQNDAYIPK YDSNGTSDIE QHDVNELNVF FYLDAQKVPE GENNVNLTSS    540
IDTALLEQPK IYTFFSSEFI NNVNKPVQAA LFVSWIQQVL VDFTTEANQK STVDKIADIS    600
IVVPYIGLAL NIGNEAQKGN FKDALELLGA GILLEFEPEL LIPTILVFTI KSFLGSSDNK    660
NKVIKAINNA LKERDEKWKE VYSFIVSNWM TKINTQFNKR KEQMYQALQN QVNALKTIIE    720
SKYNSYTLEE KNELTNKYNI EQIENELNQK VSIAMNNIEI FLTESSISYL MKLINEVKIN    780
KLREYDENVK TYLLDYIIKH GSILGESQQE LNSMVIDTLN NSIPFKLSSY TDDKILISYF    840
NKFFKRIKSS SVLNMRYKND KYVDTSGYDS NININGDVYK YPTNKNQFGI YNDKLSEVNI    900
SQNDYIIYDN KYKNFSISFW VRIPNYDNKI VNVNNEYTII NCMRDNNSGW KVSLNHNEII    960
WTLQDNAGIN QKLAFNYGNA NGISDYINKW IFVTITNDRL GDSKLYINGG LIDKKSILNL   1020
GNIHVSDNIL FKIVNCSYTR YIGMRYFNIF DKELDKTEIE TLYNNEPNTN ILKDFWGNYL   1080
LYDKEYYLLN VLKPNNVIDS NRDSTFSIHN IRSTIVLANK LYLGIKVKIQ RVNNSSTNDN   1140
LVRKNDQVYI NFVPIKTHLF PLYADTNTTN KEKTIKSSSS GNRFNQVVVM NSVGNNCTMN   1200
FKNNNGNNIG MLGFKDNTLV ASTWYYTHMR DNTNSNGCFW NFISEEHGWQ EK           1252

SEQ ID NO: 79           moltype = AA   length = 1252
FEATURE                 Location/Qualifiers
source                  1..1252
                        mol_type = protein
                        organism = Clostridium botulinum
SEQUENCE: 79
MPKINSFNYN DPVNDKTILY IKPGGCQQFY KSFNIMKNIW IIPERNVIGT IPQDFLPPTS     60
LKNGDSSYYD PNYLQSNEEK DRFLKIVTKI FNRINDNLSG RILLEELSKA NPYLGNDNTP    120
DNQFHIGDAS AVEIKFSNGN QSILLPNVII MGAEPDLFET NSSNISLRNN YMPSNHGFGS    180
IAIVTFSPEY SFRFNDNSMN EFIQDPALTL MHELIHSLHG LYGAKRITTK YTITQQQNPL    240
ITNIRGTNIE EFLTFGGTDL NIITSAQYND IYTNLLADYK KIASKLSKVQ VSNPQLNPYK    300
```

```
DIFQEKYGLD KNASGIYSVN INKFDDIFKK LYSFTEFDLA TKFQVKCRQT YIGQYKYFKL    360
SNLLNNSIYN ISEGYNINTL KVNFRGQNTN LNPRIITQLT GRGLVKKIIR FCKNIVFSKG    420
ITKSICIEIN NGELFFVASE NSYNDDNINT PKEIDDTVTS NNNYENDLDQ VILNFNSESA    480
PGLSDEKLNL TIQNDAYIPK YDSNGTSDIE QHDVNELNVF FYLDAQKVPE GENNVNLTSS    540
IDTALLEQPK IYTFFSSEFI NNVNKPVQAA LFVSWIQQVL VDFTTEANQK STVDKIADIS    600
IVVPYIGLAL NIGNEAQKGN FKDALELLGA GILLEFEPEL LIPTILVFTI KSFLGSSDNK    660
NKVIKAINNA LKERDEKWKE VYSFIVSNWM TKINTQFNKR KEQMYQALQN QVNAIKTIIE    720
SKYNSYTLEE KNELTNKYDI KQIENELNQK VSIAMNNIDR FLTESSISYL MKLINEVKIN    780
KLREYDENVK TYLLNYIIQH GSILGESQQE LNSMVTDTLN NSIPFKLSSY TDDKILISYF    840
NKFFKRIKSS SVLNMRYKND KYVDTSGYDS NININGDVYK YPTNKNQFGI YNDKLSEVNI    900
SQNDYIIYDN KYKNFSISFW VRIPNYDNKI VNVNNEYTII NCMRDNNSGW KVSLNHNEII    960
WTLQDNAGIN QKLAFNYGNA NGISDYINKW IFVTITNDRL GDSKLYINGN LIDQKSILNL   1020
GNIHVSDNIL FKIVNCSYTR YIGIRYFNIF DKELDETEIQ TLYSNEPNTN ILKDFWGNYL   1080
LYDKEYYLLN VLKPNNFIDR RKDSTLSINN IRSTILLANR LYSGIKVKIQ RVNNSSTNDN   1140
LVRKNDQVYI NFVASKTHLF PLYADTATTN KEKTIKISSS GNRFNQVVVM NSVGNNCTMN   1200
FKNNNGNNIG LLGFKADTVV ASTWYYTHMR DHTNSNGCFW NFISEEHGWQ EK           1252

SEQ ID NO: 80           moltype = AA   length = 1252
FEATURE                 Location/Qualifiers
source                  1..1252
                        mol_type = protein
                        organism = Clostridium botulinum
SEQUENCE: 80
MPKINSFNYN DPVNDKTILY IKPGGCQQFY KSFNIMKNIW IIPERNVIGT IPQDFLPPTS     60
LKNGDSSYYD PNYLQSNEEK DRFLKIVTKI FNRINDNLSG RILLEELSKA NPYLGNDNTP    120
DNQFHIGDAS AVEIKFSNGN QSILLPNVII MGAEPDLFET MHELIHSLHG LYGAKRITTK    180
YTITQQQNPL IAIVTFSPEY SFRFNDNSMN EFIQDPALTL MHELIHSLHG LYGAKRITTK    240
ITNIRGTNIE EFLTFGGTDL NIITSAQYND IYTNLLADYK KIASKLSKVQ VSNPQLNPYK    300
DIFQEKYGLD KNASGIYSVN INKFDDIFKK LYSFTEFDLA TKFQVKCRQT YIGQYKYFKL    360
SNLLNNSIYN ISEGYNINTL KVNFRGQNTN LNPRIITQLT GRGLVKKIIR FCKNIVFSKG    420
ITKSICIEIN NGELFFVASE NSYNDDNINT PKEIDDTVTS NNNYENDLDQ VILNFNSESA    480
PGLSDEKLNL TIQNDAYIPK YDSNGTSYIE QHDVNELNVF FYLDAQKVPE GENNVNLTSS    540
IDTALLEQPK IYTFFSSEFI NNVNKTVQAA LFVSWIQQVL VDFTTEANQK STVDKIADIS    600
IVVPYIGLAL NIGNEAQKGN FKDALELLGA GILLEFEPEL LIPTILVFTI KSFLGSSDNK    660
NKVIKAINNA LKERDEKWKE VYSFIVSNWM TKINTQFNKR KEQMYQALQN QVNALKTIIE    720
SKYNSYTLEE KNELTNKYNI EQIENELNQK VSIAMNNIEI FLTESSISYL MKLINEVKIN    780
KLREYDENVK TYLLDYIIKH GSILGESQQE LNSMVIDTLN NSIPFKLSSY TDDKILISYF    840
NKFFKRIKSS SVLNMRYKND KYVDTSGYDS NININGDVYK YPTNKNQFGI YNDKLSEVNI    900
SQNDYIIYDN KYKNFSISFW VRIPNYDNKI VNVNNEYTII NCMRDNNSGW KVSLNHNEII    960
WTLQDNAGIN QKLAFNYGNA NGISDYINKW IFVTITNDRL GDSKLYINGN LIDKKSILNL   1020
GNIHVSDNIL FKIVNCSYTR YIGIRYFNIF DKELDETEIQ TLYNNEPNAN ILKDFWGNYL   1080
LYDKEYYLLN VLKPNNFIDR RTDSTLSINN IRSTILLANR LYSGIKVKIQ RVNNSSTNDN   1140
LVRKNDQVYI NFVASKTHLF PLYADTNTTN KEKTIKSSSS GNRFNQVVVM NSVGNNCTMN   1200
FKNNNGNNIG MLGFKDNTLV ASTWYYTHMR DNTSNGCFW NFISEEHGWQ EK            1252

SEQ ID NO: 81           moltype = AA   length = 1251
FEATURE                 Location/Qualifiers
source                  1..1251
                        mol_type = protein
                        organism = Clostridium botulinum
SEQUENCE: 81
MPKINSFNYN DPVNDRTILY IKPGGCQEFY KSFNIMKNIW IIPERNVIGT TPQDFHPPTS     60
LKNGDSSYYD PNYLQSDEEK DRFLKIVTKI FNRINNNLSG GILLEELSKA NPYLGNDNTP    120
DNQFHIGDAS AVEIKFSNGS QDILLPNVII MGAEPDLFET NSSNISLRNN YMPSNHGFGS    180
IAIVTFSPEY SFRFNDNSMN EFIQDPALTL MHELIHSLHG LYGAKGITTK YTITQKQNPL    240
ITNIRGTNIE EFLTFGGTDL NIITSAQSND IYTNLLADYK KIASKLSKVQ VSNPLLNPYK    300
DVFEAKYGLD KDASGIYSVN INKFNDIFKK LYSFTEFDLA TKFQVKCRQT YIGQYKYFKL    360
SNLLNDSIYN ISEGYNINNL KVNFRGQNAN LNPRIITPIT GRGLVKKIIR FCKNIVSVKG    420
IRKSICIEIN NGELFFVASE NSYNDDNINT PKEIDDTVTS NNNYENDLDQ VILNFNSESA    480
PGLSDEKLNL TIQNDAYIPK YDSNGTSDIE QHDVNELNVF FYLDAQKVPE GENNVNLTSS    540
IDTALLEQPK IYTFFSSEFI NNVNKPVQAA LFVSWIQQVL VDFTTEANQK STVDKIADIS    600
IVVPYIGLAL NIGNEAQKGN FKDALELLGA GILLEFVPEL LIPTILVFTI KSFLGSSDNK    660
NKVIKAINNA LKERDEKWKE VYSFIVSNWM TKINTQFNKR KEQMYQALQN QVNALKTIIE    720
FKYNSYTLEE KKELKNNYDI EQIENELNQK VSIAMNNIDR FLTESSISYL MKLINEVKIN    780
KLREYDENVK TYLLDYIIQH GSILGESQQE LNSMVIDTLN NSIPFKLSSY TDDKILISYF    840
NKFFKRIKSS SVLNMRYKND KYVDTSGYDS NININGEIFI YPTNKNQFTI FNSKPSEVNI    900
SQNDYIIYDN KYKNFSISFW VRIPNYDNKI VNINNEYTII NCMRDNNSGW KVSLNHNEII    960
WTLQDNARIN QKLVFKYGNA NGISDINKW IFVTITNDRL GDSKLYINGH LIDQKSILNL   1020
GNIHVSDNIL FKIVNCSYTR YIGIRYFNIF DKELDETEIQ TLYSNEPNTN ILKDFWGNYL   1080
LYDKGYYLLN VLKPNNFIDR RKDSTLSINN IRSTILLANR LYSGIKVKIQ RVNDSSTNDR   1140
FVRKNDQVYI NYISNSSSYS LYADTNTTDK EKTIKSSSSG NRFNQVVVMN SVGNNCTMNF   1200
KNNNGNNIGL LGFKADTVVA STWYYTHMRD HTNSNGCFWN FISEEHGWQE K            1251

SEQ ID NO: 82           moltype = AA   length = 1252
FEATURE                 Location/Qualifiers
source                  1..1252
                        mol_type = protein
                        organism = Clostridium botulinum
SEQUENCE: 82
```

```
MPTINSFNYN DPVNDRTILY IKPGGCQEFY KSFNIMKNIW IIPERNVIGT TPQDFHPPTS    60
LKNGDSSYYD PNYLQSYEEK DRFLKIVTKI FNRINNNLSG GILLEELSKA NPYLGNDNTP   120
DNQFHIGDAS AVEIKFSNGS QDILLPNVII MGAEPDLFET NSSNISLRNN YMPSNHGFGS   180
IAIVTFSPEY SFRFKDNSMN EFIQDPALTL MHELIHSLHG LYGAKGITTQ YTITQQQNPL   240
ITNIKGTNIE EFLTFGGTDL NIIITSAQYND IYTNLLADYK KIASKLSKVQ VSNPLLNPYK   300
DVFEKKYGLD KDASGIYSVN INKFNDIFKK LYSFTEFDLA TKFQVKCRQT YIGQYKYFKL   360
SNLLNNSIYN ISEGYNINTL KVNFRGQNTN LNPRIITPLT GRGLVKKIIR FCKNIVFSKG   420
IRKSICIEIN NGELFFVASD NSYNDDNINT PKEIDDTVTS NNNYENDLDQ VILNFNSESA   480
PGLSDEKLNL TIQNDAYIPK YDSNGTSDIE QHDVNELNVF FYLDAQKVPE GENNIDFTSS   540
IDTALLEQPK IYTFFSSEFI NNVNKPVQAA LFVSWIQQVL VDFTTEANQK STVDKIADIS   600
IVVPYIGLAL NIGNEAQKGN FKDALELLGA GILLEFEPEL LIPTILVFTI KSFLGSSDNK   660
NKVIKAINNA LKERDEKWKE VYSFIVSNWM TKINTQFNKR KEQMYALQN QVNALKTIIE   720
SKYNSYTLEE KNELTNKYNI EQIENELNQK VSIAMNNIEI FLTESSISYL MKLINEVKIN   780
KLREYDENVK TYLLDYIIKH GSILGESQQE LNSMVIDTLN NSIPFKLSSY TDDKILISYF   840
NKFFKRIKSS SVLNMRYKND KYVDTSGYDS NININGDVYK YPTNKNQFGI YNNKLSEVNI   900
SQNDYIIYDN KYKNFSISFW VRIPNYDNKI VNVNNEYTII NCMRDNNSGW KVSLNHNEII   960
WTLQDNSGIN QKLAFNYGNA NGISDYINKW IFVTITNDRL GDSKLYINGN LIDKKSILNL  1020
GNIHVSDNIL FKIVNCSYTR YIGIRYFNIF DKELDETEIQ TLYNNEPNAN ILKDFWGNYL  1080
LYDKEYYLLN VLKPNNFINR RTDSTLSINN IRSTILLANR LYSGIKVKIQ RVNNSSTNDN  1140
LVRKNDQVYI NFVDSKTHLL PLYADTATTN KEKTIKISSS GNRFNQVVVM NSVGNNCTMN  1200
FKNNNGNNIG LLGFKADTVV ASTWYYTHMR DNTNSNGFFW NFISEEHGWQ EK          1252

SEQ ID NO: 83           moltype = AA  length = 1252
FEATURE                 Location/Qualifiers
source                  1..1252
                        mol_type = protein
                        organism = Clostridium botulinum
SEQUENCE: 83
MPTINSFNYN DPVNNRTILY IKPGGCQQFY KSFNIMKNIW IIPERNVIGT IPQDFLPPTS    60
LKNGDSSYYD PNYLQSDQEK DKFLKIVTKI FNRINDNLSG RILLEELSKA NPYLGNDNTP   120
DGDFIINDAS AVPIQFSNGS QSILLPNVII MGAEPDLFET NSSNISLRNN YMPSNHGFGS   180
IAIVTFSPEY SFRFKDNSMN EFIQDPALTL MHELIHSLHG LYGAKGITTK YTITQKQNPL   240
ITNIRGTNIE EFLTFGGTDL NIIITSAQSND IYTNLLADYK KIASKLSKVQ VSNPLLNPYK   300
DVFEAKYGLD KDASGIYSVN INKFNDIFKK LYSFTEFDLA TKFQVKCRQT YIGQYKYFKL   360
SNLLNDSIYN ISEGYNINNL KVNFRGQNAN LNPRIITPIT GRGLVKKIIR FCKNIVSVKG   420
IRKSICIEIN NGELFFVASE NSYNDDNINT PKEIDDTVTS NNNYENDLDQ VILNFNSESA   480
PGLSDEKLNL TIQNDAYIPK YDSNGTSDIE QHDVNELNVF FYLDAQKVPE GENNVNLTSS   540
IDTALLEQPK IYTFFSSEFI NNVNKPVQAA LFVGWIQQVL VDFTTEANQK STVDKIADIS   600
IVVPYIGLAL NIGNEAQKGN FKDALELLGA GILLEFEPEL LIPTILVFTI KSFLGSSDNK   660
NKVIKAINNA LKERDEKWKE VYSFIVSNWM TKINTQFNKR KEQMYALQN QVNALKAIIE   720
SKYNSYTLEE KNELTNKYDI EQIENELNQK VSIAMNNIDR FLTESSISYL MKLINEVKIN   780
KLREYDENVK TYLLDYIIKH GSILGESQQE LNSMVIDTLN NSIPFKLSSY TDDKILISYF   840
NKFFKRIKSS SVLNMRYKND KYVDTSGYDS NININGDVYK YPTNKNQFGI YNDKLSEVNI   900
SQNDYIIYDN KYKNFSISFW VRIPNYDNKI VNVNNEYTII NCMRDNNSGW KVSLNHNEII   960
WTLQDNSGIN QKLAFNYGNA NGISDYINKW IFVTITNDRL GDSKLYINGN LIDKKSILNL  1020
GNIHVSDNIL FKIVNCSYTR YIGIRYFNIF DKELDETEIQ TLYNNEPNAN ILKDFWGNYL  1080
LYDKEYYLLN VLKPNNFINR RTDSTLSINN IRSTILLANR LYSGIKVKIQ RVNNSSTNDN  1140
LVRKNDQVYI NFVASKTHLL PLYADTATTN KEKTIKISSS GNRFNQVVVM NSVGNNCTMN  1200
FKNNNGNNIG LLGFKADTVV ASTWYYTHMR DNTNSNGFFW NFISEEHGWQ EK          1252

SEQ ID NO: 84           moltype = AA  length = 1252
FEATURE                 Location/Qualifiers
source                  1..1252
                        mol_type = protein
                        organism = Clostridium botulinum
SEQUENCE: 84
MPKINSFNYN DPVNDRTILY IKPGGCQEFY KSFNIMKNIW IIPERNVIGT TPQDFHPPTS    60
LKNGDSSYYD PNYLQSDEEK DRFLKIVTKI FNRINNNLSG GILLEELSKA NPYLGNDNTP   120
DNQFHIGDAS AVEIKFSNGS QHILLPNVII MGAEPDLFET NSSNISLRNN YMPSNHGFGS   180
IAIVTFSPEY SFRFNDNSIN EFIQDPALTL MHELIHSLHG LYGAKGITTT CIITQQQNPL   240
ITNRKGINIE EFLTFGGNDL NIIITVAQYND IYTNLLNDYR KIASKLSKVQ VSNPQLNPYK   300
DIFQEKYGLD KDASGIYSVN INKFDDILKK LYSFTEFDLA TKFQVKCRET YIGQYKYFKL   360
SNLLNDSIYN ISEGYNINNL KVNFRGQNAN LNPRIIKPLT GRGLVKKIIR FCKNIVSVKG   420
IRKSICIEIN NGELFFVASE NSYNDDNINT PKEIDDTVTS NNNYENDLDQ VILNFNSESA   480
PGLSDEKLNL TIQNDAYIPK YDSNGTSDIE QHDVNELNVF FYLDAQKVPE GENNVNLTSS   540
IDTALLEQPK IYTFFSSEFI NNVNKPVQAA LFVSWIQQVL VDFTTEANQK STVDKIADIS   600
IVVPYIGLAL NIGNEAQKGN FKDALELLGA GILLEFEPEL LIPTILVFTI KSFLGSSDNK   660
NKVIKAINNA LKERDEKWKE VYSFIVSNWM TKINTQFNKR KEQMYALQN QVNAIKTIIE   720
SKYNSYTLEE KNELTNKYDI KQIENELNQK VSIAMNNIDR FLTESSISYL MKLINEVKIN   780
KLREYDENVK TYLLNYIIQH GSILGESQQE LNSMVDTLN NSIPFKLSSY TDDKILISYF   840
NKFFKRIKSS SVLNMRYKND KYVDTSGYDS NININGDVYK YPTNKNQFGI YNDKLSEVNI   900
SQNDAGIN QKLAFNYGNA NGISDYINKW IFVTITNDRL GDSKLYINGN LIDQKSILNL  1020
GNIHVSDNIL FKIVNCSYTR YIGIRYFNIF DKELDETEIQ TLYSNEPNTN ILKDFWGNYL  1080
LYDKEYYLLN VLKPNNFIDR RKDSTLSINN IRSTILLANR LYSGIKVKIQ RVNNSSTNDN  1140
LVRKNDQVYI NFVASKTHLF PLYADTATTN KEKTIKISSS GNRFNQVVVM NSVGNNCTMN  1200
FKNNNGNNIG LLGFKADTVV ASTWYYTHMR DHTNSNGCFW NFISEEHGWQ EK          1252

SEQ ID NO: 85           moltype = AA  length = 1252
```

```
FEATURE                 Location/Qualifiers
source                  1..1252
                        mol_type = protein
                        organism = Clostridium botulinum
SEQUENCE: 85
MPKINSFNYN DPVNDRTILY IKPGGCQEFY KSFNIMKNIW IIPERNVIGT TPQDFHPPTS  60
LKNGDSSYYD PNYLQSDEEK DRFLKIVTKI FNRINNNLSG GILLEELSKA NPYLGNDNTP 120
DNQFHIGDAS AVEIKFSNGI QDILLPNVII MGAEPDLFET NSSNISLRNN YMPSNHGFGS 180
IAIVTFSPEY SFRFNDNSMN EFIQDPALTL MHELIHSLHG LYGAKGITTK YTITQKQNPL 240
ITNIRGTNIE EFLTFGGTDL NIITSAQSND IYTNLLADYK KIASKLSKVQ VSNPLLNPYK 300
DVFEAKYGLD KDASGIYSVN INKFNDIFKK LYSFTEFDLA TKFQVKCRQT YIGQYKYFKL 360
SNLLNDSIYN ISEGYNINNL KVNFRGQNAN LNPRIITPIT GRGLVKKIIR FCKNIVSVKG 420
IRKSICIEIN NGELFFVASE NSYNDDNINT PKEIDDTVTS NNNYENDLDQ VILNFNSESA 480
PGLSDEKLNL TIQNDAYIPK YDSNGTSDIE QHDVNELNVF FYLDAQKVPE GENNVNLTSS 540
IDTALLEQPK IYTFFSSEFI NNVNKPVQAA LFVSWIQQVL VDFTTEANQK STVDKIADIS 600
IVVPYIGLAL NIGNEAQKGN FKDALELLGA GILLEFEPEL LIPTILVFTI KSFLGSSDNK 660
NKVIKAINNA LKERDEKWKE VYSFIVSNWM TKINTQFNKR KEQMYQALQN QVNAIKTIIE 720
SKYNSYTLEE KNELTNKYDI KQIENELNQK VSIAMNNIDR FLTESSISYL MKLINEVKIN 780
KLREYDENVK TYLLNYIIQH GSILGESQQE LNSMVTDTLN NSIPFKLSSY TDDKILISYF 840
NKFFKRIKSS SVLNMRYKND KYVDTSGYDS NININGDVYK YPTNKNQFGI YNDKLSEVNI 900
SQNDYIIYDN KYKNFSISFW VRIPNYDNKI VNVNNEYTII NCMRDNNSGW KVSLNHNEII 960
WTLQDNAGIN QKLAFNYGNA NGISDYINKW IFVTITNDRL GDSKLYINGN LIDQKSILNL 1020
GNIHVSDNIL FKIVNCSYTR YIGIRYFNIF DKELDETEIQ TLYNNEPNAN ILKDFWGNYL 1080
LYDKEYYLLN VLKPNNFIDR RTDSTLSINN IRSTILLANR LYSGIKVKIQ RVNNSSTNDN 1140
LVRKNDQVYI NFVASKTHLF PLYADTNTTN KEKTIKSSSS GNRFNQVVVM NSVGNNCTMN 1200
FKNNNGNNIG MLGFKDNTLV ASTWYYTHMR DNTNSNGCFW NFISEEHGWQ EK          1252

SEQ ID NO: 86           moltype = AA  length = 1268
FEATURE                 Location/Qualifiers
source                  1..1268
                        mol_type = protein
                        organism = Clostridium botulinum
SEQUENCE: 86
MPVNINNFNY NDPINNTTIL YMKMPYYEDS NKYYKAFEIM DNVWIIPERN IIGKKPSDFY  60
PPISLDSGSS AYYDPNYLTT DAEKDRFLKT VIKLFNRINS NPAGQVLLEE IKNGKPYLGN 120
DHTAVNEFCA NNRSTVEIK ESNGTTDSML LNLVILGPGP NILECSTPV RIFPNNIAYD 180
PSEKGFGSIQ LMSFSTEYEY AFNDNTDLFI ADPAISLAHE LIHVLHGLYG AKGVTNKKVI 240
EVDQGALMAA EKDIKIEEFI TFGGQDLNII TNSTNQKIYD NLLSNYTAIA SRLSQVNINN 300
SALNTTYYKN FFQWKYGLDQ DSNGNYTVNI SKFNAIYKKL FSFTECDLAQ KFQVKNRSNY 360
LFHFKPFRLL DLLDDNIYSI SEGFNIGSLR VNNNGQNINL NSRIVGPIPD NGLVERFVGL 420
CKSIVSKKGT KNSLCIKVNN RDLFFVASES SYNENGINSP KEIDDTTITN NNYKKNLDEV 480
ILDYNSDAIP NLSSRLLNTT AQNDSYVPKY DSNGTSEIDE YTVDKLNVFF YLYAQKAPEG 540
ESAISLTSSV NTALLDASKV YTFFSSDFIN TVNKPVQAAE FISWIQQVIN DFTTEATQKS 600
TIDKIADISL VVPYVGLALN IGNEVQKGNF KEAIELLGAG ILLEFVPELL IPTILVFTIK 660
SFINSDDSKN KIIKAINNAL RERELKWKEV YSWIVSNWLT RINTQFNKRK EQMYQALQNQ 720
VDGIKKIIEY KYNNYTLDEK NRLKAEYNIY SIKEELNKKV SLAMQNIDRF LTESSISYLM 780
KLINEAKINK LSEYDKRVNQ YLLNYILENS STLGETSSVQE LNNLVSNTLN NSIPFELSEY 840
TNDKILISYF NRFYKRIIDS SILNMKYENN RFIDSSGYGS NISINGDIYI YSTNRNQFGI 900
YSSRLSEVNI TQNNTIIYNS RYQNFSVSFW VRIPKYNNLK NLNNEYTIIN CMRNNNSGWK 960
ISLNYNNIIW TLQDTTGNNQ KLVFNYTQMI DISDYINKWT FVTITNNRLG HSKLYINGNL 1020
TDQKSILNLG NIHVDDNILF KIVGCNDTRY VGIRYFKIFN MELDKTEIET LYHSEPDSTI 1080
LKDFWGNYLL YNKKYYLLNL LKPNMSVTKN SDILNINRQR GIYSKTNIFS NARLYTGVEV 1140
IIRKVGSTDT SNTDNFVRKN DTVYINVVDG NSEYQLYADV STSAVEKTIK LRRISNSNYN 1200
SNQMIIMDSI GDNCTMNFKT NNGNDIGLLG FHLNNLVASS WYYKNIRNNT RNNGCFWSFI 1260
SKEHGWQE                                                          1268

SEQ ID NO: 87           moltype = AA  length = 1277
FEATURE                 Location/Qualifiers
source                  1..1277
                        mol_type = protein
                        organism = Clostridium botulinum
SEQUENCE: 87
MPVEINSFNY DDLVNDNTIL YIRPPYYERS NTYFKAFNIM ENVWIIPERY RLGIEASKFD  60
PPDSLKAGSD GYFDPNYLST NTEKNRYLQI MIKLFKRINS NEAGKILLNQ IKDAIPYLGN 120
SYTAEDQFTT NNRTISFNVR LANGTIEQEM ANLIIWGPGP DLTTNRTGGT TYTPAQSLEA 180
IPYKEGFGSI MTIEFSPEYA TAFNDISLTS HAPSLFIKDP ALILMHELIH VLHGLYGTYT 240
TGFKIKPNIT EPYMEVTKPI TSGEFLTFGG NDVNKIPQLI QSQLRSKVLD DYEKIASRLN 300
KVNRATAEIN IDKFKYSYQL KYQFVKDSNG VYSVDLDKRN KLYDKIYSFT EFNLAHEFKI 360
KTRNSYLAKN FGPFYLPNLL DNSIYNEADS FNIGDLSVNY KGQVIGSDID SIKKLEGQGV 420
VSRVVRLCLN SSFKKNTKKP LCITVNNGDL FFIASEDSYG EDTINTPKEI DDTTTLVPSF 480
KNILDKVILD FNKQVTPQIP NRRIRTDIQE DNYIPEYDSN GTSEIEEYNV VDLNAFFYLH 540
AQKVPEGETN ISLTSSIDTA LSEESKVYTF FSSEFIDTIN EPVNAALFID WISKVIRDFT 600
TEATQKSTVD KIADISLIVP YVGLALNIVN ETEKGNFKEA FELLGAGILL EFVPELAIPV 660
ILVFTIKSYI DSYENKNKII KAINNSLIER EAKWKEIYSW IVSNWLTRIN TQFNKRKEQM 720
YQALQNQVDA IKTAIEYKYN NYTSDEKNRL ESEYNINNIE EELNKKVSLA MKNIERFITE 780
SSISYLMKLI NEAVGKLKE YDKRVKRHLL EYIFDYRLIL GEQGGELIDL VTSTLNTSIP 840
FELSSYTNDK ILIIYFNRLY KKIKDSSILD MRYENNKFID ISGYGSNISI NGNVYIYSTN 900
RNQFGIYDDR LSEVNIAQNN DIIYNSRYQN FSISFWVRIP KHYRPMNHNR EYTIINCMGN 960
NNSGWKISLR TTGDCEIIWT LQDTSGNKKK LIFRYSQLGG ISDYINKWIF VTITNNRLGN 1020
```

```
SRIYINGNLI VEKSISNLGD IHVSDNILFK IVGCDDKMYV GIRYFKVFNT ELDKTEIEIL    1080
YSNEPDPSIL KDYWGNYLLY NKKYYLLNLL RNDKYITRNS DILNISHQRG VTKDLFIFSN    1140
YKLYEGVEVI IRKNGPIDIS NTDNFVRKND LAYINVVDHG VEYRLYADIS ITKPEKIIKL    1200
IRRSNPDDSL GQIIVMDSIG NNCTMNFQNN NGGNIGLLGF HSDNLVASSW YYNNIRRNTS    1260
SNGCFWSFIS KEHGWQE                                                  1277

SEQ ID NO: 88           moltype = AA  length = 1277
FEATURE                 Location/Qualifiers
source                  1..1277
                        mol_type = protein
                        organism = Clostridium botulinum
SEQUENCE: 88
MPVVINSFNY DDPVNDDTIL YMQIPYEEKS KKYYKAFEIM RNVWIMPERN TIGTNPSDFD      60
PPASLKNGSS AYYDPNYLTT DAEKDRYLKT TIKLFKRINS NPAGEVLLQE ISYAKPYLGN     120
DHTPINEFHP VTRTTSVNIK SSTNVESSII LNLLVLGAGP NIFENSSYPV RKLMNSGEVY     180
DPSNDGFGSI NIVTFSPEYE YTFNDISGGH NSSTESFIAD PAISLAHELI HALHGLYGAR     240
GVTYKETIKV KQAPLMIAEK PIRLEEFLTF GGQDLNIITS AMKEKIYNDL LANYEKIATR     300
LSEVNSAPPE YDINEYKNYF QWKYGLDKNA DGSYTVNENK FNEIYKKLYS FTEIDLANKF     360
KVKCRNTYFI KYGFLKVPNL LDDDIYTVSE GFNIGNLAVN NRGQNINLNP KIIDSIPDKG     420
LVEKIVKLCK SIIPRKGTKA PPRLCIRVNN RELFFVASES SYNENDINTP KEIDDTTNLN     480
NNYRNNLDEV ILDYNSETIP QISSQTLNTL VQDDSYVPRY DSNGTSEIEE HNVVDLNAFF     540
YLHAQKVPEG ETNISLTSSI DTALSEEKV YTFFSSEFIN NINKPVHAAL FIGWISQVIR     600
DFTTESTQKS TVDKIADISL IVPYVGLALN IGNDARKGNF KEAFELLGAA ILLEVVPELL     660
IPVILVFTIK SFIDSSKNED KIIKAINNSL IEREAKWKEV YSWIVSNWLT RINTQFNKRK     720
EQMYQALQNQ VDAIKTVIEY KYNSYTSDEK NRLESEYNIN NIEEELNKKV SLAMKNIERF     780
IAESSISYLM KLINEAKVSE LREYDEGVKE YLLDYILKNG SILGDHVQEL NDLVTSTLNS     840
SIPFELSSYT NDKILIIYFN KLYKKIKDNC ILDMRYENNK FIDISGYGSN ISINGELYIY     900
TTNRNQFTIY SGKLSEVNIA QNNDIIYNSR YQNFSISFWV RIPRYSNIVN LNNEYTIINC     960
MGNNNSGWKI SLNYNKIIWT LQDTAGNNEK LVFNYTQMIS ISDYINKWIF VTITNNRLGN    1020
SRIYINGNLI DQKSISNLGD IHVSDNILFK IVGCNDTRYV GIRYFKVFDT ELDKTEIETL    1080
YSDEPDPSIL KDFWGNYLLY NKRYYLLNLL RKDNAITQSS TFLSISRARG VDRKANIFSN    1140
KRLYKGVEVI IRKNEPIDIS NTDNFVRKGD LAYINVVDRD VEYRLYANTS NAQPEKTIKL    1200
IRTSNSNDSL DQIIVMDSIG NNCTMNFQNN NGGNIGLLGF HSNTLVASSW YYNNIRRNTS    1260
SNGCFWSFIS KEHGWQE                                                  1277

SEQ ID NO: 89           moltype = AA  length = 1280
FEATURE                 Location/Qualifiers
source                  1..1280
                        mol_type = protein
                        organism = Clostridium botulinum
SEQUENCE: 89
MPVVINSFNY NDPVNDETIL YMQKPYEERS RKYYKAFEIM PNVWIMPERD TIGTKPDEFQ      60
VPDSLKNGSS AYYDPNYLTT DAEKDRYLKT MIKLFNRINS NPTGKVLLEE VSNARPYLGD     120
DDTLINEFFP VNVTTSVNIK FSTDVESSII SNLLVLGAGP DIFKAYCTPL VRFNKSDKLI     180
EPSNHGFGSI NILTFSPEYE HIFNDISGGN HNSTESFIAD PAISLAHELI HALHGLYGAK     240
AVTHKESLVA ERGPLMIAEK PIRLEEFLTF GGEDLNIIPS AMKEKIYNDL LANYEKIATR     300
LREVNTAPPG YDINEYKDYF QWKYGLDRNA DGSYTVNRNK FNEIYKKLYS FTEIDLANKF     360
KVKCRNTYFI KYGFVKVPDL LDDDIYTVSE GFNIGNLAVN NRGQNINLNP KIIDSIPDKG     420
LVEKIIKFCK SIIPRKGTKQ SPSLCIRVNN RELFFVASES SYNESDINTP KEIDDTTNLN     480
NNYRNNLDEV ILDYNSETIP QISNRTLNTL VQDNSYVPRY DSNGTSEIEE YDVVDFNVFF     540
YLHAQKVPEG ETNISLTSSI DTALLEESKV YTFFSSEFID TINKPVNAAL FIDWISKVIR     600
DFTTEATQKS TVDKIADISL IVPYVGLALN IVIEAEKGNF EEAFELLGAG ILLEFVPELT     660
IPVILVFTIK SYIDSYENKN KAIKAINNSL IEREAKWKEI YSWIVSNWLT RINTQFNKRK     720
EQMYQALQNQ VDAIKTAIEY KYNNYTSDEK NRLESKYNIN NIEEELNKKV SLAMKNIERF     780
MTESSISYLM KLINEAVGK LKEYDKHVKS DLLDYILHNG LILGEQTKEL IDLVTSTLNS     840
SIPFELSSYT NDKILIIYFN RLYKKIKDSS ILDMRYENNK FIDISGYGSN ISINGNVYIY     900
STNRNQFGIY SGRLSEVNIA QNNDIIYNSR YQNFSISFWV RIPKHYRPMN RNREYTIINC     960
MGNNNSGWKI SLRTIRDCEI IWTLQDTSGN KEKLIFRYEE LASISDYINK WIFVTITNNR    1020
LGNSRIYING NLIVEKSISN LGDIHVSDNI LFKIVGCDDE TVGIRYFKV FNTELDKTEI     1080
ETLYSNEPDP SILKDYWGNY LLYNKKYYLF NLLRKDKYIT RNSGILNINQ QRGVTGGISV    1140
FLNYKLYEGV EVIIRKNAPI DISNTDNFVR KNDLAYINVV DHGVEYRLYA DISITKSEKI    1200
IKLIRTSNPN DSLGQIIVMD SIGNNCTMNF QNNDGSNIGL LGFHSDDLVA SSWYYNHIRR    1260
NTSSNGCFWS FISKEHGWKE                                               1280

SEQ ID NO: 90           moltype = AA  length = 1279
FEATURE                 Location/Qualifiers
source                  1..1279
                        mol_type = protein
                        organism = Clostridium botulinum
SEQUENCE: 90
MPVVINSFNY NDPVNDETIL YMQKPYEERS RKYYKAFEIM PNVWIMPERD TIGTKPDDFQ      60
VPDSLKNGSS AYYDPNYLTT DAEKDRYLKT MIKLFNRINS NPTGKVLLEE VSNARPYLGD     120
DDTLINEFFP VNVTTSVNIK FSTDVESSII SNLLVLGAGP DIFKAYCTPL VRFNKSDKLI     180
EPSNHGFGSI NILTFSPEYE HIFNDISGGD HNSTESFIAD PAISLAHELI HALHGLYGAK     240
AVTHKETIEV KRGPLMIAEK PIRLEEFLTF GGEDLNIIPS AMKEKIYNDL LANYEKIATR     300
LREVNTAPPE YDINEYKDYF QWKYGLDRNA DGSYTVNRNK FNGIYKKLYS FTEIDLANKF     360
KVKCRNTYFI KYGFVKVPDL LDDDIYTVSE GFNIGNLAVN NRGQNINLNP KIIDSIPDKG     420
LVEKIIKFCK SIIPRKGTKQ SPSLCIRVNN RELFFVASES SYNESDINTP KEIDDTTNLN     480
NNYRNNLDEV ILDYNSETIP QISNRTLNTL VQDNSYVPRY DSNGTSEIEE YDVVDFNVFF     540
```

```
YLHAQKVPEG ETNISLTSSI DTALLEKSKV YTFFSSEFID TINESVNAAL FIDWINKVIR  600
DFTTEATQKS TVDKIADISL IVPYVGLALN IVIDAEKGNF QEAFELLGAG ILLEFVPELT  660
IPVILVFTIK SYIDSYENKN KAIKAINNAL IEREAKWKEI YSWIVSNWLT KINTQFNKRK  720
EQMYQALQNQ VDAIKTAIEY KYNNYTSDEK NRLESEYNIN NIEEELNKKV SLAMKNIERF  780
MTESSISYLM KLINEAEVGK LKKYDRHVKS DLLDYILYHK LILGDQTKEL IDLVTSTLNS  840
SIPFELSSYT NDKILIIYFN RLYKKIKDSS ILDMRYENNK FIDISGYGSN ISINGNVYIY  900
STNRNQFGIY SDRLSEVNIA QNNDIIYNSR YQNFSISFWV RIPKHYGPMN RNREYTIINC  960
MGNNNSGWKI SLRNIRDCEI IWTLQDTSGN KEKLIFRYEE LANISDYINK WIFVTITNNR  1020
LGNSRIYING NLIVEKSISN LGDIHVSDNI LFKIVGCDDK TYVGIRYFKV FNTELDKTEI  1080
ETLYSNEPDP SILKDYWGNY LLYNKKYYLF NLLRKDKYIT RNSGILNINQ QRGVTEGSVF  1140
LNYKLYEGVE VIIRKNGPID ISNTDNFVRK NDLAYINVVY HDVEYRLYAD ISITKPEKII  1200
KLIRTSNPND SLGQIIVMDS IGNNCTMNFQ NNNGGNIGLL GFHSDNLVAS SWYYNNIRRN  1260
TSSNGCFWSF ISKEHGWQE                                              1279

SEQ ID NO: 91          moltype = AA   length = 1274
FEATURE                Location/Qualifiers
source                 1..1274
                       mol_type = protein
                       organism = Clostridium botulinum
SEQUENCE: 91
MPVAINSFNY NDPVNDDTIL YMQIPYEEKS KKYYKAFEIM RNVWIIPERN TIGTNPSDFD  60
PPASLKNGSS AYYDPNYLTT DAEKDRYLKT TIKLFKRINS NPAGKVLLQE ISYAKPYLGN  120
DHTPIDEFSP VTRTTSVNIK LSTNVESSML LNLLVLGAGP DIFESCCYPV RKLIDPDVVY  180
DPSNYGFGSI NIVTFSPEYE YTFNDISGGH NSSTESFIAD PAISLAHELI HALHGLYGAR  240
GVTYEETIEV KQAPLMIAEK PIRLEEFLTF GGQDLNIITS AMKEKIYNNL LANYEKIATR  300
LSEVNSAPPE YDINEYKDYF QWKYGLDKNA DGSYTVNENK FNEIYKKLYS FTESDLANKF  360
KVKCRNTYFI KYEFLKVPNL LDDDIYTVSE GFNIGNLAVN NRGQSIKLNP KIIDSIPDKG  420
LVEKIVKFCK SVIPRKGTKA PPRLCIRVNN SELFFVASES SYNENDINTP KEIDDTTNLN  480
NNYRNNLDEV ILDYNSQTIP QISNRTLNTL VQDNSYVPRY DSNGTSEIEE YDVVDFNVFF  540
YLHAQKVPEG ETNISLTSSI DTALLEESKD IFFSSEFIDT INKPVNAALF IDWISKVIRD  600
FTTEATQKST VDKIADISLI VPYVGLALNI IIEAEKGNFE EAFELLGVGI LLEFVPELTI  660
PVILVFTIKS YIDSYENKNK AIKAINNSLI EREAKWKEIY SWIVSNWLTR INTQFNKRKE  720
QMYQALQNQV DAIKTAIEYK YNNYTSDEKN RLESEYNINN IEEELNKKVS LAMKNIERFM  780
TESSISYLMK LINEAKVGKL KKYDNHVKSD LLNYILDHRS ILGEQTNELS DLVTSTLNSS  840
IPFELSSYTN DKILIIYFNR LYKKIKDSSI LDMRYENNKF IDISGYGSNI SINGNVYIYS  900
TNRNQFGIYN SRLSEVNIAQ NNDIIYNSRY QNFSISFWVR IPKHYKPMNH NREYTIINCM  960
GNNNSGWKIS LRTVRDCEII WTLQDTSGNK ENLIFRYEEL NRISNYINKW IFVTITNNRL  1020
GNSRIYINGN LIVEKSISNL GDIHVSDNIL FKIVGCDDET YVGIRYFKVF NTELDKTEIE  1080
TLYSNEPDPS ILKNYWGNYL LYNKKYYLFN LLRKDKYITL NSGILNINQQ RGVTEGSVFL  1140
NYKLYEGVEV IIRKNGPIDI SNTDNFVRKN DLAYINVVDR GVEYRLYADT KSEKEKIIRT  1200
SNLNDSLGQI IVMDSIGNNC TMNFQNNNGS NIGLLGFHSN NLVASSWYYN NIRRNTSSNG  1260
CFWSSISKEN GWKE                                                   1274
```